US011185440B2

(12) United States Patent
Dabrowiak et al.

(10) Patent No.: US 11,185,440 B2
(45) Date of Patent: Nov. 30, 2021

(54) DEVICES, SYSTEMS AND METHODS FOR ENDOVASCULAR TEMPERATURE CONTROL

(71) Applicant: ZOLL Circulation, Inc., San Jose, CA (US)

(72) Inventors: Jeremy Thomas Dabrowiak, Santa Clara, CA (US); Jessica Megan Clayton, San Jose, CA (US); John Thomas Buckley, San Jose, CA (US); Christo Petrov Pamichev, Cupertino, CA (US); Craig Wendell Pendry, Milpitas, CA (US); Paul Eric Peterson, Pacifica, CA (US); Richard Allen Smith, Campbell, CA (US); Sean W Yip, San Jose, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 256 days.

(21) Appl. No.: 15/423,581

(22) Filed: Feb. 2, 2017

(65) Prior Publication Data

US 2018/0214302 A1 Aug. 2, 2018

(51) Int. Cl.
*A61F 7/12* (2006.01)
*A61F 7/00* (2006.01)

(52) U.S. Cl.
CPC .............. *A61F 7/12* (2013.01); *A61F 7/0085* (2013.01); *A61F 2007/0054* (2013.01); *A61F 2007/0093* (2013.01); *A61F 2007/0095* (2013.01); *A61F 2007/126* (2013.01)

(58) Field of Classification Search
CPC ....... A61F 7/12; A61F 7/123; A61F 2007/126
See application file for complete search history.

(56) References Cited

U.S. PATENT DOCUMENTS

| | | | |
|---|---|---|---|
| 1,459,112 A | 6/1923 | Mehl | |
| 1,726,761 A | 9/1929 | Palmer | |
| 1,857,031 A | 5/1932 | Schaffer | |
| 2,223,688 A | 12/1940 | Otoo | |
| 2,663,030 A | 12/1953 | Dahlberg | |
| 2,673,987 A | 4/1954 | Upshaw et al. | |
| 2,987,004 A | 6/1961 | Murray | |
| 3,140,716 A | 7/1964 | Harrison | |
| 3,225,191 A | 12/1965 | Calhoun | |
| 3,228,465 A | 1/1966 | Vadot | |
| 3,369,549 A | 2/1968 | Armao | |
| 3,425,419 A | 2/1969 | Dato | |

(Continued)

FOREIGN PATENT DOCUMENTS

| | | |
|---|---|---|
| CN | 101090685 | 12/2007 |
| DE | 19531935 A1 | 2/1997 |

(Continued)

OTHER PUBLICATIONS

Behringer, et al., "Rapid Hypothermic Aortic Flush Can Achieve Survival without Brain Damage after 30 minutes Cardiac Arrest in Dogs", Anesthesiology, vol. 93, No. 6, Dec. 2000.

(Continued)

*Primary Examiner* — Kaitlyn E Smith
(74) *Attorney, Agent, or Firm* — ZOLL Circulation, Inc.

(57) ABSTRACT

Devices, systems and methods for controlling a patient's body temperature by endovascular heat exchange.

25 Claims, 37 Drawing Sheets

(56) References Cited

U.S. PATENT DOCUMENTS

| | | |
|---|---|---|
| 3,504,674 A | 4/1970 | Swenson et al. |
| 3,726,269 A | 4/1973 | Webster, Jr. |
| 3,744,555 A | 7/1973 | Fletcher et al. |
| 3,751,077 A | 8/1973 | Hiszpanski |
| 3,834,396 A | 9/1974 | Foster |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,181,245 A | 1/1980 | Garrett et al. |
| 4,259,961 A | 4/1981 | Hood |
| 4,298,006 A | 11/1981 | Parks |
| 4,459,468 A | 7/1984 | Bailey |
| 4,532,414 A | 7/1985 | Shah et al. |
| 4,552,516 A | 11/1985 | Stanley |
| 4,554,793 A | 11/1985 | Harding, Jr. |
| 4,558,996 A | 12/1985 | Becker |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,869,250 A | 9/1989 | Bitterly |
| 4,906,237 A | 3/1990 | Johansson et al. |
| 4,925,376 A | 5/1990 | Kahler |
| 4,941,475 A | 7/1990 | Williams et al. |
| 4,976,590 A | 12/1990 | Baldwin |
| 5,080,089 A | 1/1992 | Mason et al. |
| 5,092,841 A | 3/1992 | Spears |
| 5,103,360 A | 4/1992 | Maeda |
| 5,106,360 A | 4/1992 | Ishiwara et al. |
| 5,174,285 A | 12/1992 | Fontenot |
| 5,192,274 A | 3/1993 | Bierman |
| 5,195,965 A | 3/1993 | Shantha |
| 5,211,631 A | 5/1993 | Sheaff |
| 5,263,925 A | 11/1993 | Gilmore et al. |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,391,030 A | 2/1995 | Lee |
| 5,403,281 A | 4/1995 | O'Neill et al. |
| 5,433,588 A | 7/1995 | Monk |
| 5,433,740 A | 7/1995 | Yamaguchi |
| 5,437,673 A | 8/1995 | Baust et al. |
| 5,458,639 A | 10/1995 | Tsukashima et al. |
| 5,466,208 A | 11/1995 | Jackson |
| 5,476,368 A * | 12/1995 | Rabenau ............... F04B 43/02 417/395 |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,693,344 A | 12/1997 | Knight |
| 5,701,905 A | 12/1997 | Esch |
| 5,706,889 A | 1/1998 | Bach et al. |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,746,585 A | 5/1998 | McDunn |
| 5,746,885 A | 5/1998 | McDunn |
| 5,759,017 A | 6/1998 | Patton et al. |
| 5,776,079 A | 7/1998 | Cope et al. |
| 5,788,647 A | 8/1998 | Eggers |
| 5,803,324 A | 9/1998 | Silberman |
| 5,837,003 A | 11/1998 | Ginsburg |
| 5,857,843 A | 1/1999 | Leason |
| 5,862,675 A | 1/1999 | Scaringe et al. |
| 5,875,282 A | 2/1999 | Jordan |
| 5,879,329 A | 3/1999 | Ginsburg |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 5,989,238 A | 11/1999 | Ginsburg |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,110,168 A | 8/2000 | Ginsburg |
| 6,117,065 A | 9/2000 | Hastings et al. |
| 6,117,105 A | 9/2000 | Bresnaham et al. |
| 6,124,452 A | 9/2000 | DiMagno |
| 6,126,684 A | 10/2000 | Gobin et al. |
| 6,146,141 A | 11/2000 | Schumann |
| 6,146,411 A * | 11/2000 | Noda .................. A61F 7/12 607/105 |
| 6,148,634 A | 11/2000 | Sherwood |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,149,806 A | 11/2000 | Baer |
| 6,165,207 A | 12/2000 | Balding |
| 6,188,930 B1 | 2/2001 | Carson et al. |
| 6,197,045 B1 | 3/2001 | Carson et al. |
| 6,224,624 B1 | 5/2001 | Lasheras |
| 6,231,594 B1 | 5/2001 | Dae |
| 6,231,595 B1 | 5/2001 | Dobak |
| 6,235,048 B1 | 5/2001 | Dobak |
| 6,238,428 B1 | 5/2001 | Werneth |
| 6,245,095 B1 | 6/2001 | Dobak |
| 6,251,129 B1 | 6/2001 | Dobak |
| 6,251,130 B1 | 6/2001 | Dobak |
| 6,254,626 B1 | 7/2001 | Dobak |
| 6,261,312 B1 | 7/2001 | Dobak |
| 6,264,679 B1 | 7/2001 | Keller |
| 6,283,940 B1 | 9/2001 | Mulholland |
| 6,287,326 B1 | 9/2001 | Pecor |
| 6,290,717 B1 | 9/2001 | Philips et al. |
| 6,299,599 B1 | 10/2001 | Pham et al. |
| 6,306,161 B1 | 10/2001 | Ginsburg |
| 6,312,452 B1 | 11/2001 | Dobak |
| 6,325,818 B1 | 12/2001 | Werneth |
| 6,338,727 B1 | 1/2002 | Noda et al. |
| 6,364,899 B1 | 4/2002 | Dobak |
| 6,368,304 B1 | 4/2002 | Aliberto |
| 6,375,674 B1 | 4/2002 | Carson et al. |
| 6,379,378 B1 | 4/2002 | Werneth |
| 6,383,144 B1 | 5/2002 | Mooney et al. |
| 6,383,210 B1 | 5/2002 | Magers |
| 6,387,326 B1 | 5/2002 | Edwards et al. |
| 6,393,320 B2 | 5/2002 | Lasersohn |
| 6,399,599 B1 | 6/2002 | Albert |
| 6,405,080 B1 | 6/2002 | Lasersohn |
| 6,409,747 B1 | 6/2002 | Gobin et al. |
| 6,416,533 B1 | 7/2002 | Gobin et al. |
| 6,419,643 B1 | 7/2002 | Shimada et al. |
| 6,428,563 B1 | 8/2002 | Keller |
| 6,440,468 B1 | 8/2002 | Quintanilla |

(56) References Cited

U.S. PATENT DOCUMENTS

| | | | |
|---|---|---|---|
| 6,450,990 B1 | 9/2002 | Walker et al. | |
| 6,461,379 B1 | 10/2002 | Carson et al. | |
| 6,464,666 B1 | 10/2002 | Augustine et al. | |
| 6,464,716 B1 | 10/2002 | Dobak, III et al. | |
| 6,527,798 B2 | 3/2003 | Ginsburg et al. | |
| 6,530,946 B1 | 3/2003 | Noda et al. | |
| 6,544,282 B1 | 4/2003 | Dae et al. | |
| 6,551,309 B1 | 4/2003 | LePivert | |
| 6,554,791 B1 | 4/2003 | Cartledge et al. | |
| 6,582,387 B2* | 6/2003 | Derek | A61M 1/32 128/200.14 |
| 6,605,106 B2 | 8/2003 | Schwartz | |
| 6,610,083 B2 | 8/2003 | Keller et al. | |
| 6,613,280 B2* | 9/2003 | Myrick | A61M 1/32 128/200.14 |
| 6,620,187 B2 | 9/2003 | Carson et al. | |
| 6,620,188 B1 | 9/2003 | Ginsburg et al. | |
| 6,620,189 B1* | 9/2003 | Machold | A61M 25/10 607/106 |
| 6,622,542 B2* | 9/2003 | Derek | A61M 1/3626 604/65 |
| 6,624,679 B2 | 9/2003 | Tomaiuolo et al. | |
| 6,635,076 B1 | 10/2003 | Ginsburg | |
| 6,635,079 B2 | 10/2003 | Ginsburg | |
| 6,645,232 B2 | 11/2003 | Carson et al. | |
| 6,648,905 B2 | 11/2003 | Hoglund | |
| 6,660,027 B2 | 12/2003 | Gruszecki | |
| 6,669,715 B2 | 12/2003 | Hoglund | |
| 6,673,098 B1* | 1/2004 | Machold | A61F 7/123 607/104 |
| 6,675,835 B2* | 1/2004 | Gerner | B01D 19/0031 138/26 |
| 6,679,906 B2 | 1/2004 | Hammack et al. | |
| 6,685,731 B2 | 2/2004 | Kushnir et al. | |
| 6,685,733 B1 | 2/2004 | Dae et al. | |
| 6,692,518 B2 | 2/2004 | Carson et al. | |
| 6,695,874 B2* | 2/2004 | Machold | A61M 25/10 607/106 |
| 6,706,060 B2 | 3/2004 | Tzeng et al. | |
| 6,716,188 B2 | 4/2004 | Noda et al. | |
| 6,718,012 B2 | 4/2004 | Ein-Gal | |
| 6,719,723 B2 | 4/2004 | Werneth | |
| 6,719,779 B2 | 4/2004 | Daoud | |
| 6,726,653 B2 | 4/2004 | Noda et al. | |
| 6,733,495 B1 | 5/2004 | Bek et al. | |
| 6,740,109 B2 | 5/2004 | Dobak, III | |
| 6,743,201 B1 | 6/2004 | Donig et al. | |
| 6,764,391 B1 | 7/2004 | Grant | |
| 6,799,063 B2 | 9/2004 | Carson et al. | |
| 6,799,342 B1 | 10/2004 | Jarmon | |
| 6,802,855 B2 | 10/2004 | Ellingboe | |
| 6,818,012 B2 | 11/2004 | Ellingboe | |
| 6,827,728 B2 | 12/2004 | Ellingboe | |
| 6,843,099 B2* | 1/2005 | Derek | A61M 1/3626 73/19.01 |
| 6,843,800 B1 | 1/2005 | Dobak, III | |
| 6,878,156 B1 | 4/2005 | Noda | |
| 6,887,263 B2 | 5/2005 | Bleam et al. | |
| 6,890,347 B2* | 5/2005 | Machold | A61F 7/123 417/477.2 |
| 6,893,419 B2 | 5/2005 | Noda et al. | |
| 6,969,399 B2 | 11/2005 | Schock et al. | |
| 6,974,435 B2* | 12/2005 | Daw | A61M 1/32 604/6.14 |
| 6,997,942 B2* | 2/2006 | Machold | A61F 7/123 417/477.2 |
| 7,070,612 B1 | 7/2006 | Collins et al. | |
| 7,104,769 B2 | 9/2006 | Davis | |
| 7,140,850 B2 | 11/2006 | Otis, Jr. | |
| 7,175,649 B2* | 2/2007 | Machold | A61M 25/10 607/104 |
| 7,181,927 B2 | 2/2007 | Collins | |
| 7,211,106 B2 | 5/2007 | Dobak | |
| 7,247,165 B2* | 7/2007 | Machold | A61F 7/123 607/104 |
| 7,258,662 B2* | 8/2007 | Machold | A61M 25/10 600/104 |
| 7,357,786 B1 | 4/2008 | Bakke | |
| 7,377,935 B2 | 5/2008 | Schock | |
| 7,510,569 B2 | 3/2009 | Dae et al. | |
| 7,516,909 B2* | 4/2009 | Kaligian, II | B01F 5/0451 239/419.3 |
| 7,645,127 B2* | 1/2010 | Hagen | F04B 43/1253 417/477.1 |
| 7,658,755 B2* | 2/2010 | Machold | A61F 7/123 607/113 |
| 7,666,215 B2* | 2/2010 | Callister | A61F 7/12 607/105 |
| 7,713,036 B2 | 5/2010 | Kojima | |
| 7,820,102 B2* | 10/2010 | Myrick | A61M 1/32 422/44 |
| 7,822,485 B2 | 10/2010 | Collins | |
| 7,846,193 B2 | 12/2010 | Dae et al. | |
| 7,857,781 B2 | 12/2010 | Noda et al. | |
| 7,879,077 B2* | 2/2011 | MacHold | A61M 25/10 607/96 |
| 7,892,269 B2 | 2/2011 | Collins et al. | |
| 7,914,564 B2 | 3/2011 | Magers | |
| 7,959,657 B1 | 6/2011 | Harsy | |
| 7,963,986 B2* | 6/2011 | Machold | A61M 25/10 607/105 |
| 8,105,262 B2 | 1/2012 | Noda et al. | |
| 8,105,263 B2 | 1/2012 | Noda et al. | |
| 8,105,264 B2 | 1/2012 | Noda et al. | |
| 8,109,894 B2 | 2/2012 | Noda et al. | |
| 8,128,384 B2 | 3/2012 | Mou | |
| 8,177,824 B2* | 5/2012 | Machold | A61F 7/12 607/104 |
| 8,226,605 B2 | 7/2012 | Faries, Jr. et al. | |
| 8,246,669 B2* | 8/2012 | Machold | A61F 7/12 607/104 |
| 8,272,857 B2 | 9/2012 | Norman et al. | |
| 8,366,667 B2* | 2/2013 | Chan | A61M 5/14212 604/132 |
| 8,551,151 B2* | 10/2013 | Machold | A61F 7/12 607/105 |
| 8,740,959 B2* | 6/2014 | Machold | A61F 7/12 607/104 |
| 8,784,464 B2* | 7/2014 | Machold | A61F 7/12 607/105 |
| 8,888,729 B2 | 11/2014 | Noda | |
| 9,345,614 B2* | 5/2016 | Schaefer | A61F 7/0085 |
| 9,474,644 B2 | 10/2016 | Dabrowiak | |
| 9,492,633 B2 | 11/2016 | Dabrowiak | |
| 9,675,756 B2* | 6/2017 | Kamen | A61M 5/16859 |
| 9,784,263 B2 | 10/2017 | Hendricks | |
| 10,022,265 B2* | 7/2018 | Pamichev | A61F 7/0085 |
| 10,085,880 B2* | 10/2018 | Machold | A61M 25/10 |
| 2001/0031946 A1 | 10/2001 | Walker et al. | |
| 2001/0047196 A1 | 11/2001 | Ginsburg et al. | |
| 2002/0004675 A1 | 1/2002 | Lasheras | |
| 2002/0013569 A1 | 1/2002 | Sterman et al. | |
| 2002/0022823 A1 | 2/2002 | Luo et al. | |
| 2002/0117559 A1* | 8/2002 | Kaligian, II | B01F 5/0451 239/413 |
| 2002/0134134 A1* | 9/2002 | Derek | A61M 1/3626 73/19.03 |
| 2002/0136662 A1* | 9/2002 | Myrick | A61M 1/32 422/45 |
| 2002/0138034 A1* | 9/2002 | Derek | A61M 1/32 604/6.14 |
| 2002/0145525 A1 | 10/2002 | Friedman et al. | |
| 2002/0183692 A1 | 12/2002 | Callister | |
| 2002/0198579 A1 | 12/2002 | Khanna | |
| 2003/0036495 A1 | 2/2003 | Datta | |
| 2003/0041911 A1* | 3/2003 | Gerner | B01D 19/0031 138/30 |
| 2003/0062090 A1 | 4/2003 | Secondo | |
| 2003/0114795 A1 | 6/2003 | Durward | |

(56) References Cited

U.S. PATENT DOCUMENTS

| | | | |
|---|---|---|---|
| 2003/0135252 A1* | 7/2003 | MacHold | A61M 25/10 607/106 |
| 2003/0036496 A1 | 12/2003 | Samson | |
| 2003/0236496 A1 | 12/2003 | Samson et al. | |
| 2004/0013566 A1* | 1/2004 | Myrick | A61M 1/32 422/45 |
| 2004/0019319 A1* | 1/2004 | Derek | A61M 1/32 604/24 |
| 2004/0024437 A1* | 2/2004 | Machold | A61F 7/123 607/105 |
| 2004/0026068 A1 | 2/2004 | Schmidt | |
| 2004/0039431 A1* | 2/2004 | Machold | A61M 25/10 607/106 |
| 2004/0050154 A1* | 3/2004 | Machold | A61M 25/10 73/204.11 |
| 2004/0089050 A1* | 5/2004 | Daw | A61M 1/3626 73/1.02 |
| 2004/0089058 A1 | 5/2004 | De Haan et al. | |
| 2004/0102825 A1* | 5/2004 | Daoud | A61F 7/0085 607/105 |
| 2004/0104018 A1 | 6/2004 | Hughes | |
| 2004/0143311 A1* | 7/2004 | Machold | A61F 7/123 607/96 |
| 2004/0154374 A1* | 8/2004 | Daw | A61M 1/3626 73/1.02 |
| 2004/0171935 A1 | 9/2004 | Van Creveld et al. | |
| 2004/0190255 A1 | 9/2004 | Cheon | |
| 2004/0199230 A1 | 10/2004 | Yon | |
| 2004/0210231 A1 | 10/2004 | Boucher et al. | |
| 2004/0267340 A1* | 12/2004 | Cioanta | A61F 7/123 607/105 |
| 2005/0053502 A1 | 3/2005 | Souza | |
| 2005/0065584 A1* | 3/2005 | Schiff | A61F 7/12 607/105 |
| 2005/0069437 A1 | 3/2005 | Mittelstein | |
| 2005/0075705 A1* | 4/2005 | Machold | A61F 7/123 607/96 |
| 2005/0137662 A1 | 6/2005 | Morris | |
| 2005/0156744 A1 | 7/2005 | Pires | |
| 2005/0209658 A1* | 9/2005 | Machold | A61F 7/123 607/96 |
| 2006/0064146 A1* | 3/2006 | Collins | A61F 7/0085 607/105 |
| 2006/0069418 A1 | 3/2006 | Schock | |
| 2006/0122673 A1 | 6/2006 | Callister | |
| 2006/0210424 A1 | 9/2006 | Mallett et al. | |
| 2006/0241335 A1 | 10/2006 | Benkowski et al. | |
| 2006/0253095 A1 | 11/2006 | Stull | |
| 2006/0293734 A1* | 12/2006 | Scott | A61F 7/12 607/105 |
| 2007/0007640 A1 | 1/2007 | Harnden et al. | |
| 2007/0076401 A1 | 4/2007 | Carrez et al. | |
| 2007/0093710 A1 | 4/2007 | Maschke | |
| 2007/0156006 A1 | 7/2007 | Smith | |
| 2007/0173759 A1 | 7/2007 | Augustine | |
| 2007/0191918 A1* | 8/2007 | MacHold | A61M 25/10 607/105 |
| 2007/0203552 A1* | 8/2007 | Machold | A61M 25/10 607/104 |
| 2007/0293919 A1* | 12/2007 | Machold | A61F 7/123 607/104 |
| 2008/0026068 A1 | 1/2008 | Brown et al. | |
| 2008/0082051 A1 | 4/2008 | Miller | |
| 2008/0114430 A1 | 5/2008 | Collins | |
| 2008/0119916 A1 | 5/2008 | Choucair | |
| 2008/0230530 A1 | 9/2008 | Augustine | |
| 2008/0262409 A1 | 10/2008 | Derrico | |
| 2008/0267599 A1 | 10/2008 | Arnold | |
| 2008/0269663 A1 | 10/2008 | Arnold | |
| 2009/0065565 A1 | 3/2009 | Cao | |
| 2009/0099518 A1 | 4/2009 | Magers | |
| 2009/0160297 A1 | 6/2009 | Anikhindi | |
| 2009/2606778 | 8/2009 | Roh | |
| 2009/0247963 A1 | 10/2009 | Bleam | |
| 2009/0299287 A1 | 12/2009 | Carson | |
| 2010/0036486 A1 | 2/2010 | Mazur | |
| 2010/0049119 A1* | 2/2010 | Norman | A61M 1/0058 604/31 |
| 2010/0082000 A1 | 4/2010 | Honeck | |
| 2010/0129248 A1 | 5/2010 | Mou | |
| 2010/0204765 A1 | 8/2010 | Hall et al. | |
| 2010/0256601 A1 | 10/2010 | Lippert | |
| 2011/0022136 A1 | 1/2011 | Scott | |
| 2011/0046551 A1 | 2/2011 | Augustine | |
| 2011/0137249 A1 | 6/2011 | Collins | |
| 2011/0184253 A1 | 7/2011 | Archer | |
| 2011/0208276 A1* | 8/2011 | Machold | A61F 7/123 607/104 |
| 2011/0208277 A1* | 8/2011 | Machold | A61F 7/123 607/104 |
| 2011/0208278 A1* | 8/2011 | Machold | A61F 7/123 607/106 |
| 2011/0213305 A1 | 9/2011 | Jonsson | |
| 2012/0095536 A1* | 4/2012 | Machold | A61M 25/10 607/105 |
| 2012/0100023 A1 | 4/2012 | Hanazuka | |
| 2012/0148415 A1 | 6/2012 | Bruecker | |
| 2012/0158103 A1 | 6/2012 | Bedsoe | |
| 2012/0226338 A1* | 9/2012 | Machold | A61F 7/123 607/105 |
| 2013/0071270 A1 | 3/2013 | Zupp | |
| 2013/0079853 A1 | 3/2013 | Pasche | |
| 2013/0079855 A1 | 3/2013 | Helkowski et al. | |
| 2013/0079856 A1 | 3/2013 | Dabrowiak et al. | |
| 2013/0090708 A1 | 4/2013 | Dabrowiak et al. | |
| 2013/0090709 A1* | 4/2013 | Machold | A61M 25/10 607/106 |
| 2013/0098880 A1* | 4/2013 | Korolev | B23K 10/00 219/121.5 |
| 2013/0150929 A1* | 6/2013 | Machold | A61M 25/10 607/105 |
| 2013/0150930 A1* | 6/2013 | Machold | A61F 7/123 607/105 |
| 2013/0172805 A1* | 7/2013 | Truckai | A61M 1/0031 604/28 |
| 2013/0178923 A1 | 7/2013 | Dabrowiak | |
| 2013/0331774 A1 | 12/2013 | Farrell | |
| 2013/0337732 A1 | 12/2013 | Nilliams | |
| 2014/0081202 A1 | 3/2014 | Tsoukalis | |
| 2014/0094880 A1 | 4/2014 | Lim et al. | |
| 2014/0094882 A1 | 4/2014 | Lim | |
| 2014/0094883 A1 | 4/2014 | Lim et al. | |
| 2014/0276792 A1* | 9/2014 | Kaveckis | A61B 18/1492 606/41 |
| 2014/0277302 A1* | 9/2014 | Weber | A61F 7/0085 607/104 |
| 2014/0364928 A1* | 12/2014 | Machold | A61F 7/123 607/106 |
| 2015/0223974 A1 | 8/2015 | Dabrowiak | |
| 2015/0230973 A1 | 8/2015 | Dabrowiak | |
| 2015/0230974 A1 | 8/2015 | Pistor | |
| 2015/0230975 A1 | 8/2015 | Dabrowiak | |
| 2015/0314055 A1 | 11/2015 | Hogard et al. | |
| 2016/0022477 A1* | 1/2016 | Schaefer | A61F 7/0085 607/104 |
| 2016/0089184 A1* | 3/2016 | Truckai | A61M 1/0031 604/31 |
| 2016/0131127 A1 | 5/2016 | Hendricks | |
| 2016/0166758 A1* | 6/2016 | Norman | A61M 1/0058 604/22 |
| 2016/0228291 A1 | 8/2016 | Calliser et al. | |
| 2016/0287432 A1 | 10/2016 | Dabrowiak | |
| 2016/0287433 A1 | 10/2016 | Mazzone | |
| 2016/0287434 A1 | 10/2016 | Dabrowiak et al. | |
| 2016/0287435 A1* | 10/2016 | Pamichev | A61F 7/0085 |
| 2016/0290330 A1 | 10/2016 | Pamichev | |
| 2017/0035604 A1 | 2/2017 | Dabrowiak | |
| 2018/0128258 A1 | 5/2018 | Hendricks | |
| 2018/0185192 A1 | 7/2018 | Mazzone et al. | |
| 2018/0185193 A1 | 7/2018 | Mazzone et al. | |
| 2018/0207024 A1 | 7/2018 | Dabrowiak et al. | |

(56) References Cited

U.S. PATENT DOCUMENTS

| | | | |
|---|---|---|---|
| 2018/0214303 A1 | 8/2018 | Dabrowiak |
| 2018/0311072 A1 | 11/2018 | Pamichev |
| 2018/0325725 A1 | 11/2018 | Dabrowiak |
| 2019/0133820 A1 | 5/2019 | Jacobsen |

FOREIGN PATENT DOCUMENTS

| | | |
|---|---|---|
| DE | 102009050053 | 5/2011 |
| EP | 0663529 | 5/1997 |
| GB | 1183185 A | 3/1970 |
| GB | 2040169 A | 8/1980 |
| GB | 2212262 A | 7/1989 |
| GB | 2383828 A | 7/2003 |
| JP | S61100243 | 5/1986 |
| JP | 09-215754 A | 8/1997 |
| JP | 10-0127777 A | 5/1998 |
| JP | 10-305103 A | 11/1998 |
| JP | 2001147095 | 5/2001 |
| JP | 2002534160 | 10/2002 |
| JP | 2003028582 | 1/2003 |
| JP | 2003508150 A | 3/2003 |
| JP | 2003524507 | 8/2003 |
| JP | 2008154751 A | 7/2008 |
| JP | 2008531114 | 8/2008 |
| JP | 2008539034 | 11/2008 |
| JP | 2009500066 | 1/2009 |
| JP | 2011505929 A | 3/2011 |
| JP | 2011137621 | 7/2011 |
| JP | 2011182849 A | 9/2011 |
| JP | 2014023604 | 2/2014 |
| JP | 2017508509 | 3/2017 |
| JP | 2017511716 | 4/2017 |
| WO | 1990/001682 A1 | 2/1990 |
| WO | 1993/002730 A1 | 2/1993 |
| WO | 1993/004727 A1 | 3/1993 |
| WO | 1994/000177 A1 | 1/1994 |
| WO | 1994/001177 A1 | 1/1994 |
| WO | WO 1995003680 | 2/1995 |
| WO | 1997/025011 A1 | 7/1997 |
| WO | 1998/024491 A1 | 6/1998 |
| WO | 1998/040017 A2 | 9/1998 |
| WO | 2000/010494 A1 | 3/2000 |
| WO | 2001/013809 A1 | 3/2001 |
| WO | WO 2001026719 | 4/2001 |
| WO | 2001/064146 A1 | 9/2001 |
| WO | 2001/076517 A2 | 10/2001 |
| WO | 2001/083001 A1 | 11/2001 |
| WO | WO 2015119671 | 8/2005 |
| WO | WO 2005117546 | 12/2005 |
| WO | WO 2006036585 | 4/2006 |
| WO | WO 2009/056640 A2 | 5/2009 |
| WO | WO 2010040819 | 4/2010 |
| WO | WO 2012175089 | 12/2012 |
| WO | WO 2014160422 | 10/2014 |
| WO | WO 2015119670 | 8/2015 |
| WO | WO 2015122938 | 8/2015 |

OTHER PUBLICATIONS

Watts, Dorraine Day, et al., "Hypothermic Coagulopathy in Trauma: Effect of Varying Levels of Hypothermia on Enzyme Speed, Platelet Function, and Fibrinolytic Activity," Journal of Trauma—Injury Infection & Critical Care, vol. 44, No. 5, pp. 846-854, 1998.
F.W. Behmann, et al., "Die Regelung der Wärmebildung bei künstlicher Hypothermie," Pflügers Archiv, Bd. 266, S. 408-421 (1958).
F.W. Behmann, et al., "Intravasale Kühlung," Pflügers Archiv, Bd. 263, S. 145-165 (1956).
PCT International Search Report dated Jun. 25, 2018 in related PCT Application No. PCT/US2018/016752.
PCT International Search Report dated Jun. 25, 2018 in related PCT Application No. PCT/US2018/016754.
American Urethane Inc., "Polyurethane Properties", available Oct. 12, 2010, http://web.archive.org/web/20101012211957/hllp://americanurethane.com/polyurethane-properties.html.
Baharlou, "Written Opinion of the International Searching Authority", dated Oct. 12, 2017, from Counterpart PCT application PCT/US2016/024970.
Chinese Office Action in Application No. 201480077207.7, dated Jul. 3, 2019, 24 pages.
Dabrowiak "Heat Exchange System for Patient Temperature Control with Multiple Coolant Chambers for Multiple Heat Exchange Modalities", related pending U.S. Appl. No. 14/175,545 non-final office action dated Feb. 12, 2016.
Dabrowiak et al., "Fluid Cassette with Tensioned Polymeric Membranes for Patient Heat Exchange System", related pending U.S. Appl. No. 14/180,613, applicant's response to non-final office action filed Jun. 1, 2016.
Dabrowiak et al., "Heat Exchange System for Patient Temperature Control with Multiple Coolant Chambers for Multiple Heat Exchange Modalities" file history of related U.S. Appl. No. 14/175,545, filed Feb. 7, 2014.
Dabrowiak et al., "Patient Heat Exchange System with Transparent Wall for Viewing Circulating Refrigerant" file history of related U.S. Appl. No. 14/276,202, filed May 13, 2014.
Dabrowiak et al., "Patient Heat Exchange System with Transparent Wall for Viewing Circulating Refrigerant", related pending U.S. Appl. No. 14/276,202, applicant's response to non-final office action filed Jun. 1, 2016.
Dabrowiak et al., "Cold Plate Design in Heat Exchanger for Intravascular Temperature Management Catheter and/or Heat Exchange Pad", filed history of related U.S. Appl. No. 14/675,504, filed Mar. 31, 2015.
Dabrowiak et al., "Fluid Cassette with Tensioned Polymeric Membranes for Patient Heat Exchange System" file history of related U.S. Appl. No. 14/180,613, filed Feb. 14, 2014.
Dabrowiak et al., "Fluid Cassette with Tensioned Polymeric Membranes for Patient Heat Exchange System" file history of related pending U.S. Appl. No. 14/180,655 applicant's response to non-final office action filed Jun. 1, 2016.
Dabrowiak et al., "Fluid Cassette with Tensioned Polymeric Membranes for Patient Heat Exchange System" related pending U.S. Appl. No. 14/180,613, non-final office action dated May 19, 2016.
Dabrowiak et al., "Fluid Cassette with Tensioned Polymeric Membranes for Patient Heat Exchange System", related pending U.S. Appl. No. 14/180,613 final office action dated Jul. 15, 2016.
Dabrowiak et al., "Patient Heat Exchange System with Transparent Wall for Viewing Circulating Refrigerant" file history of related U.S. Appl. No. 14/275,202, filed May 13, 2014.
Dabrowiak et al., "Patient Heat Exchange System with Transparent Wall for Viewing Circulating Refrigerant", related pending U.S. Appl. No. 14/276,202 final office action dated Jul. 15, 2016.
Dabrowiak et al., "Patient Heat Exchange System with Transparent Wall for Viewing Circulating Refrigerant", related pending U.S. Appl. No. 14/276,202, non-final office action dated May 19, 2016.
Dabrowiak et al., "Patient Heat Exchange System with Transparent Wall for Viewing Circulating Refrigerant", related pending U.S. Appl. No. 14/276,202, applicant's response to non-final office action dated Jun. 1, 2016.
Dabrowiak et al., "Patient Heat Exchange System with Transparent Wall for Viewing Circulation Refrigerant", related pending U.S. Appl. No. 14/276,202, applicant's response to non-final office action filed Aug. 21, 2018.
Dabrowiak et al., "Patient Heat Exchange System With Two and Only Two Fluid Loops", file history of related U.S. Appl. No. 14/180,719, filed Feb. 14, 2014.
Dabrowiak et al., "Patient Heat Exchange System with Two and Only Two Fluid Loops", related U.S. Appl. No. 14/180,719, Non-Final Office Action dated Jun. 7, 2016.
Dabrowiak et al., "Patient Heat Exchange System with Two and Only Two Fluid Loops", related U.S. Appl. No. 14/180,719, Applicant's response to the Non-Final Office Action dated Sep. 7, 2016.
Dabrowiak et al., "Patient Heat Exchanger System with Transparent Wall for Viewing Circulation Refrigerant", related pending U.S. Appl. No. 14/276,202, non-final office action dated Feb. 21, 2018.

(56) References Cited

OTHER PUBLICATIONS

Dabrowiak et al., "Patient Heat Exchange System with Two and Only Two Fluid Loops", related U.S. Appl. No. 14/180,719, Applicant's Response to the Non-Final Office Action filed Sep. 7, 2016.
Dabrowiak, "Heat Exchange System for Patient Temperature Control With Multiple Coolant Chambers For Multiple Heat Exchange Modalities", File History of related pending U.S. Appl. No. 15/332,519, filed Oct. 24, 2016.
Dabrowiak, "Heat Exchange System for Patient Temperature Control with Multiple Coolant Chambers for Multiple Heat Exchange Modalities", file history of related U.S. Appl. No. 14/175,545, filed Feb. 7, 2014.
Dabrowiak, "Heat Exchange System for Patient Temperature Control with Multiple Coolant Chambers for Multiple Heat Exchange Modalities", related pending U.S. Appl. No. 14/175,545 applicants response to non-final office action dated May 2, 2016.
Dabrowiak, "Serpentine Heat Exchange Assembly for Removable Engagement with Patient Heat Exchange System" file history of related U.S. Appl. No. 14/675,421, filed Mar. 31, 2015.
Dabrowiak, "Working fluid cassette with hinged plenum or enclosure for interfacing heat exchanger with intravascular temperature management catheter", filed history of related U.S. Appl. No. 14/676,672, filed Apr. 1, 2015.
European Office Action in Application No. 16775853.1, dated Nov. 6, 2019, 5 pages.
Extra Packaging Corp, Polyurethane properties and Characteristics, accessed May 9, 2016 at http://www.extrapackaging.com/polyurethane/properites.php.
Hendricks et al., "Heat Exchange System for Patient Temperature Control with Easy Loading High Performance Peristaltic Pump" file history of related U.S. Appl. No. 14/534,718, filed Nov. 6, 2014.
Hendricks et al., "Heat Exchange System for Patient Temperature Control with Easy Loading High Performance Peristaltic Pump" file history of related U.S. Appl. No. 14/534,718, Non-Final Office Action dated Jul. 25, 2016.
Hendricks et al., "Heat Exchange System for Patient Temperature Control with Easy Loading High Performance Peristaltic Pump" file history of related U.S. Appl. No. 15/711,276, filed Aug. 9, 2018.
Hendricks et al., "Heat Exchange System for Patient Temperature Control with Easy Loading High Performance Peristaltic Pump" file history of related U.S. Appl. No. 15/711,276, filed Feb. 15, 2019.
Hendricks et al., "Heat Exchange System for Patient Temperature Control with Easy Loading High Performance Peristaltic Pump" file history of related U.S. Appl. No. 15/711,276, filed Sep. 21, 2017.
Hendricks et al., "Heat Exchange System for Patient Temperature Control with Easy Loading High Performance Peristaltic Pump", related U.S. Appl. No. 14/534,718, Non-Final Office Action dated Jul. 25, 2016.
Hendricks et al., "Heat Exchange System for Patient Temperature Control with Easy Loading High Performance Peristaltic Pump", related pending European application No. 15857869.0 extended search report dated May 8, 2018.
Japanese Office Action in Application No. 2018-118084, dated Sep. 2, 2019, 10 pages.
Japanese Office Action in Application No. 2018-160938, dated Jul. 19, 2019, 6 pages.
Mazzone, "Proximal Mounting of Temperature Sensor in Intravascular Temperature Management Catheter", file history of related U.S. Appl. No. 14/675,452, filed Mar. 31, 2015.
Pamichev et al., "Heat Exchange System for Patient Temperature Control with Easy Loading High Performance Peristaltic Pump", related co-pending U.S. Appl. No. 14/676,682, non-final office action dated Jun. 26, 2018.
Pamichev et al., "Heat Exchange System for Patient Temperature Control With Easy Loading High Performance Peristatic Pump", file history of related U.S. Appl. No. 14/676,682, filed Apr. 1, 2015.
Pamichev et al., "Heat exchange system for patient Temperature control with easy loading high preformance penstatic pump", filed history of related U.S. Appl. No. 14/676,682, filed Apr. 1, 2015.
Pamichev et al., "Working Fluid Cassette with Hinged Plenum or Enclosure for Interfacing Heat Exchanger with Intravascular Temperature Management Catheter", filed history of related U.S. Appl. No. 14/676,672, filed Apr. 1, 2015.
Pistor et al., "Fluid Cassette with Polymeric Membranes and Integral Inlet and Outlet Tubes for Patient Heat Exchange System" file history of related U.S. Appl. No. 14/180,655, filed Feb. 14, 2014.
Pistor et al.,"Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016.
Pistor et al., "Fluid Cassette With Polymeric Membranes and Integral Inlet and Outlet Tubes for Patient Heat Exchange System", related U.S. Appl. No. 14/180,655, Final Office dated Sep. 8, 2016.
Pistor et al., "Fluid Cassette with Polymeric Membranes and Integral Intel and Outlet Tubes for Patient Heat Exchange System", related pending U.S. Appl. No. 14/180,655, non-final office action dated May 18, 2016.
Wittman-Regis, "Written Opinion of the International Searching Authority", dated Oct. 12, 2017, from counterpart PCT application PCT/US2016/025030.
Extended European Search Report in Application No. 18747175.0, dated Oct. 29, 2020, 10 pages.

* cited by examiner

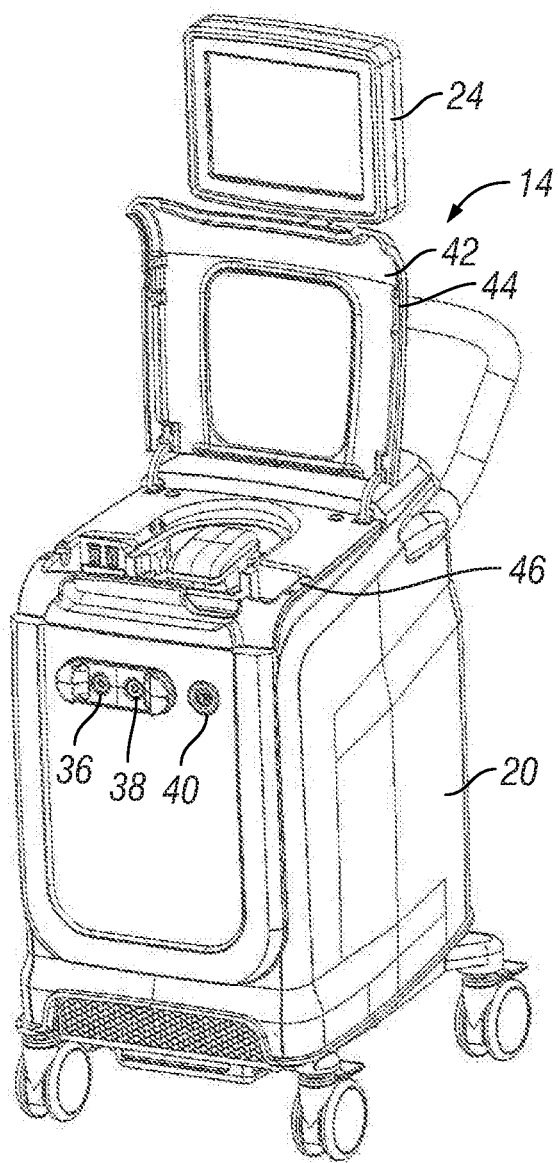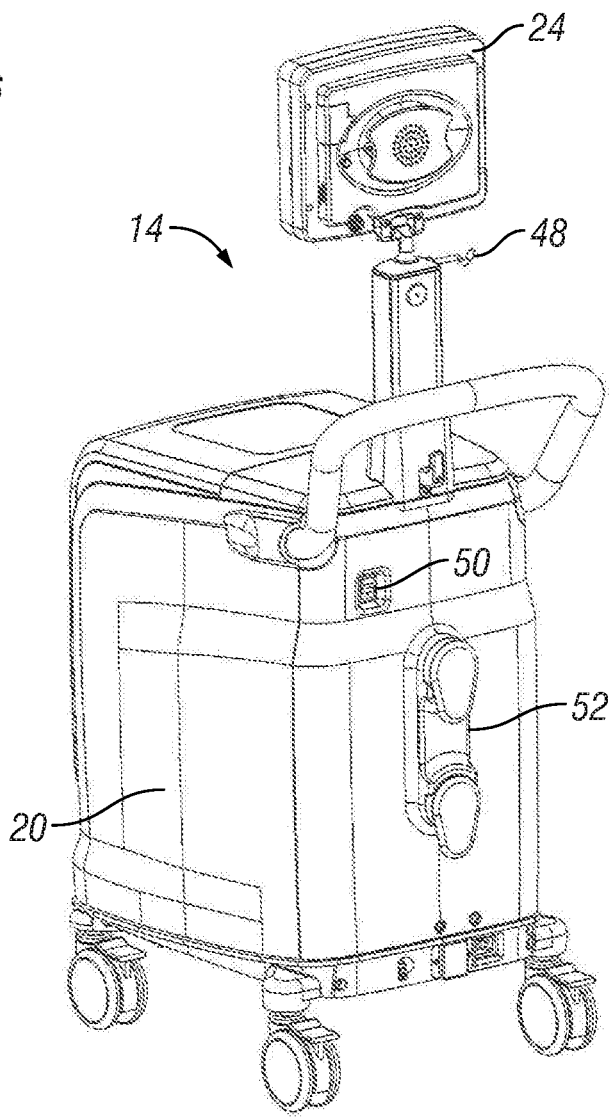
FIG. 2A
FIG. 2B

DEVICES, SYSTEMS AND METHODS FOR ENDOVASCULAR TEMPERATURE CONTROL

FIELD OF THE INVENTION

The present disclosure relates generally to the fields of medicine and engineering and more particularly to devices, systems and methods for controlling a patient's body temperature by endovascular heat exchange.

BACKGROUND

Pursuant to 37 CFR 1.71(e), this patent document contains material which is subject to copyright protection and the owner of this patent document reserves all copyright rights whatsoever.

In various clinical situations, it is desirable to warm, cool or otherwise control the body temperature of a subject. For example, hypothermia can be induced in humans and some animals for the purpose of protecting various organs and tissues (e.g., heart, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), post-anoxic coma after cardiopulmonary resuscitation, traumatic brain injury, stroke, subarachnoid hemorrhage, fever and neurological injury. Also, studies have shown that whole body hypothermia can ameliorate the toxic effects of radiographic contrast media on the kidneys (e.g., radiocontrast nephropathy) of patients with pre-existing renal impairment who undergo angiography procedures.

One method for inducing hypothermia is by endovascular temperature management (ETM) wherein a heat exchange catheter is inserted into a blood vessel and a thermal exchange fluid is circulated through a heat exchanger positioned on the portion of the catheter that is inserted in the blood vessel. As the thermal exchange fluid circulates through the catheter's heat exchanger, it exchanges heat with blood flowing past the heat exchange in the blood vessel. Such technique can be used to cool the subject's flowing blood thereby resulting in a lowering of the subject's core body temperature to some desired target temperature. ETM is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

SUMMARY

In accordance with the present disclosure, there are provided heat exchange devices, systems and methods which facilitate efficient endovascular and/or body surface heat exchange.

In accordance with one embodiment, there is provided a system for circulating a warmed or cooled thermal exchange fluid through an endovascular heat exchanger (e.g., an endovascular heat exchange catheter), wherein a) the system produces a pulsatile flow of thermal exchange fluid and b) the system is connected to the endovascular heat exchanger by way of one or more conduits which comprise a pulse damping conduit that functions not only as a conduit through which the thermal exchange fluid flows but also a pulse damper for damping pulses or pressure in the thermal exchange fluid as it flows therethrough. The pulse damping conduit may comprise, for example, tubing that has sufficient elastic or flexural properties to dampen or reduce the amplitude of pulses in the thermal exchange fluid as it flows therethrough.

In accordance with another embodiment, there is provided a system for warming or cooling the body of a human or animal subject, such system comprising an extracorporeal control system that is connectable to one or more changeable component(s) (e.g., an endovascular heat exchange catheter, a body surface heat exchange pad, tubing, a cassette through which thermal exchange fluid circulates, other disposable components, etc.). When the changeable component(s) is/are connected to the extracorporeal control system, the system is useable to effect heat exchange with the subject's body. The changeable component(s) may include machine readable encoded information. The extracorporeal control system includes a reader that receives and reads the encoded information. The extracorporeal control system uses such encoded information to identify, qualify, confirm or control the operation of the changeable component(s). The encoded information may be stored in any suitable electronic storage medium and may be embedded in a chip or microchip mounted on or in the changeable component(s). Examples of the types of encoded information that may be stored include but are not limited to; unique identifier(s) for the changeable components (e.g., manufacturer identification, part number, lot number, etc.), indications of whether the changeable component(s) have previously been used (e.g., an encoded indication of first use), indications of whether the changeable component(s) is/are expired (e.g., encoded expiration date), operational characteristic(s) of the changeable component(s) (e.g., encoded indications of the size, type, volume, etc. of the changeable component(s). Examples of the types of information storage that may be utilized include but are not necessarily limited to: non-volatile random access memory (RAM), non-volatile flash memory, electrically erasable programmable read-only memory (EEPROM) or ferroelectric random access memory (FRAM). The extracorporeal control system may comprises a controller (e.g., a processor) programmed to take one or more actions in response to the encoded information. For example, the controller may be programmed to determine whether the encoded information meets a prerequisite requirement and to proceed with warming or cooling of the subject's body only if said prerequisite requirement is met.

In accordance with another embodiment, there is provided a thermal exchange engine for warming or cooling a thermal exchange fluid. Such thermal exchange engine comprises thermal exchange plates or evaporators which are alternately coolable by circulation of refrigerant through the plates and warmable by heaters positioned on or in the plates. A cassette receiving space is located between the temperature controlled plates and is configured for receiving a cassette or heat exchanger. The cassette comprises a frame and an expandable vessel (e.g., a bag or other expandable fluid containing vessel). The expandable vessel is fillable with thermal exchange fluid, e.g., after the cassette has been inserted into the cassette receiving space. Heat is thereby transferred between the refrigerant and the thermal exchange fluid or the heater(s) and the thermal exchange fluid. In some embodiments, outer surface(s) of the expandable vessel may be coated with a release material, covered with a layer of releasable material or otherwise treated or modified to deter sticking of the expandable vessel to the adjacent thermal exchange plates. In some embodiments, surface(s) of the thermal exchange plates and/or surfaces of the expandable vessel or a layer on a surface of the expandable vessel may be textured or provided with holes, groves or other surface features to deter sticking of the expandable vessel to the adjacent thermal exchange plates. In some embodiments, the cassette may comprise a housing attached to an insertable portion (e.g., the frame and expandable vessel) by a hinged attachment such that the cassette may be disposed in a folded or closed configuration prior to use and converted to an unfolded or open configuration at the time of use. Such hinged connection between the housing and the insertable portion may be constructed so that, once unfolded or opened, the cassette locks in the unfolded or open configuration. In some embodiments, a plurality of hooks located in the console or system may be initially positioned in retracted positions allowing insertion of the insertable portion into the cassette receiving space between the thermal exchange plates and, thereafter, may be moved to advanced positions wherein they hold the insertable portion of the cassette within the cassette receiving space.

In accordance with another embodiment, there is provided a system configured to circulate warmed or cooled thermal exchange fluid through a body heat exchanger to warm or cool the body or a human or animal subject, wherein the system comprises a first display device which receives signals from one or more temperature sensors and displays temperature data based on signals received from said one or more temperature sensors. The first display device is connectable, by wired or wireless connectivity, to a second display device (e.g., a bedside monitor, central unit monitor, remote monitor, etc.), so as to transmit said signals received from said one or more temperature sensors from the first display device to the second display device. The system further comprises circuitry for minimizing or eliminating any effect of ambient temperature on such signals as they are transmitted from the first display device to the second display device. In some embodiments, the signals transmitted from the first display device to the second display device may comprise signals representative of sensed temperatures, such as patient body temperature, temperature of thermal exchange fluid flowing to the body heat exchanger, temperature of thermal exchange fluid flowing from the body heat exchanger, etc.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

FIG. 2A is a left/front perspective view of the control console with its access cover in an open position.

FIG. 2B is a left/rear perspective view of the control console.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1:
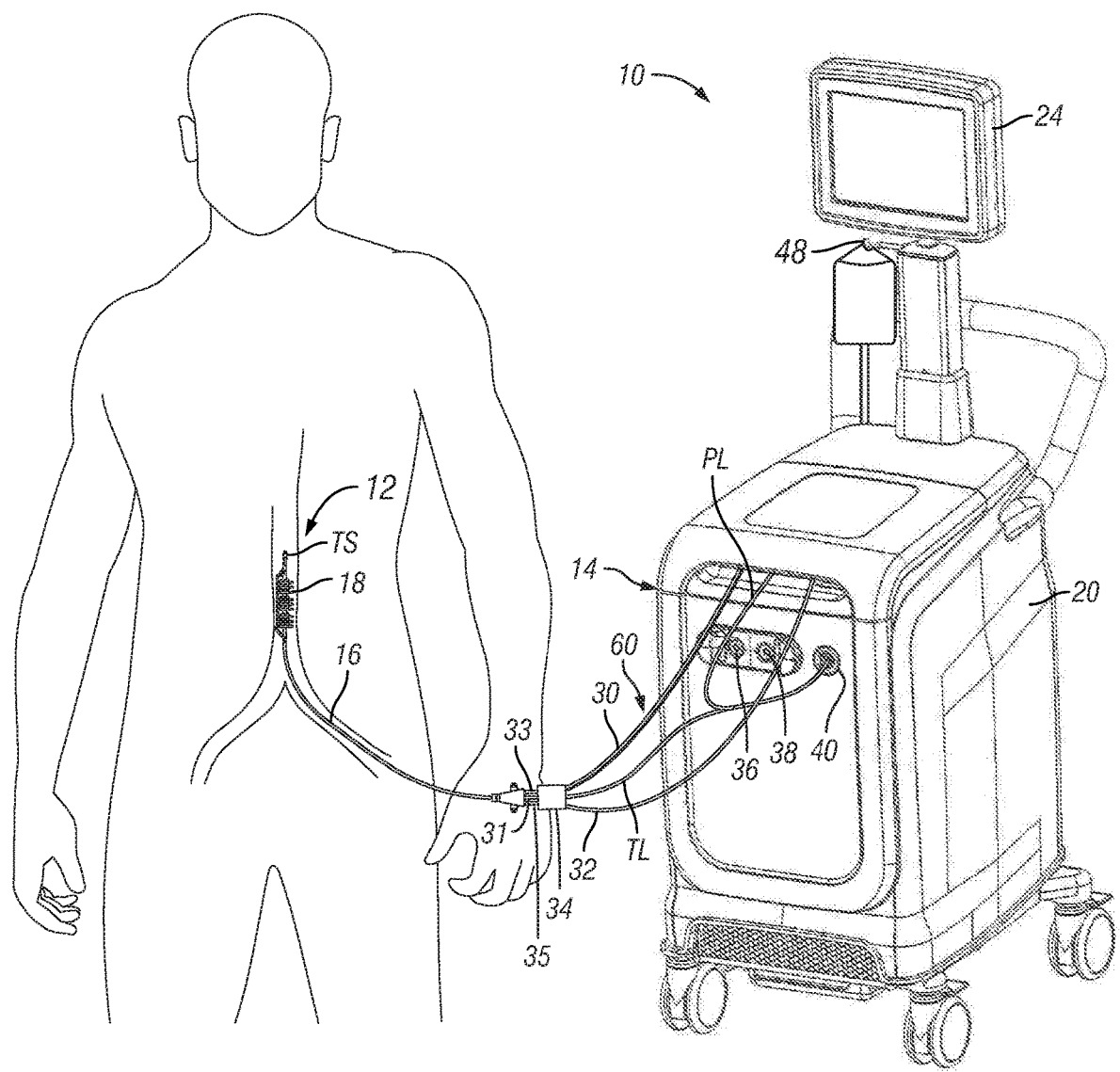
FIG. 1 shows one embodiment of an endovascular heat exchange system comprising an endovascular heat exchange catheter, an extracorporeal control console and a tubing/cassette/sensor module assembly useable for operatively connecting the heat exchange catheter to the control console.

FIG. 1 shows one embodiment of an endovascular heat exchange system 10 in operation to control the body temperature of a human subject. This endovascular heat exchange system 10 generally comprises an endovascular heat exchange catheter 12, an extracorporeal control console 14, a tubing/cassette/sensor module assembly 60 or cassette assembly which facilitates connection of the catheter 12 to the control console 14 and a temperature sensor TS. In at least some embodiments, the catheter 12, tubing/cassette/sensor module assembly 60 or cassette assembly and temperature sensor TS may be disposable items intended for a single use, while the control console 14 may be a non-disposable device intended for multiple uses.

In the embodiment shown, the endovascular heat exchange catheter 12 comprises an elongate catheter body 16 and a heat exchanger 18 positioned on a distal portion of the catheter body 16. Inflow and outflow lumens (not shown) are present within the catheter body 16 to facilitate circulation of a thermal exchange fluid (e.g., sterile 0.9% sodium chloride solution or other suitable thermal exchange fluid) through the heat exchanger 18. Optionally, the catheter shaft 16 may also include a working lumen (not shown) which extends through the catheter body 16 and terminates distally at an opening in the distal end of the catheter body 16. Such working lumen may serve as a guidewire lumen to facilitate insertion and position of the catheter 12 and/or may be used after insertion of the catheter 12 for delivery of fluids, medicaments or other devices. For example, as shown in FIG. 1, in some embodiments, the temperature sensor TS may be inserted through the catheter's working lumen and advanced out of the distal end opening to a location beyond the distal end of the catheter body 16. Alternatively, in other embodiments, the temperature sensor TS may be positioned at various other locations on or in the subject's body to sense the desired body temperature(s). Various heat exchange catheters may be used in the embodiments described herein. Non-limiting examples of heat exchange catheters and related apparatus that may be used are described in U.S. Pat. No. 9,492,633, and United States Patent Application Publications Nos. 2013/0090708, 2013/0178923, 2013/0079855, 2013/0079856, 2014/0094880, 2014/0094882, 2014/0094883, and unpublished, copending U.S. patent application Ser. Nos. 15/395,858, 15/395,923 and 15/412,390, the entire disclosure of each such patent and application being expressly incorporated herein by reference. Other examples of catheters that may be used in this invention include those commercially available from ZOLL Circulation, Inc., San Jose, Calif., such as the Cool Line® Catheter, Icy® Catheter, Quattro® Catheter, Solex 7® Catheter, InnerCool® RTx Accutrol Catheter and the InnerCool RTx Standard Catheter.

The extracorporeal control console 14 generally comprises a main housing 20 and a console head 24. As described in detail herebelow, the main housing 20 contains various apparatus and circuitry for warming/cooling thermal exchange fluid to controlled temperature(s) and for pumping such warmed or cooled thermal exchange fluid through the catheter 18 to effectively modify and/or control the subject's body temperature. The console head 24 comprises a display device or user interface, such as a touch screen system, whereby certain information may be input by, and certain information may be displayed to, users of the system 10. On the housing 20 there are provided a first connection port 40 for connection of a temperature sensor TS that is inserted through the heat exchange catheter 12 as shown in FIG. 1 as well as other connection ports 36, 38 for connection of additional or alternative types of temperature sensors and/or other apparatus.

Figure 3:
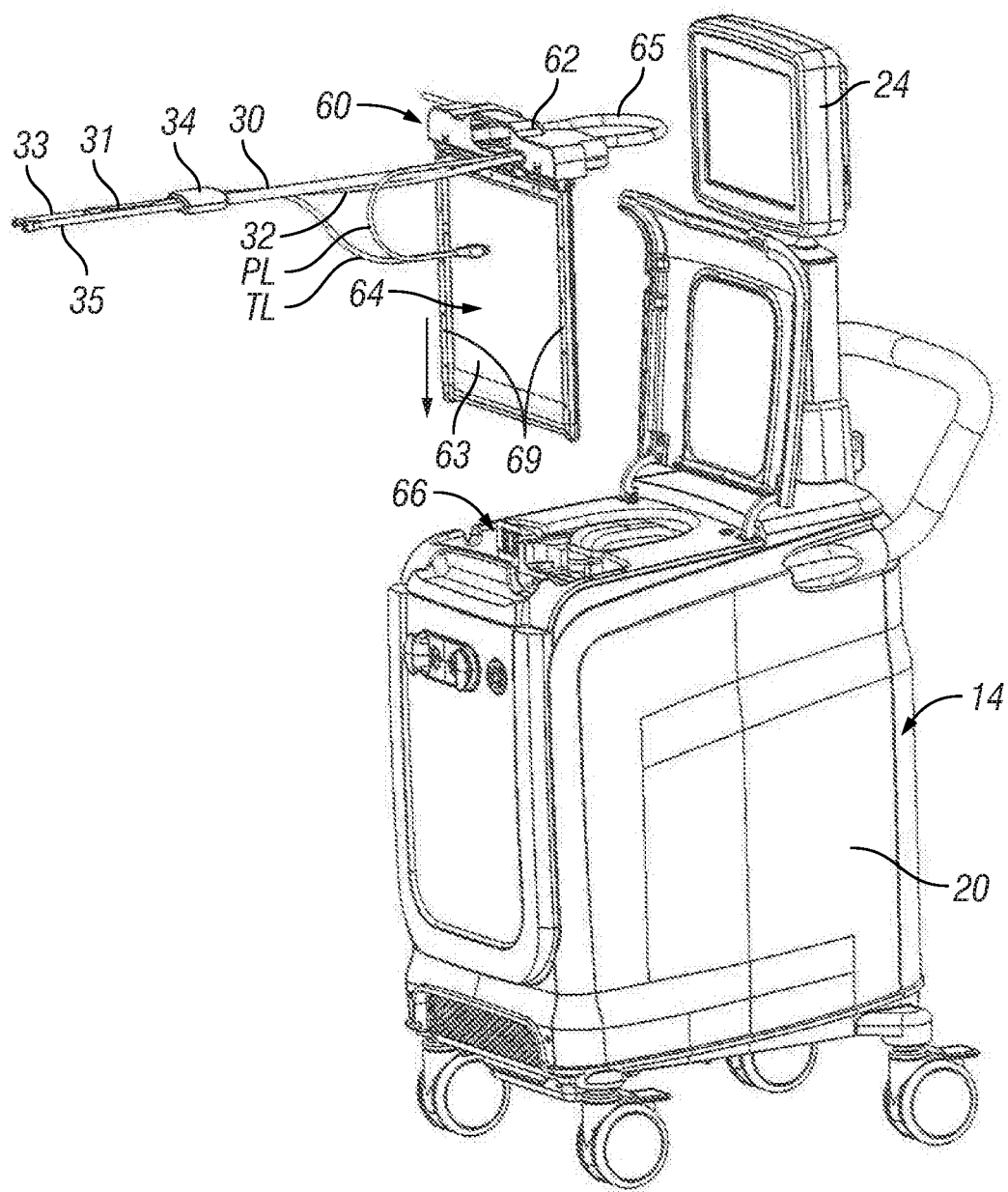
FIG. 3 is an exploded view of the control console with its access cover in an open position and the tubing/cassette/sensor module assembly staged for insertion in, and operative connection to, the control console.
Figure 4:
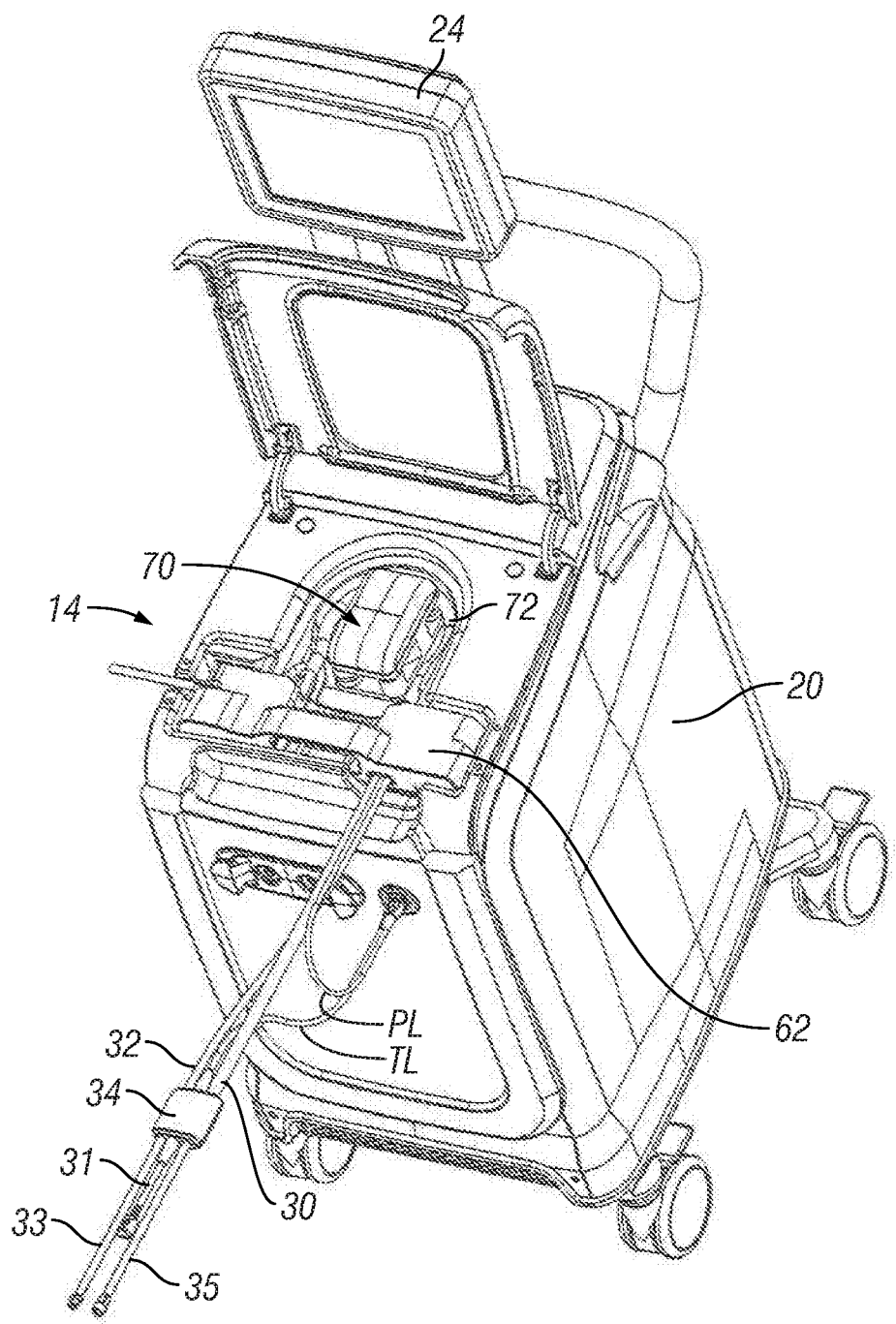
FIG. 4 is a top (perspective) view of the control console with its access cover in an open position and the tubing/cassette/sensor module assembly operatively inserted in and connected to the control console.
Figure 5:
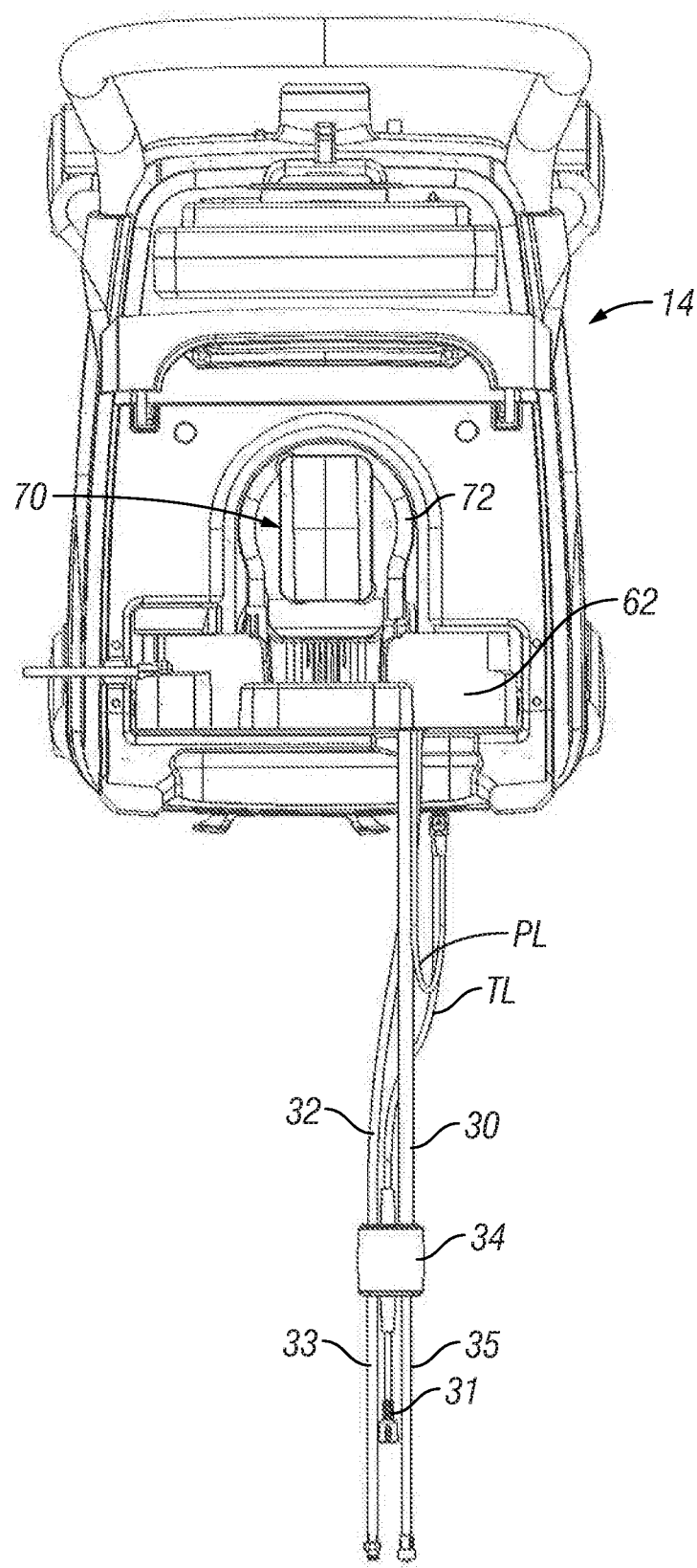
FIG. 5 is a top (plan) view of the control console with its access cover in an open position and the tubing/cassette/sensor module assembly operatively inserted in and connected to the control console.
Figure 6:
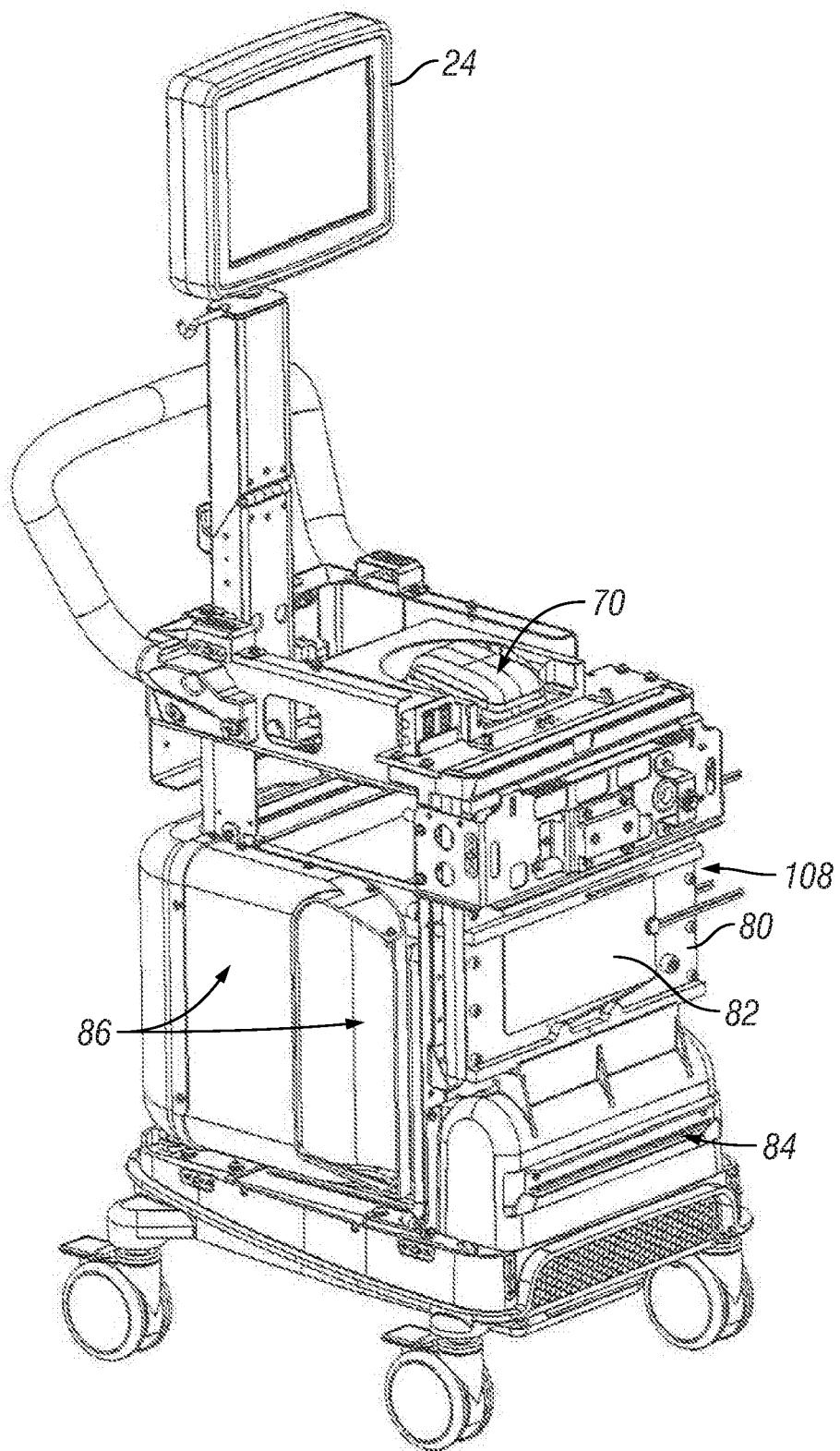
FIG. 6 is a right/front perspective view of the control console with its housing and access cover removed.
Figure 7:
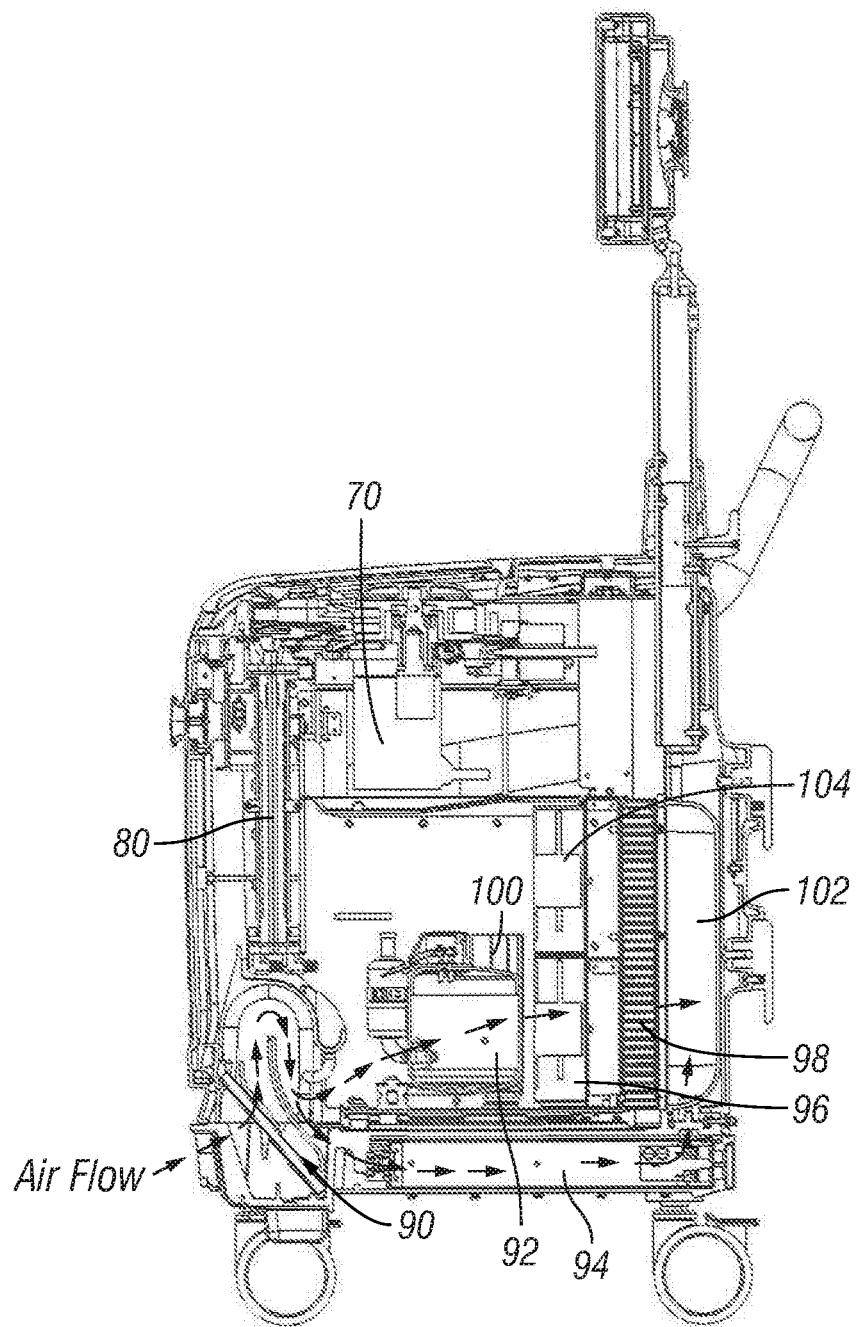
FIG. 7 is a left cross-sectional view of the control console.
Figure 8:
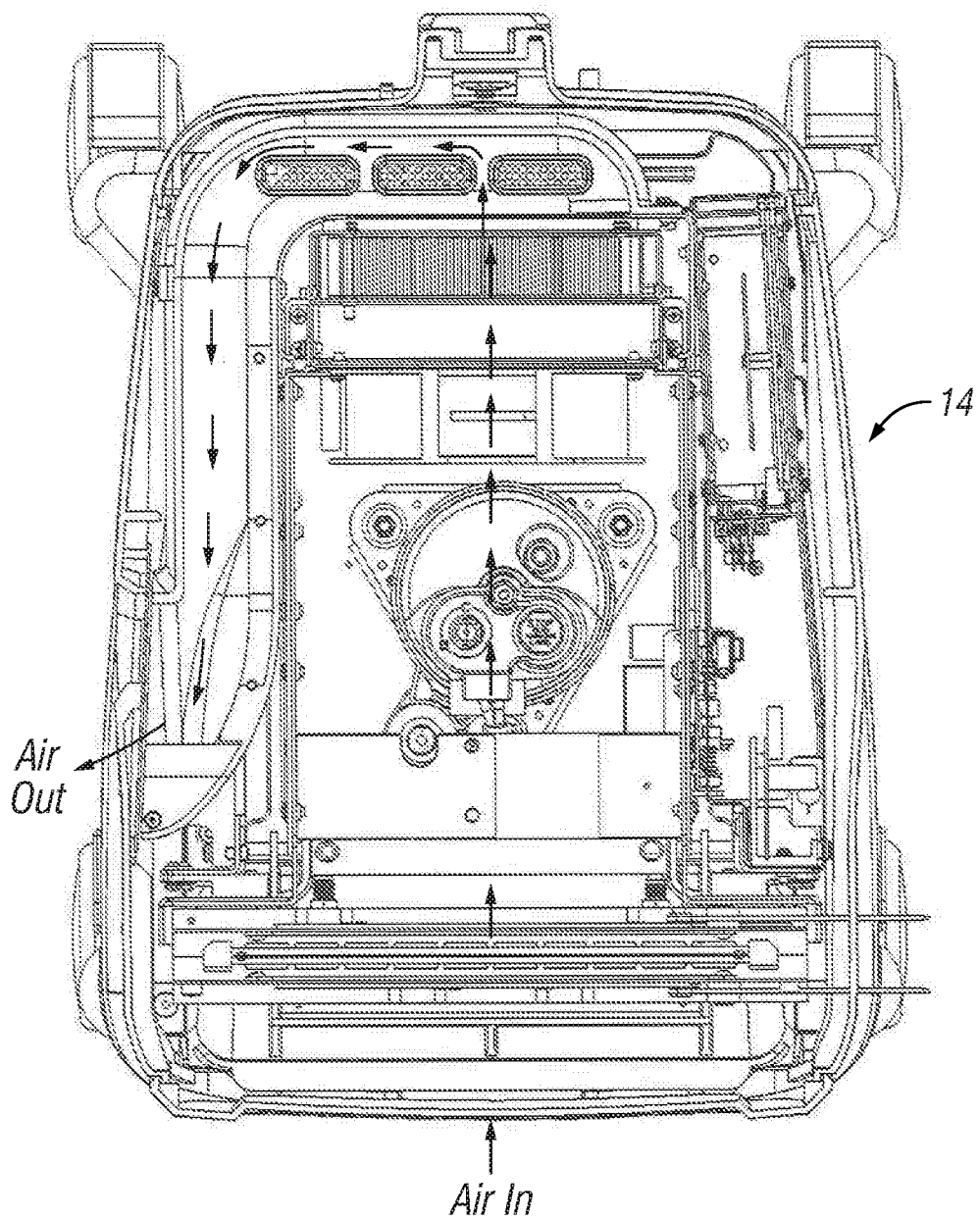
FIG. 8 is a top cross-sectional view of the control console.
Figure 9:
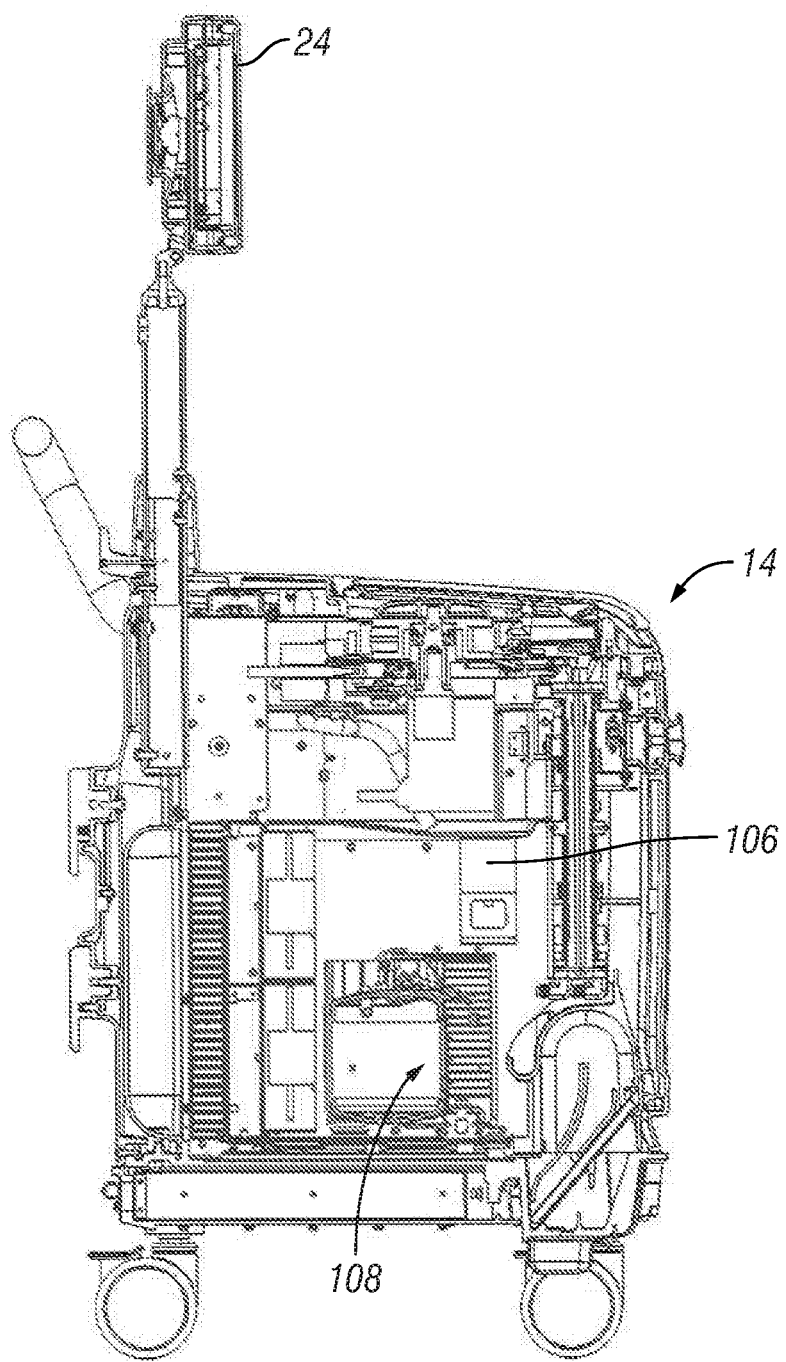
FIG. 9 is a right cross-sectional view of the control console.
Figure 10:
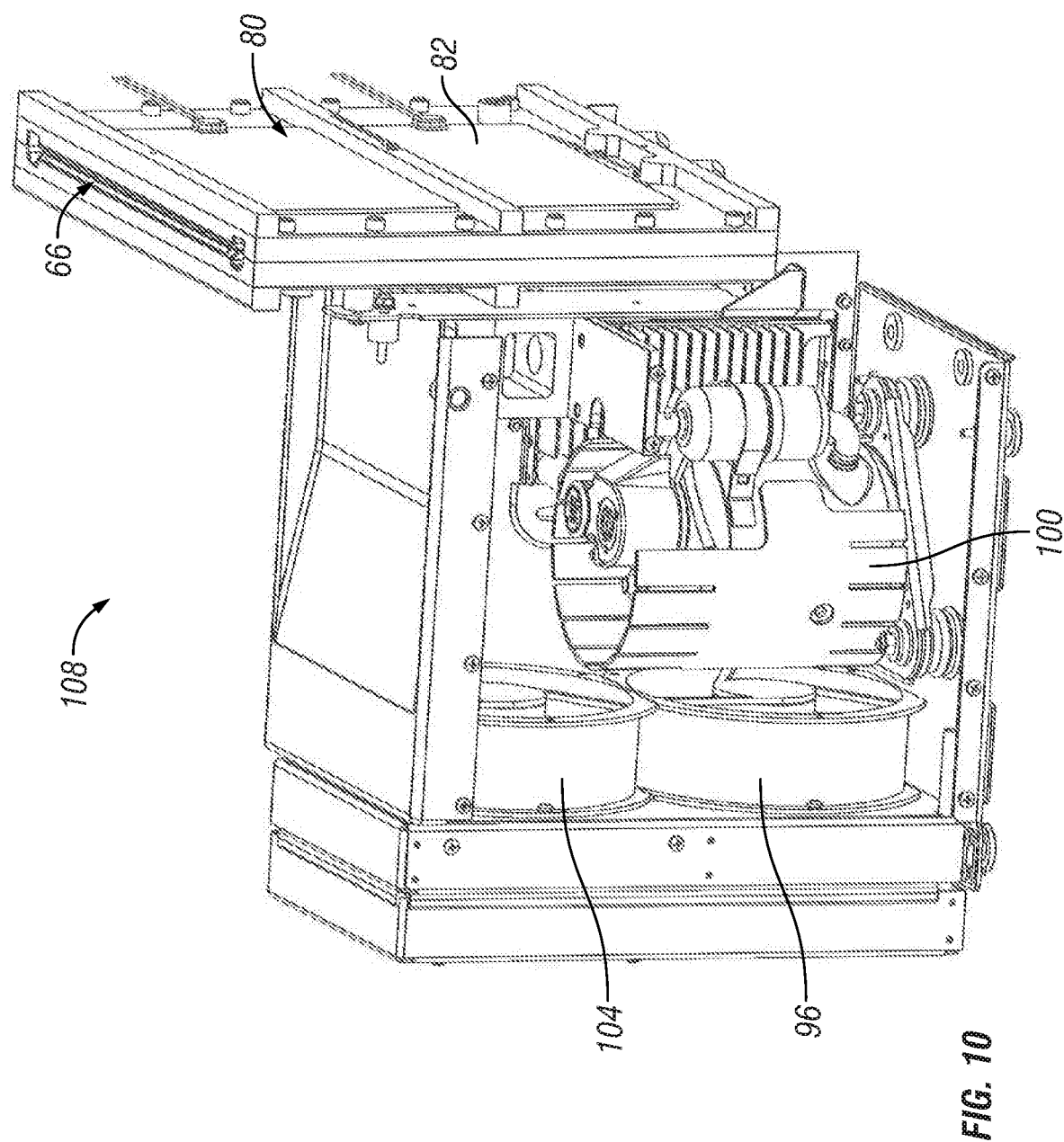
FIG. 10 is a perspective view of a thermal exchange engine component of the control console.
Figure 11:
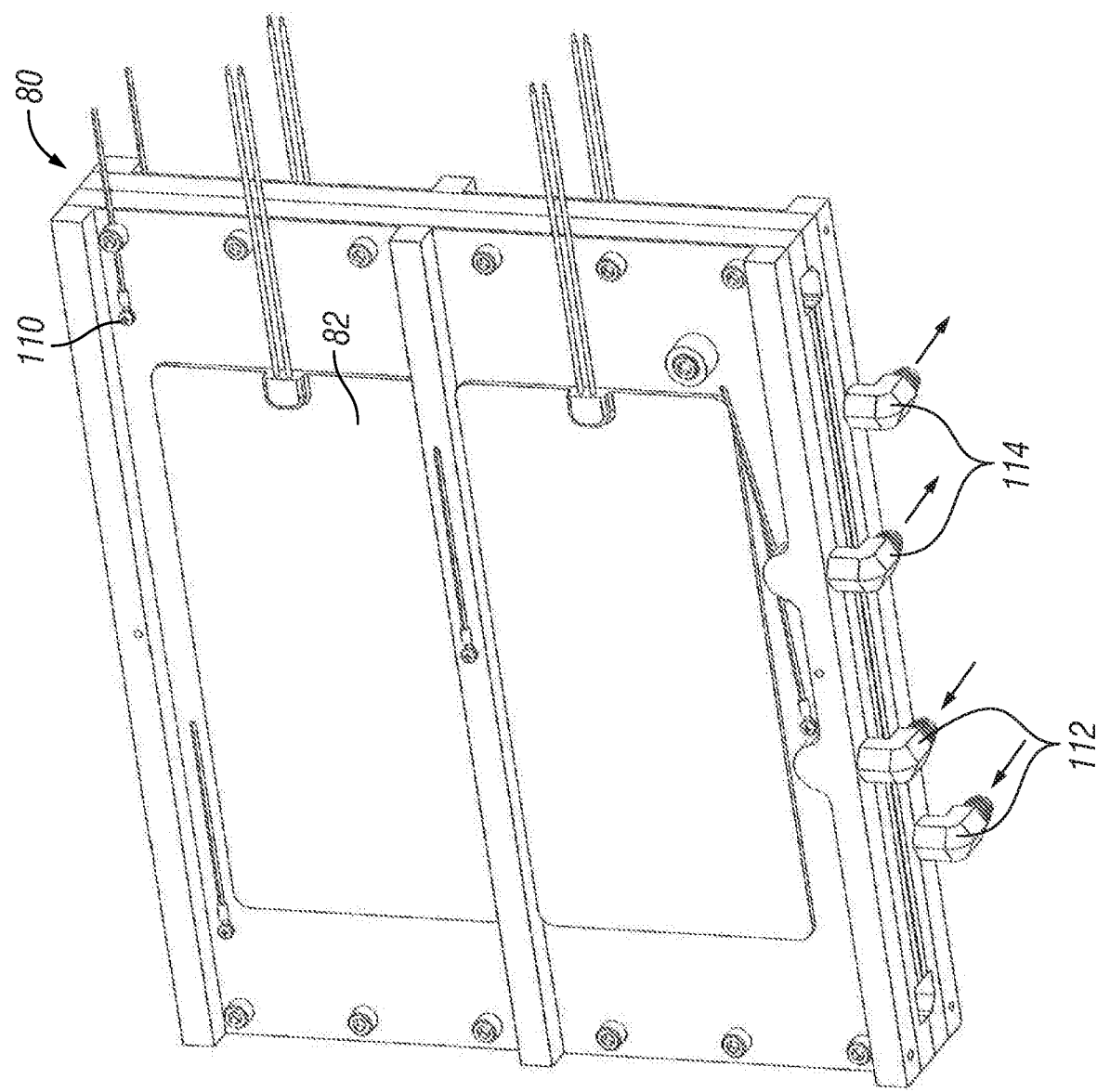
FIG. 11 is a bottom/perspective view of a thermal exchange plate assembly of the thermal exchange engine.
Figure 12:
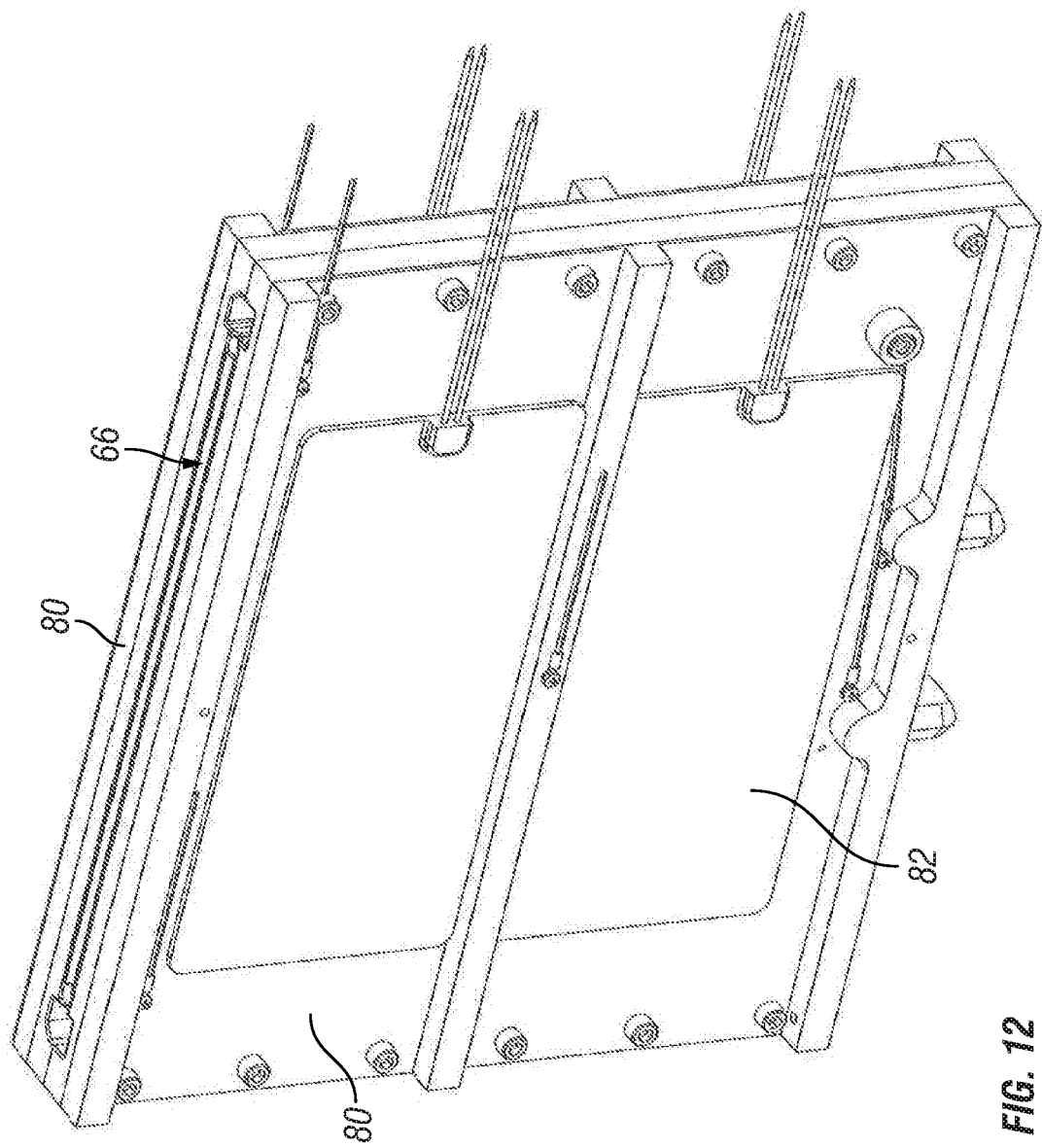
FIG. 12 is a top/perspective view of the thermal exchange plate assembly.
Figure 13:
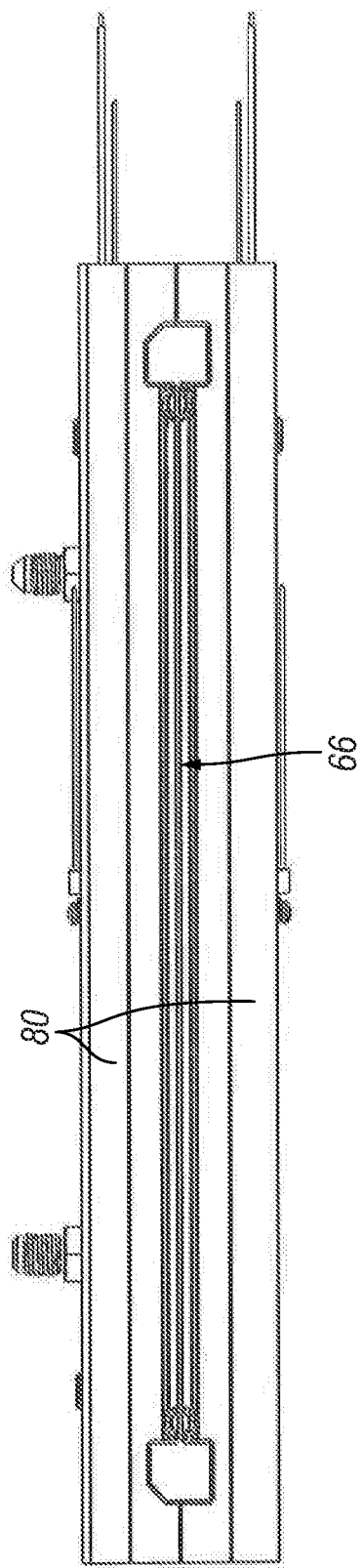
FIG. 13 is a top (plan) view of the thermal exchange plate assembly of the thermal exchange engine.
Figure 14:
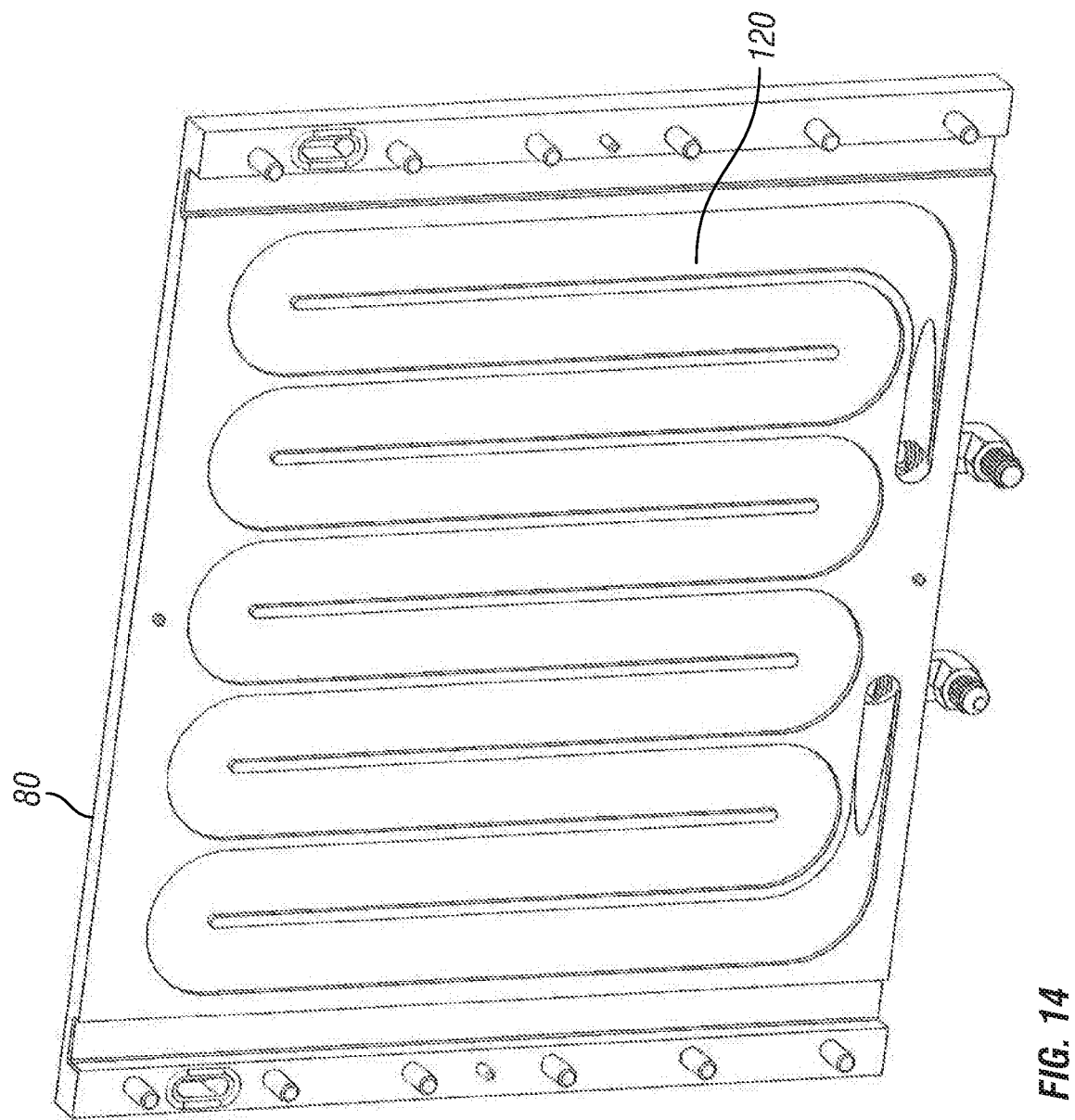
FIG. 14 is disassembled view of one of the thermal exchange plates of the thermal exchange plate assembly, exposing a vertically oriented serpentine refrigerant flow path formed in the inner surface of the plate.

The tubing/cassette/sensor module assembly 60 or cassette assembly, which is seen in further detail in FIGS. 3-5, generally comprises a sensor module 34, an inflow conduit 32, inflow connector 33, outflow conduit 30, outflow connector 31, temperature lead TL, temperature lead connector 35, pressure lead PL, cassette 64, cassette housing 62 and peristaltic pump tubing 65.

FIGS. 2A through 9 show further detail of the components within the housing 20 and the manner in which the tubing/cassette/sensor module assembly 60 or cassette assembly is inserted in and connected to the control console 14. As seen in FIGS. 2A through 3, the control console 14 has an openable/closable access cover 42 which, when opened, permits insertion of the cassette 64 into a cassette receiving space 66 as well as other connection of the tubing/cassette/sensor module assembly 60 or cassette assembly to other components of the system described below. A magnet 44 on the access cover 42 interacts with a magnetic sensor 46 to emit signal(s) indicating whether the access cover 42 is opened or closed. Other sensors and detection mechanisms known to persons having skill in the art may be utilized as well. The system controller located in the housing 20 may be programmed to halt running of certain components of the system when the access cover 44 is opened. On the rear of the housing 20, there is provided a power switch 50 and a power cord holder 52. A bracket 48 is provided on an upstanding portion of the housing which supports the console head 24 for hanging a bag or container of fluid.

As seen in FIGS. 3 through 5, with the access cover 42 in an open position, the cassette 64 is insertable downwardly into the cassette receiving space 66 and the pump tubing 65 is insertable into a tubing raceway 72 of pump 70.

FIGS. 6 through 10 provide partially disassembled and sectional views which reveal various components of the control console 14. The thermal exchange engine 108, includes a refrigeration system which comprises a compressor 92, stepper motor for turning an expansion valve 106, fans 96 and 104, condenser 98 and compressor heat sink 100. The heat sink may be a metallic, e.g., aluminum, cylindrical enclosure that surrounds the compressor. The heat sink is in contact with the compressor and increases the surface area of the compressor to facilitate enhances removal of heat from the compressor. The thermal exchange system is powered by power supply 94. Thermal exchange plates 80, are provided to alternately warm or cool thermal exchange fluid as it circulates through a cassette 64 that has been inserted in the cassette receiving space 66 between the thermal exchange plates. Resistance heaters 82 are mounted on the plates 80 for warming the plates 80 when operating in a warming mode and a refrigerant, such as Refrigerant R143a (1,1,1,2 Tetrafluoroethane) is compressed by the compressor 92 and circulated through the condenser 98 and plates 80 to cool the plates when operating in a cooling mode. In certain embodiments, heaters may include a thermal cutout switch for automatically turning one or more of the heaters off if the heaters were to overheat.

When operating in a cooling mode, the thermal exchange engine 108 emits heat. Fans 96 and 104 circulate air through air plenums or spaces adjacent to the thermal exchange engine 108 and over surfaces of the compressor and compressor heat sink 100 to exhaust emitted heat and maintain the thermal exchange engine 108 at a suitable operating temperature. Specifically, in the embodiment shown, air enters air intake 84 through filter 90, circulates through the device as indicated by arrows on FIGS. 7 and 8, and is exhausted through an air outlet or exhaust vent on a side of the console 14 as shown specifically in FIG. 8. The airflow pathway is specifically configured to minimize the amount of sound that escapes from the system via the airflow pathway and is audible to a user or patient. The airflow pathway includes a convoluted pathway or channels which provide reflective surfaces to contain the acoustic energy within the cooling engine enclosure. Also, the interior of the intake and exhaust ducts and pathway or channels are lined with an acoustically absorbent material, e.g., open-celled elastomeric foam. The combination of these features minimizes the amount of sound, such as that generated by the fans and compressor, that escapes the system. For example, in certain embodiments, the operating noise level of a system may not exceed 65 dBA measured at a distance of 1 m from the system when the system is in maximum cooling and 58 dBA measured at a distance of 1 m from the system when the system is in maintenance or warming.

The structure and function of the thermal exchange plates may be appreciated in further detail in FIGS. 11 through 17. Thermal exchange plates 80 may be positioned on either side of the cassette receiving space 66. The thermal exchange plates are connected on their ends forming a cassette receiving space or slot between the plates. The thermal exchange plates may be referred to as a thermal exchange plate assembly. Resistance heaters 82 are mounted in one or more of plates 80 and are useable to warm the plates 80 when warming of the circulating thermal exchange fluid is desired. In certain embodiments, vertically oriented, serpentine or convoluted, refrigerant flow channels 120 are formed within the plates 80. This orientation and design of the refrigerant flow channels help maximize and realize the cooling power of the cooling engine, e.g., For example, the plates are configured to evaporate the refrigerant moved by a 900 W compressor (e.g., a Masterflux compressor) within a cooling engine envelope sized to fit within the housing 20, as illustrated in the figures herein. In each plate, cold refrigerant circulates through refrigerant inlet 112, through the refrigerant flow channels 120 and out of refrigerant outlet 114. The refrigerant changes phase from a liquid substantially to a gas while flowing through the refrigerant flow channels 120, thereby cooling the plates 80. Such warming or cooling of the plates 80, in turn causes warming or cooling of thermal exchange fluid being circulated through a cassette positioned within the cassette receiving space 66. Temperature sensors 110, e.g., thermistors, may be located on the plates to detect the temperature of the plates. Signals from the temperature sensors may be fed back to the system controller or control processor to control warming and/or cooling (e.g., to prevent freezing) by the system.

Figure 15:
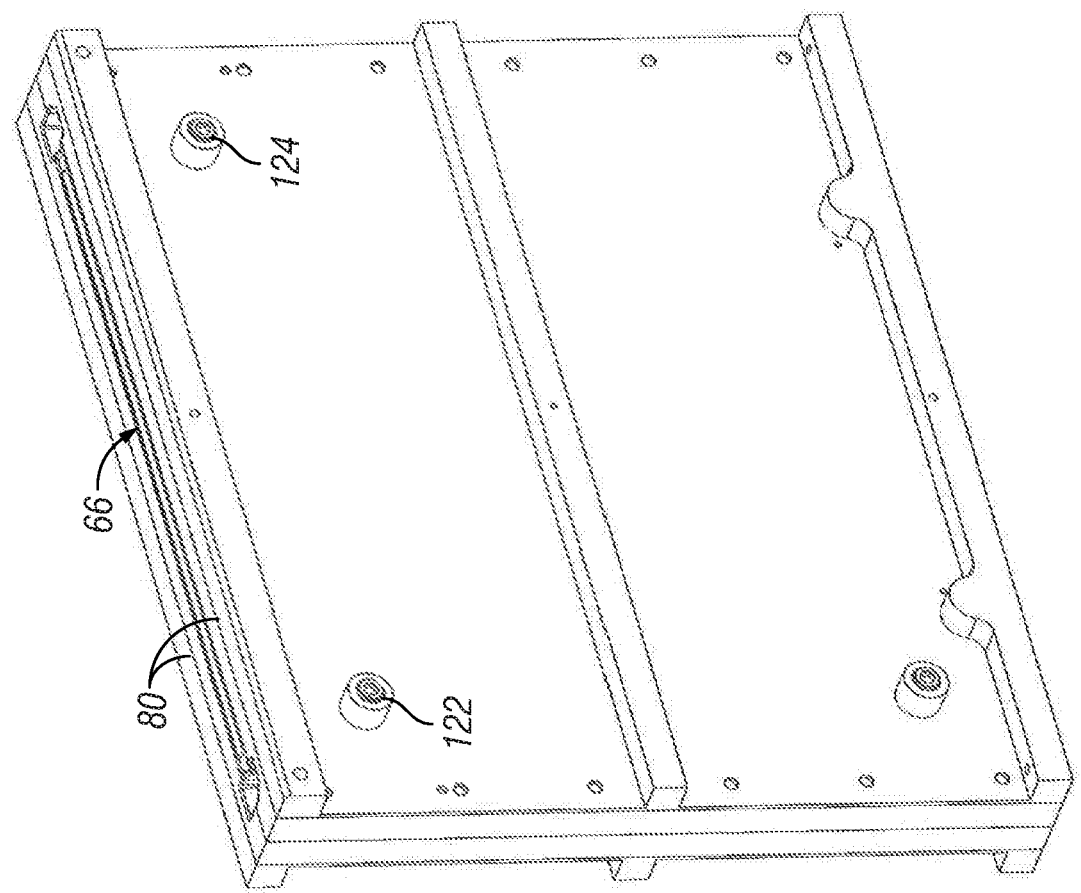
FIG. 15 is a rear view of the thermal exchange plate assembly with the outer plate and heater removed.
Figure 16:
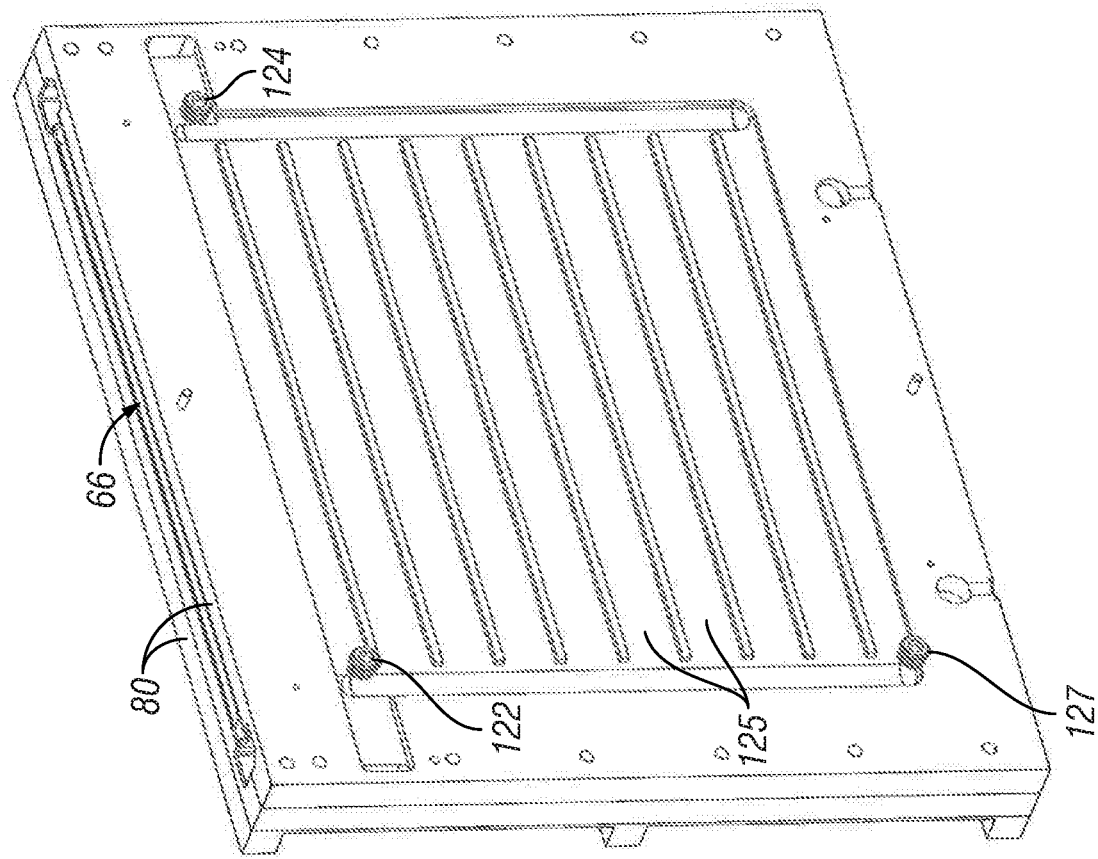
FIG. 16 is a partially disassembled rear perspective view of with the thermal exchange plate wherein rear plates have been removed so as to expose secondary fluid flow channels useable for optional non-cassette warming/cooling of a fluid.
Figure 17:
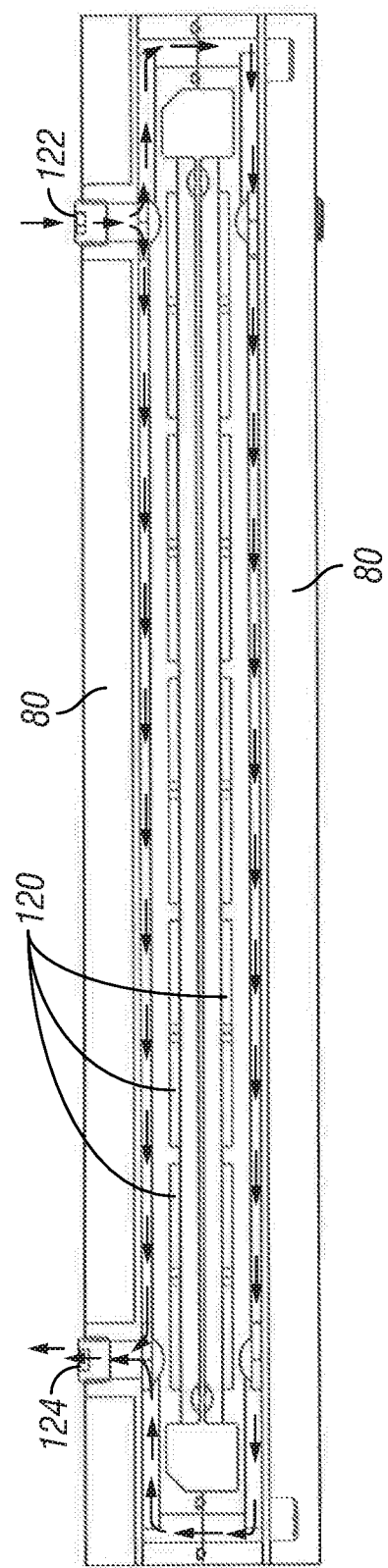
FIG. 17 is a top view of the fully assembled thermal exchange plate assembly.

Optionally, as shown in the views of FIGS. 15 and 16, the thermal exchange plates 80 may incorporate channels 125 for circulation of a thermal exchange fluid directly through the plates. For example, a desired thermal exchange fluid may circulate in inlet 122, through horizontal flow channels 125 and out of outlet 124. A single inlet port may be used to supply thermal exchange fluid to both plates as the fluid passes from a first plate to the second plate, through channels located at the ends of the thermal exchange plate assembly, and exits the thermal exchange plate assembly through a single outlet port. A drain port 127 may be provided for draining residual thermal exchange fluid or flushing debris from the flow channels 125, when required. These channels 125 may be used for cooling or warming a secondary thermal exchange fluid simultaneously with, or as an alternative to, the warming or cooling of a heat exchange fluid circulating through a cassette 64 inserted within the cassette receiving space 66. In some embodiments, the channels 125 may be configured to provide a volume flow of secondary thermal exchange fluid that differs from the volume flow of thermal exchange fluid which circulates through the cassette 64. For example, a cassette 64 may be inserted in the cassette receiving space 66 and used for circulating a relatively small volume of warmed or cooled thermal exchange fluid (e.g., sterile saline solution) through an endovascular catheter 12 and, simultaneously or alternately, the channels 125 may be used to warm or cool a larger volume of a secondary thermal exchange fluid (e.g., nonsterile water) for circulation through body surface cooling device(s) such as surface cooling pad(s), blanket(s), garment(s), etc. Further details and examples of such concurrent or separate use of endovascular and body surface temperature exchange are described in copending U.S. patent application Ser. No. 15/412,390 entitled Managing Patient Body Temperature Using Endovascular Heat Exchange in Combination With Body Surface Heat Exchange, the entire disclosure of which is expressly incorporated herein by reference.

Figure 18:
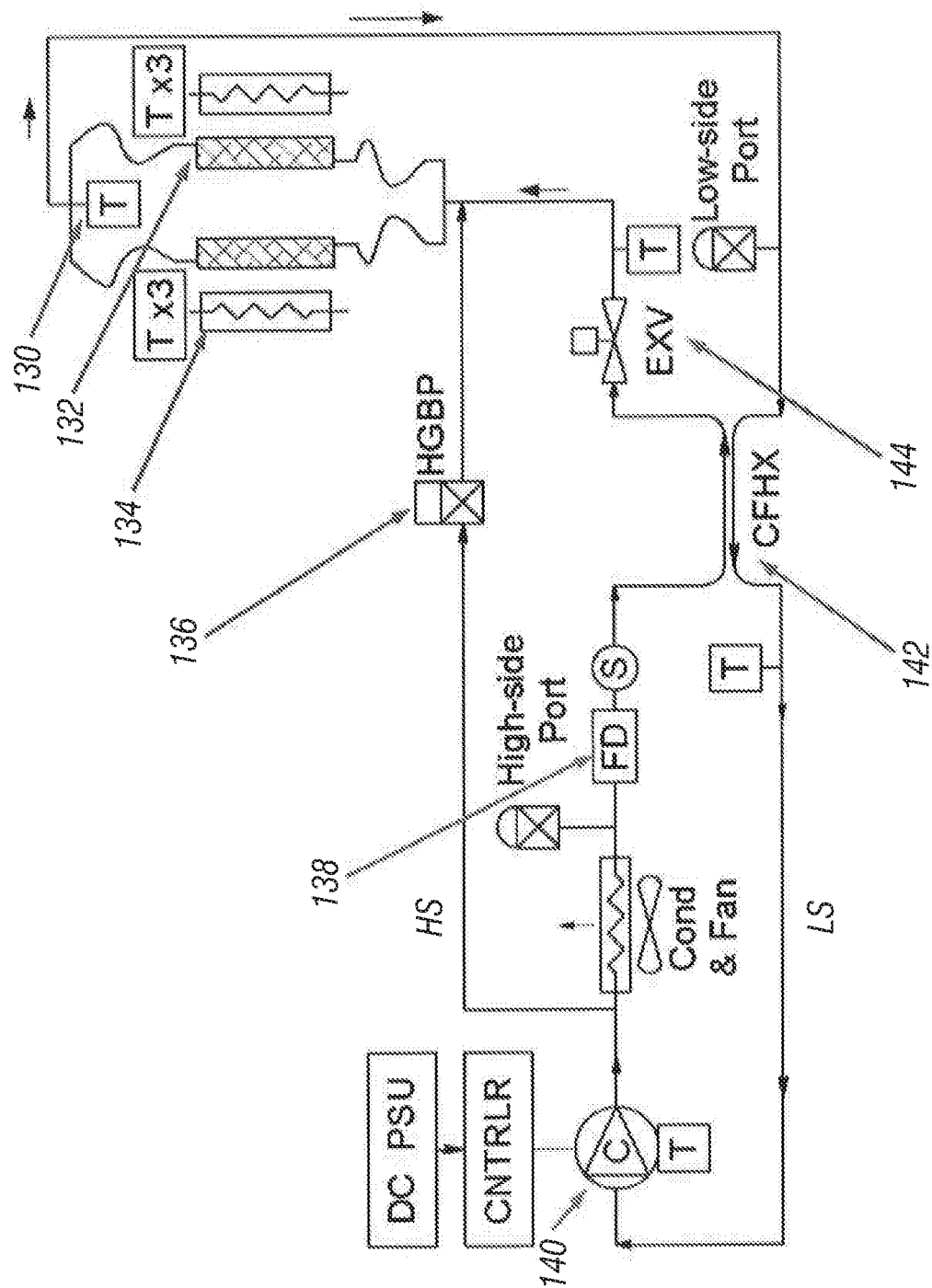
FIG. 18 is a schematic diagram illustrating the functional lay out of the thermal exchange engine.
Figure 19:
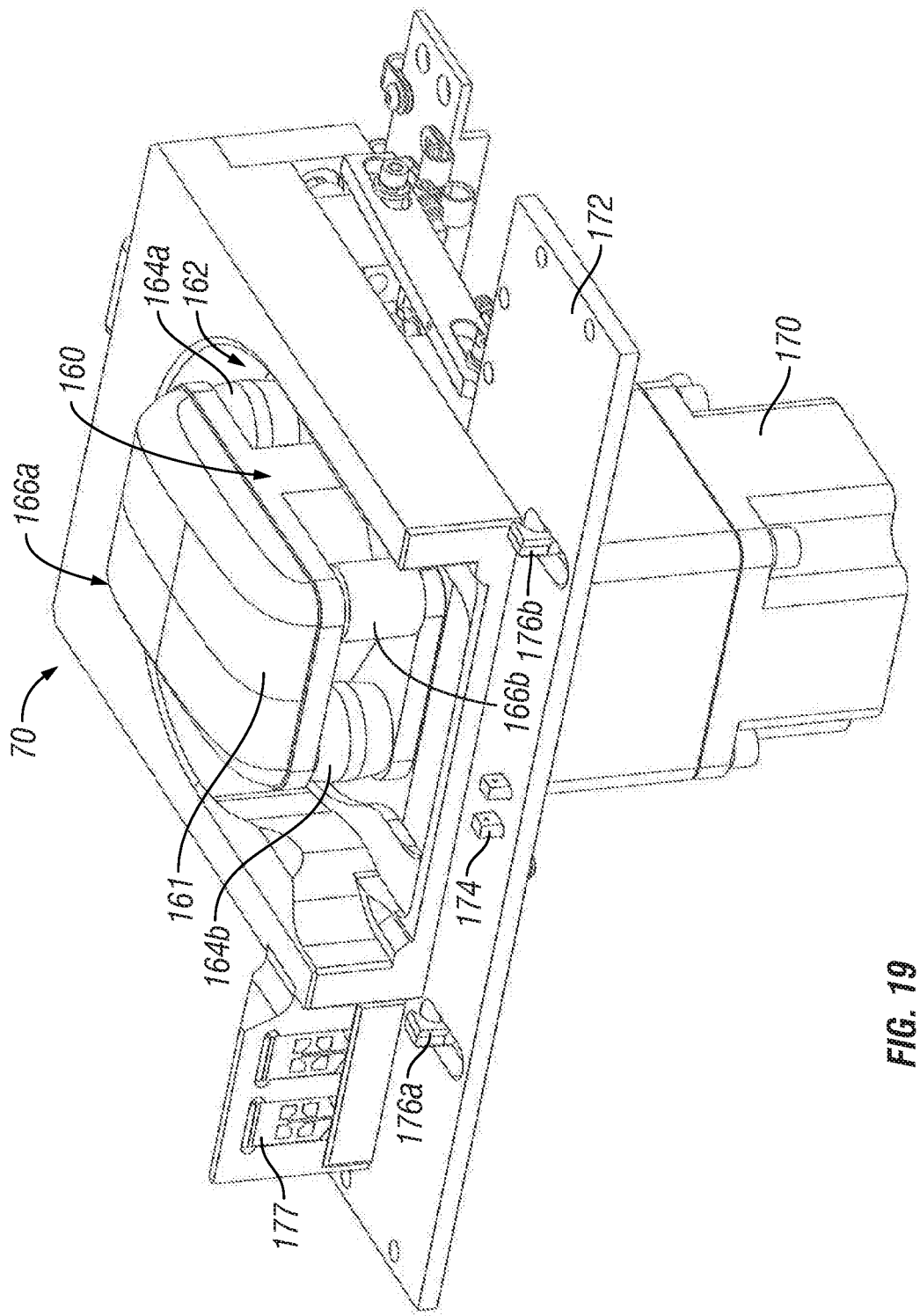
FIG. 19 is a front perspective view of the pump assembly of extracorporeal control console.
Figures 20, 20A:
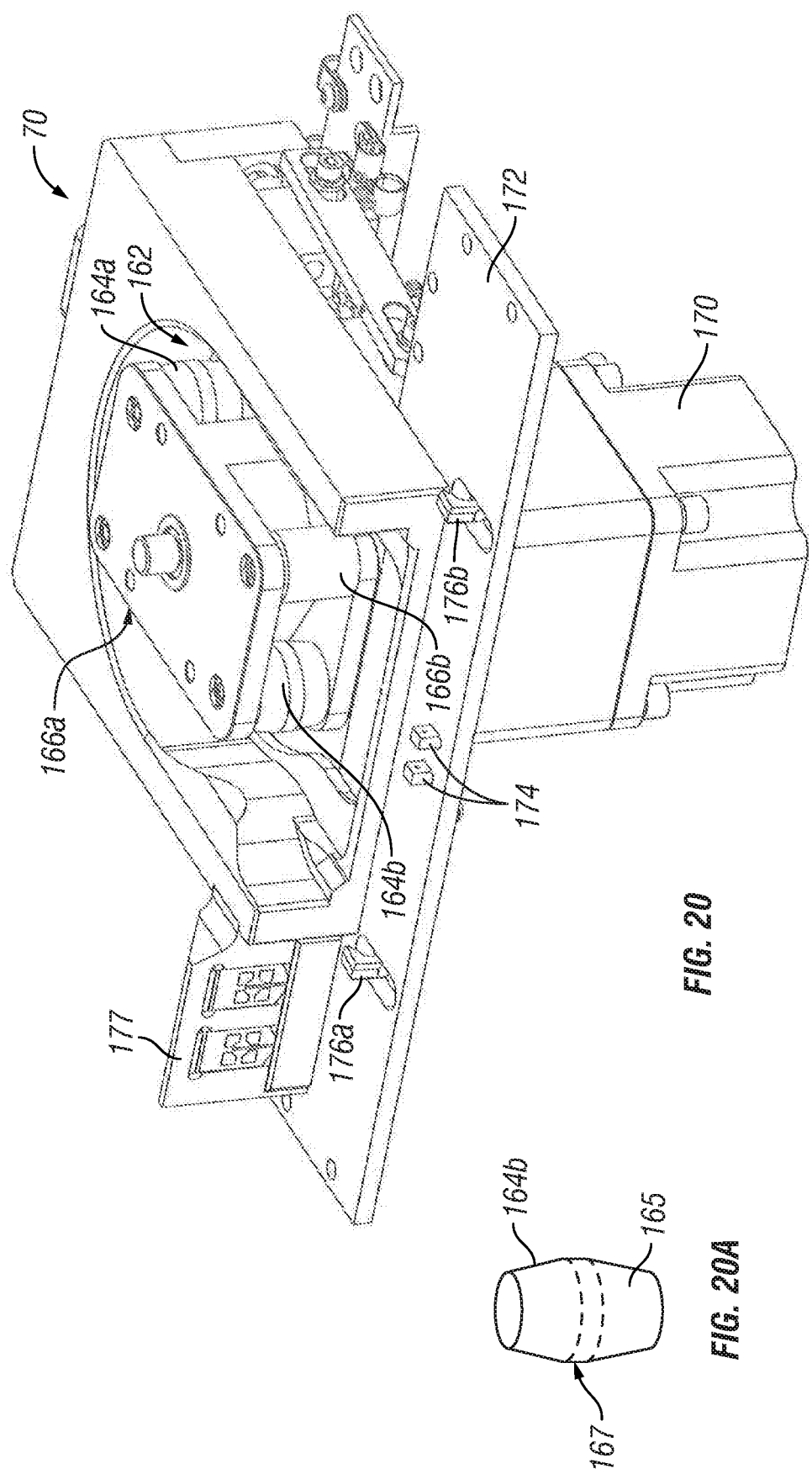
FIG. 20 is a partially disassembled view of the pump assembly wherein the cover has been removed.
FIG. 20A is a separate view of a barrel-shaped guide roller of the pump assembly.
Figure 21:
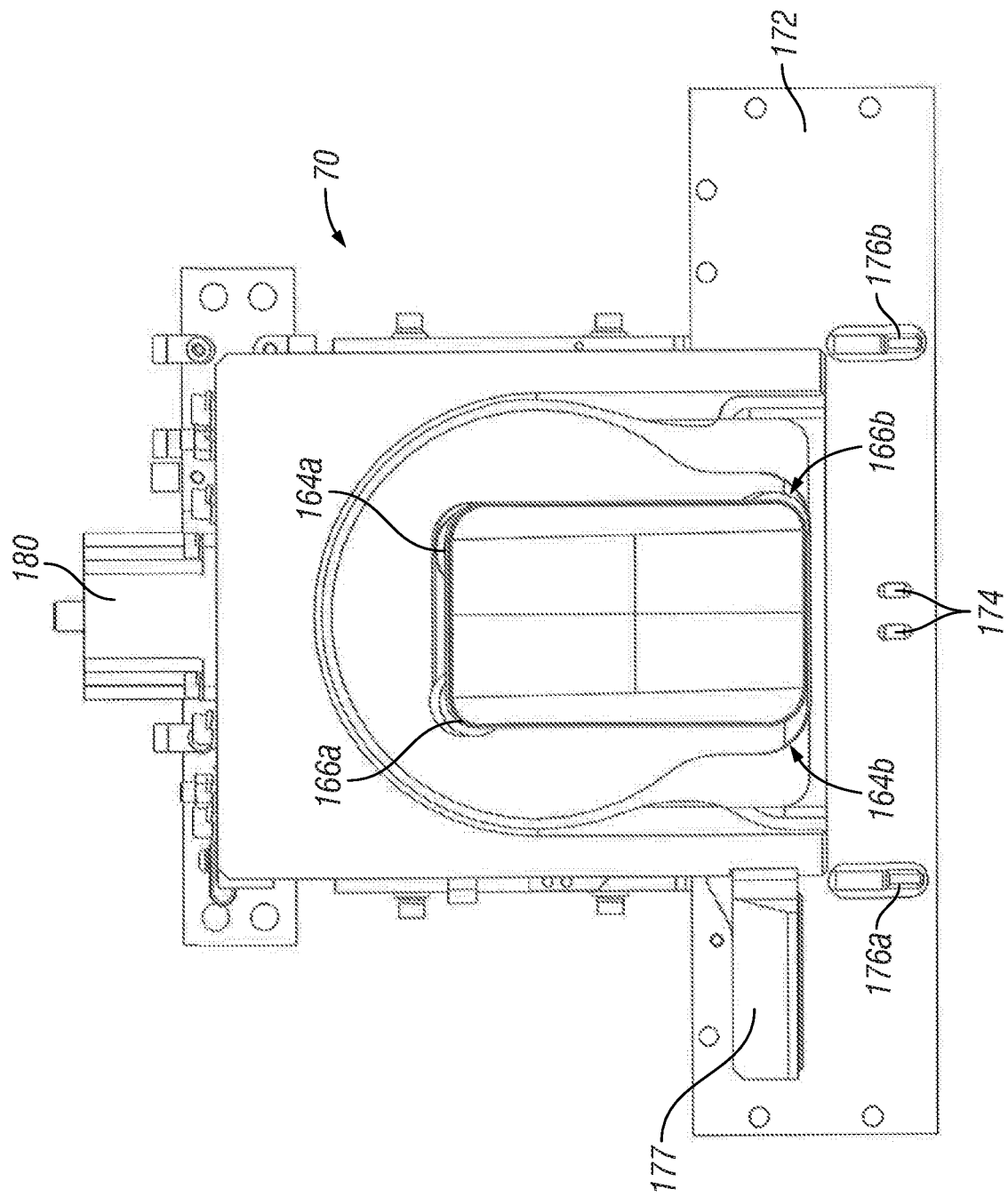
FIG. 21 is a top view of the pump assembly.
Figure 22:
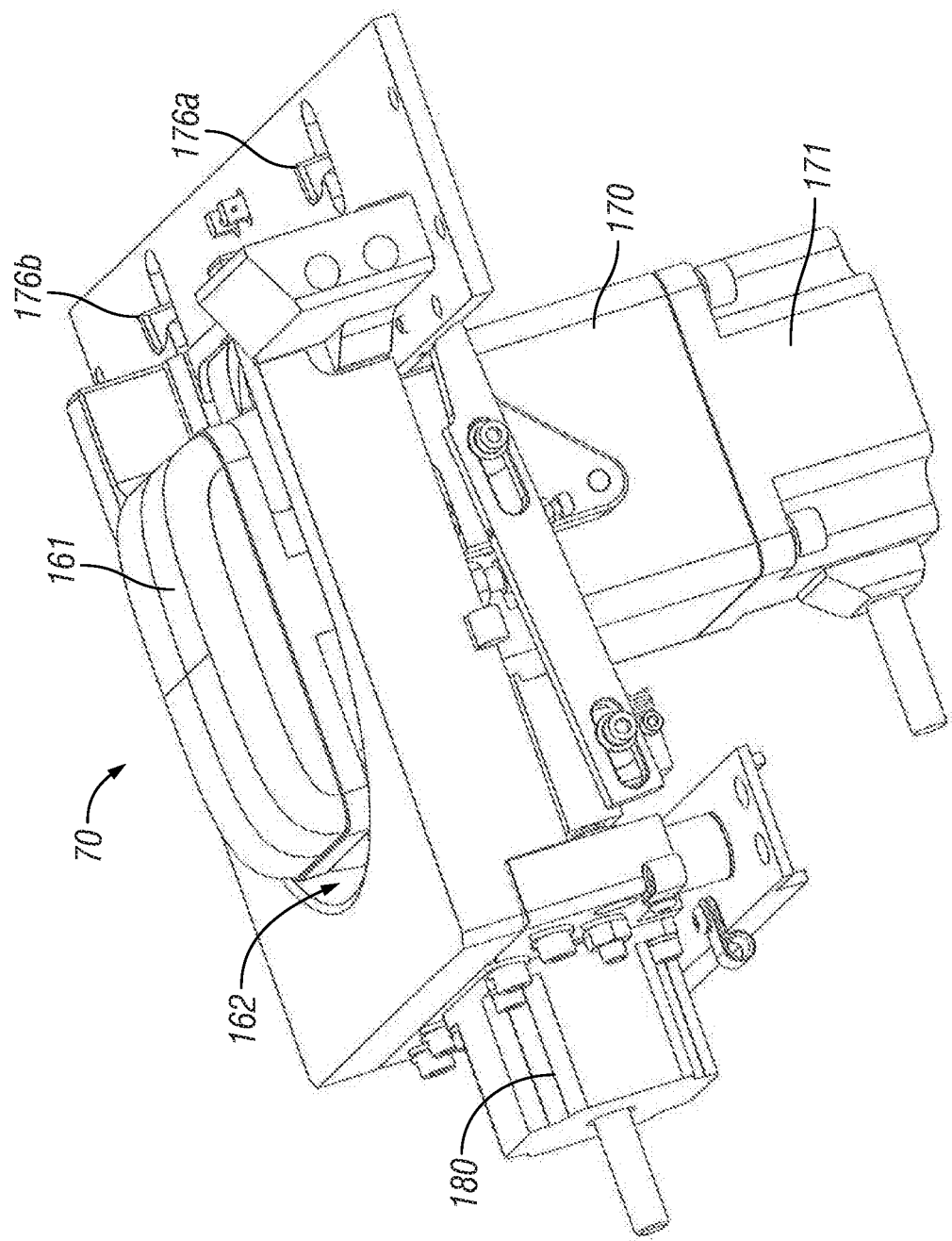
FIG. 22 is a rear perspective view of the pump assembly disposed in an operative configuration.
Figure 23:
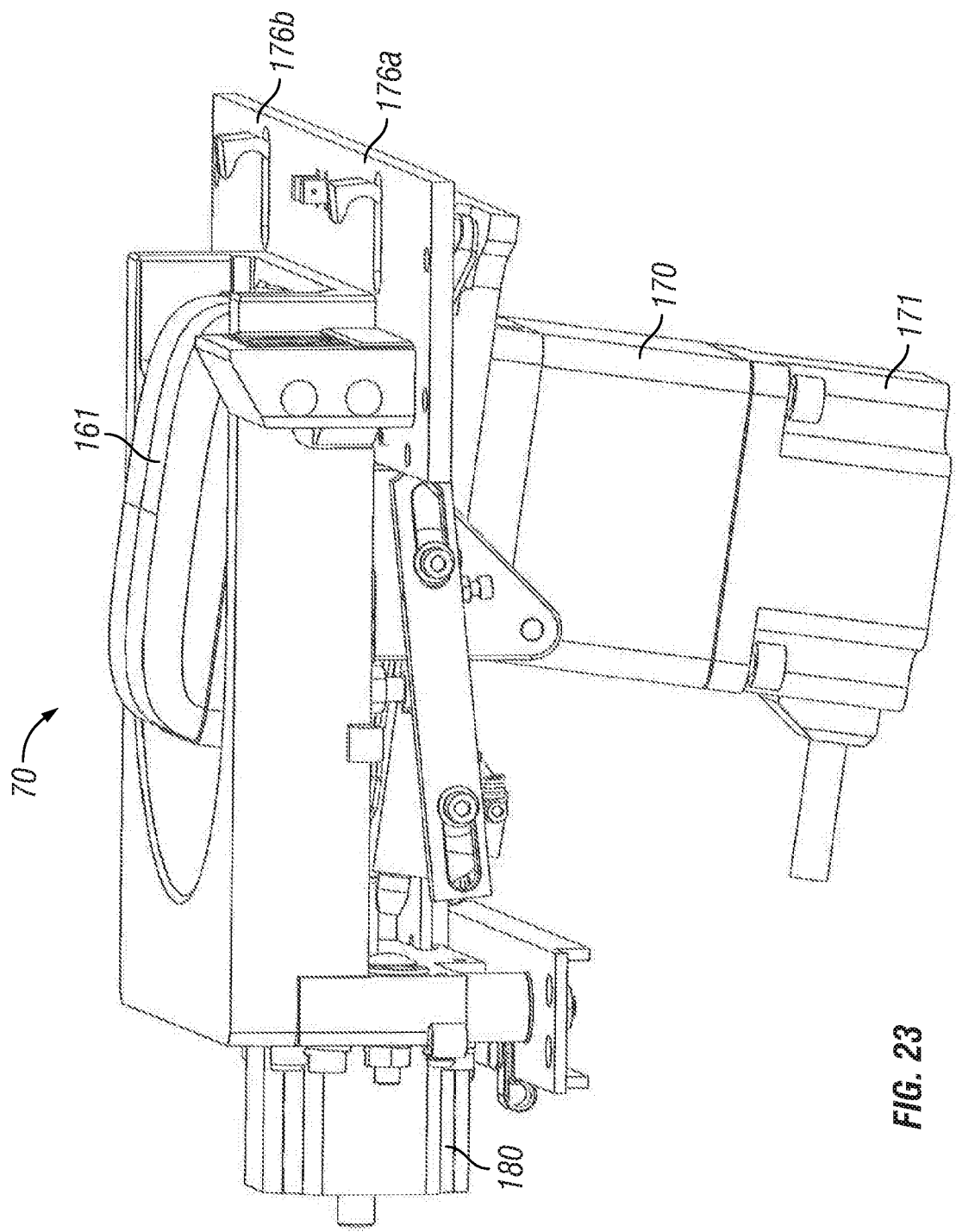
FIG. 23 is a rear perspective view of the pump assembly disposed in a loading configuration.
Figure 24:
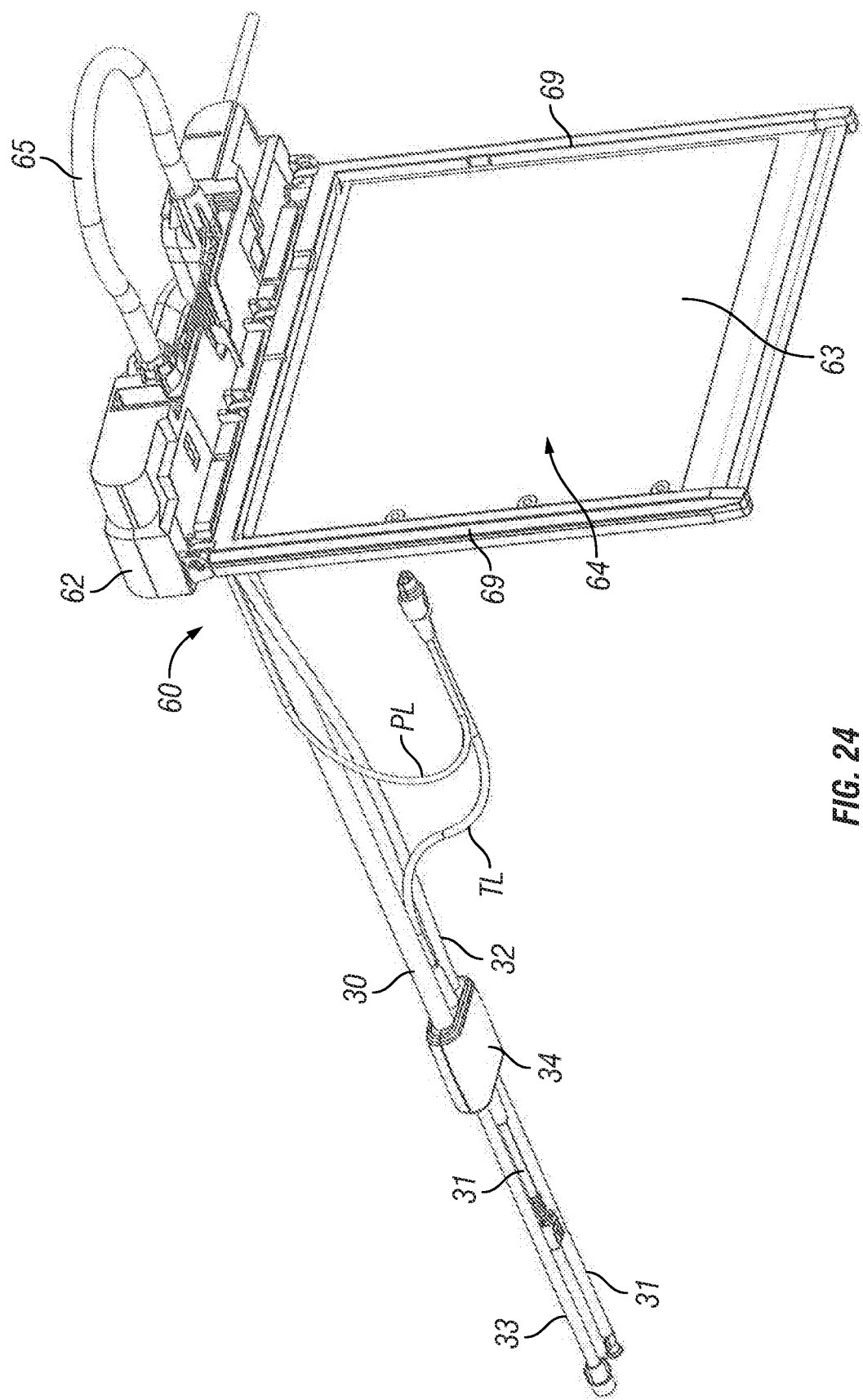
FIG. 24 is a rear perspective view of the tubing/cassette/sensor module assembly of the endovascular heat exchange system.
Figure 25:
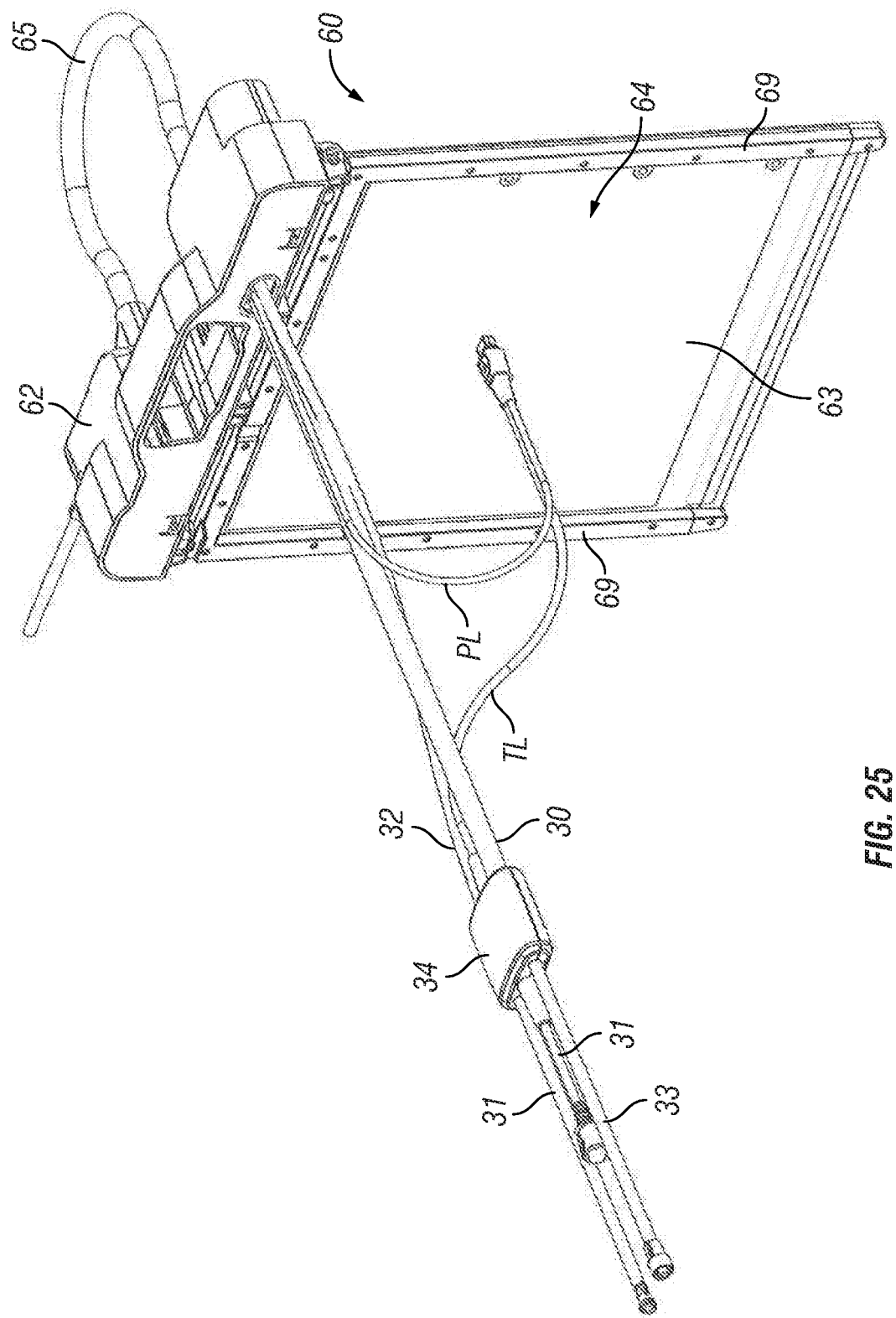
FIG. 25 is a front perspective view of the tubing/cassette/sensor module assembly.

A schematic diagram of an embodiment of a thermal exchange engine or refrigeration loop useable in the systems described herein is shown in FIG. 18. This embodiment has a high side HS and a low side LS. The components shown in this diagram include superheat temperature sensor 130, thermal exchange plate evaporators 132, electric heaters 134, an electronic expansion valve, compressor 140, counterflow heat exchanger 142, filter/drier sight glass 138, and electronic expansion valve 144. In the normal operational state of the cooling engine, the hot gas bypass valve 136 is closed, the compressor 140 is running, and refrigerant flows through the system as follows. First, refrigerant exits the compressor in the gaseous phase at high pressure (typically 8-14 bar) and high temperature (typically 100 to 130 degrees F.) and enters the condenser. In the condenser, heat is transferred from the refrigerant, causing it to condense into it's liquid phase and cool further (typically to 75-95 degrees F.). Liquid refrigerant then passes through the filter dryer 138 which filters the liquid for particulate and absorbs any water contained in the liquid. From there, liquid refrigerant passes the sight glass "S" which allows an observer (e.g. service person) to confirm the refrigerant is in the liquid phase. Liquid refrigerant then passes through the primary channel of the counterflow heat exchanger 142, which causes it to cool further (typically to 40-75 degrees F.) due to heat transfer with the secondary channel of the counterflow heat exchanger. From there, liquid refrigerant passes through the expansion valve 144, which acts as a restriction on the system. After passing through the expansion valve, refrigerant is suddenly at low pressure (typically 2-4 bar) and as a result drops in temperature (to typically 25-35 degrees F.) and partially enters the gaseous phase. Cold, low-pressure, liquid refrigerant then enters the heat exchange plates 132. Heat is added to the refrigerant from the following sources: from the thermal mass of the plates, from saline passing through the cassette heat exchanger, or from water passing through the liquid channels within the cold plates, all of which cause the refrigerant to mostly or entirely enter the gas phase. From the heat exchange plates 132, low-pressure refrigerant flows into the secondary channel of the counterflow heat exchanger where it transfers heat from the refrigerant contained in the primary channel, causing it to warm (to typically 35 to 70 degrees F.). Refrigerant at this point may be mostly or entirely in the gas phase, and then enters the compressor 140, thus completing the circuit. A secondary operational state exists for the cooling engine, where the HGBP valve 136 is open. In this state, hot, gaseous refrigerant exits the compressor and directly enters the heat exchange plates, causing them to warm up rapidly. This secondary state is used when it is desirable to slow down the cooling provided to the patient, or to warm the patient, without turning off the compressor. Alternatively, the compressor can be shut off, however use of the HGBP valve 136 has the advantage of being able to be opened and closed rapidly and repeatedly as necessary to maintain the desired heat exchange plate temperature. One embodiment of a pump 70 (e.g., a peristaltic pump) and associated assembly is shown in FIGS. 19 through 23. The pump 70 comprises a rotor assembly 160 and cover 161 connected to a drive motor 170 which causes the rotor assembly to rotate. The rotor assembly includes guide rollers 164a and 164b, and drive rollers 166a and 166b. As the rotor assembly rotates, during pump operation, the drive rollers apply pressure to the pump tubing (not shown), which is positioned in the pump raceway, thereby causing thermal exchange fluid to move through the pump tubing. The pump raceway is designed with a low height (i.e. as measured along the axes of the rollers) in order to allow the pump to be smaller, lighter weight, and lower cost. However with this low height it is critical to keep the pump tubing aligned with the raceway, in order to avoid jamming of the tubing within the pump assembly (leading to wear of the pump and wear or rupture of the tubing), and to avoid the tubing partially or entirely coming out of contact with the drive rollers and thereby not generating some or all of the pressure needed to pump heat exchange fluid through the catheter. As seen in FIG. 20A, each guide roller 164a, 164b has a tapered (e.g., barrel shaped) side wall 165. The guide roller may include a central section which is not tapered (i.e. parallel to the axis of rotation) 167. The tapered or barrel shape of the guide roller facilitates self-centering of the pump tubing on the guide roller, to ensure that the pump continues to perform as intended. Because the tubing is being stretched over the guide rollers, a normal force is generated, which in turn creates a frictional force. The taper on the rollers is at a shallow angle (e.g., of a range of 5 to 25 degrees) so that the frictional force is sufficient to prevent the tubing from sliding on the roller surface. Given that the tubing does not slide, the taper or barrel shape puts a higher tensile load on the pump tubing at the center of the roller (i.e. at the widest part of the barrel or roller), and a lower tensile load on the pump tubing at either the top or bottom edges of the roller (i.e. the narrowest part of the barrel or roller). This difference in tensile forces leads to the self-centering effect by developing a net force acting on the tubing along the axis of the roller, in the direction of the center of the roller. A front portion of the pump 70 is mounted on a front plate 172. Optical sensors 174, for detecting when a cassette 64 and its cassette housing 62 are in place and properly positioned for operation, may also be located on the front plate 172. Hooks 176a, 176b extend through slots in the front plate 172. These hooks 176a, 176b are positionable in retracted positions which allow installation of the cassette 64 and insertion of the pump tubing 65 in the pump raceway 162. Thereafter, these hooks 176a and 176b are movable to advanced positions wherein they exert a force on the cassette housing 62 at two separate points of contact thereby deterring unwanted movement of the cassette 64, cassette housing 62 or attached pump tubing 65, and securing the cassette in position for system operation. Also mounted on the front plate 172 are level sensors for sensing fluid levels within a reservoir formed within the cassette housing 62. The pump 70 is alternately disposable in an operative configuration (FIG. 22) and a loading configuration (FIG. 23). Translational motor 180 causes the hooks to move between a retracted and advanced position, and causes the pump to move between an operative and loading configuration or position.

Priming of the system, when the cassette 64 is positioned in the cassette receiving space 66 between thermal exchange plates 80, may be performed quickly by using one or more pump direction changes. The pump 70 may be switched back and forth between running in reverse and running in a forward direction for various durations of time, at various speeds. The first pump reversal creates a vacuum and the subsequent reversals help remove bubbles from the system/line.

To purge the thermal exchange fluid from the system the pump 70 may be run in reverse. In one example, the pump 70 may be run in reverse at 60% of max pump speed for about 20 seconds, during which the return line or vessel outlet line is closed to prevent the cassette vessel/bag from refilling with thermal exchange fluid or saline when the pump is reversed or opened. A check valve may be utilized, which may be positioned in the cassette housing, e.g., in the vessel outlet tubing, between the tubing and the reservoir, to prevent the vessel/bag from refilling with thermal exchange fluid or saline when the pump is reversed or open. For example, in some embodiments, the check valve may be integrated into the inflow connector 206 seen in FIG. 28 to prevent fluid from back-flowing into the vessel/bag 63 when the pump is reversed or open . . . .

Figure 26:
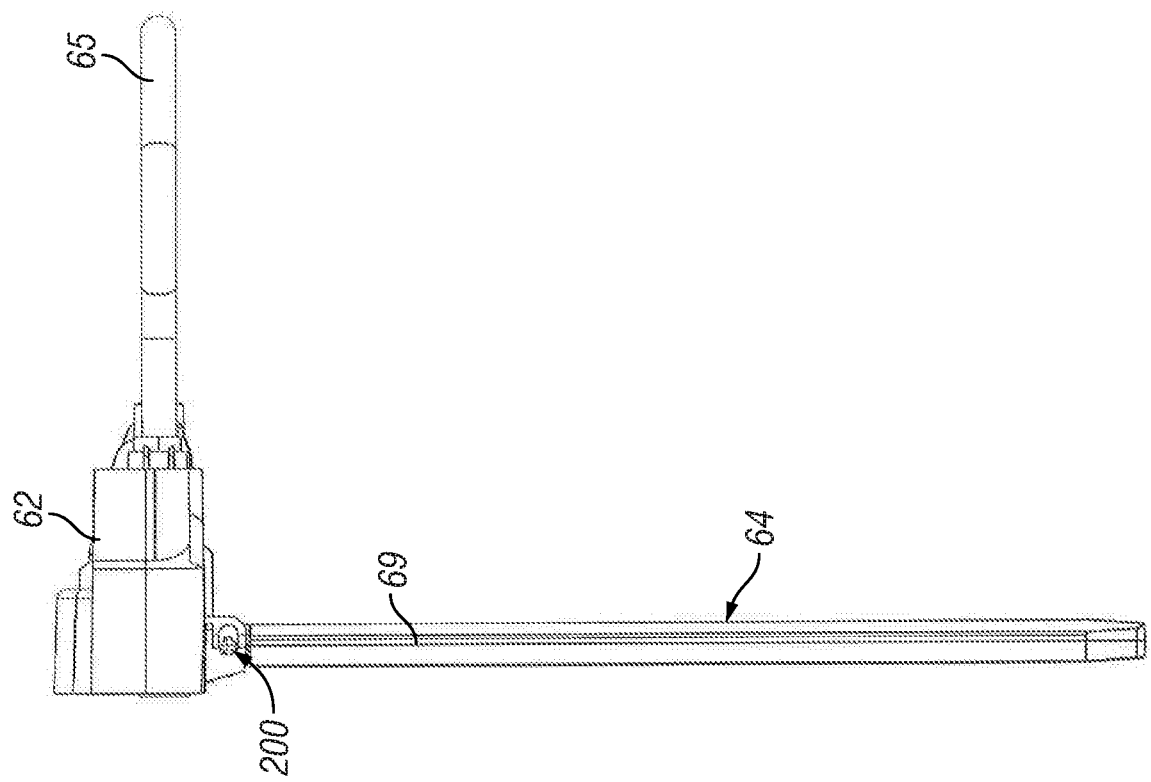
FIG. 26 is a side view of the cassette and pump tubing portions of the tubing/cassette/sensor module assembly disposed in an open/locked configuration useable for insertion and operation.
Figure 27:
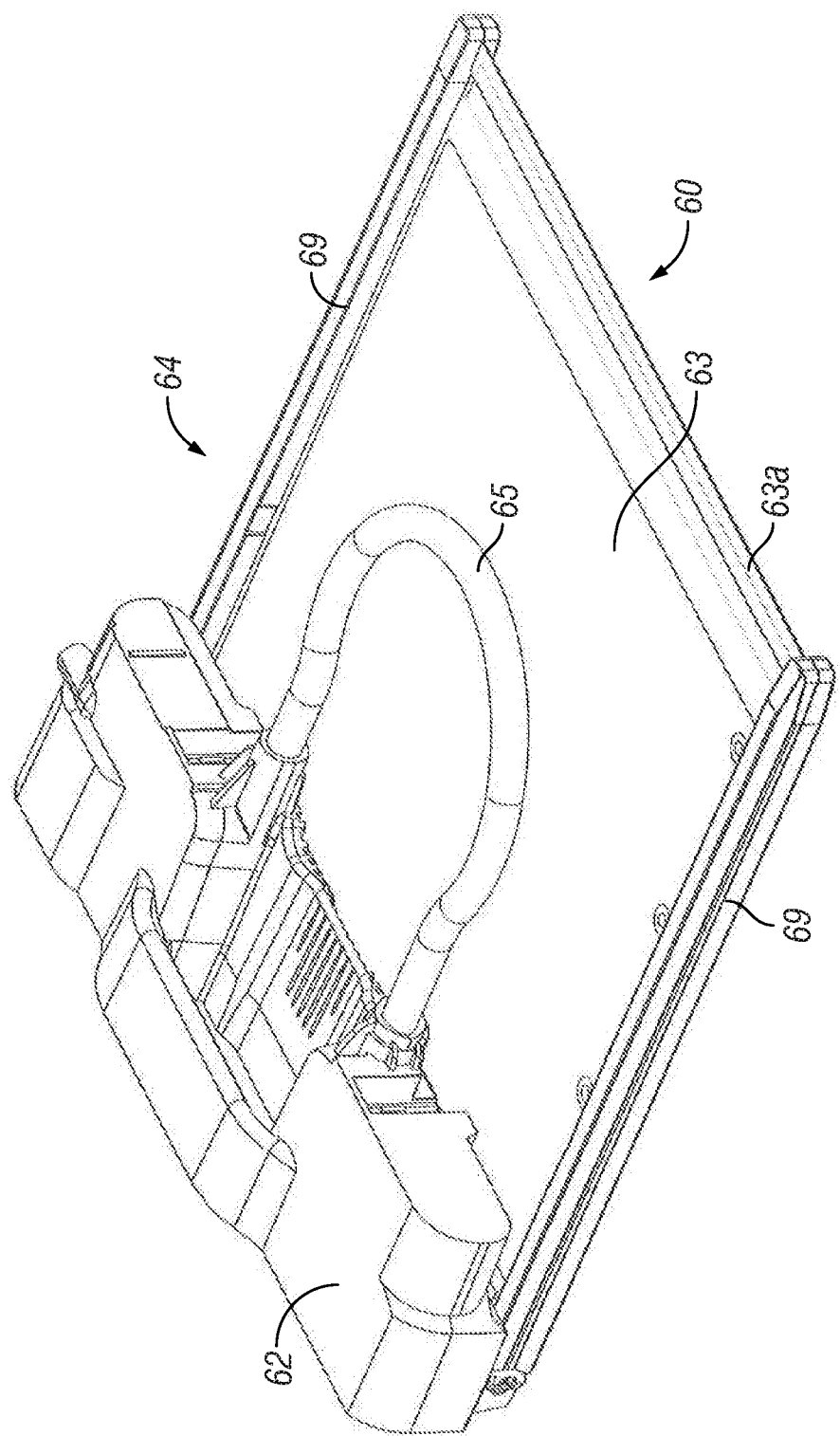
FIG. 27 is a rear perspective view of the cassette and pump tubing portions of the tubing/cassette/sensor module assembly disposed in a closed configuration prior to insertion and operation.
Figure 28:
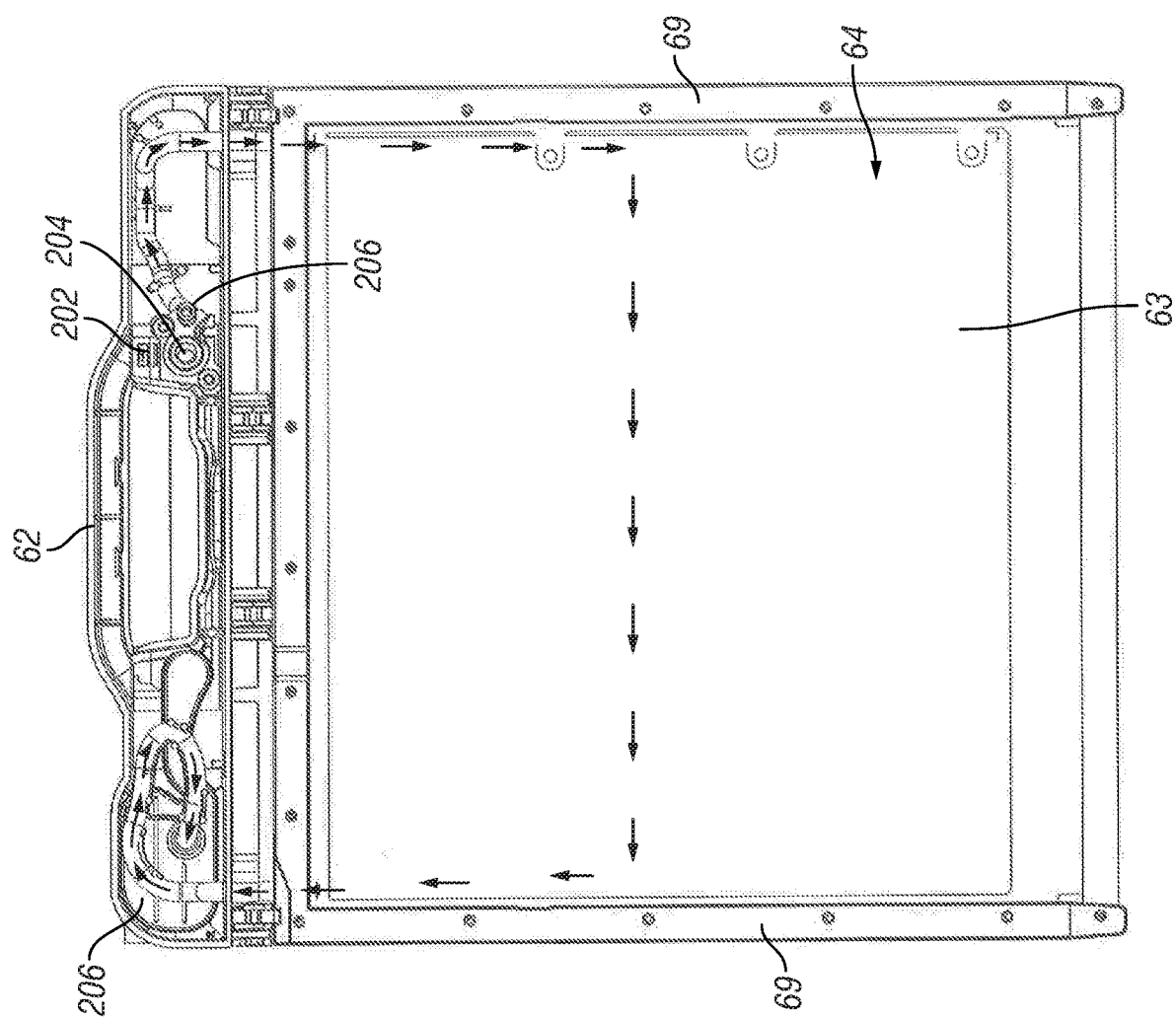
FIG. 28 is a cross sectional view of the cassette portion of the tubing/cassette/sensor module assembly.

FIGS. 24 through 28 show further details of the tubing/cassette/sensor module assembly 60 or cassette assembly. The cassette housing 62 is attached to a frame 69 which supports the side edges of the expandable vessel or bag 63. A lower edge 63a of the expandable vessel or bag is sealed and may include a support. As seen in FIG. 28, the cassette housing (bottom cover removed) 62 encloses a reservoir 206, pressure sensor 202, outflow connector 204 which is connected to the pulse-damping outflow conduit 30, inflow connector 206 which is connected to return or inflow conduit 32. During system operation, thermal exchange fluid returns from the catheter, flowing through inflow conduit 32, through inflow connector 206, through vessel inlet tubing, into the expandable vessel or bag 63, through the expandable vessel or bag 63 from one side to the other as indicated by arrows on FIG. 28, exchanging heat with refrigerant flowing through the thermal exchange plates, then out of the vessel through vessel outlet tubing, into reservoir 206, through pump tubing 65, through outflow connector 204, through pulse-damping outflow conduit 30 and back to the catheter. Refrigerant flows through the refrigerant flow channels in the thermal exchange plates in a first direction, while thermal exchange fluid flows though the expandable vessel in a second direction that is substantially opposite the first direction. This counter flow of refrigerant and thermal exchange fluid helps maximize heat exchange between the two fluids.

To minimize the force required to insert or remove the Heat Exchange (Hx) Bag or vessel from the Cold Plates, several methods are described below.

The frictional force between the Cold Plates and the Hx Bag may be reduced by adding coating to the surface of the Cold Plates that lowers its coefficient of friction. Possible coatings include Teflon or similar. The surface of the Cold Plates may be polished. A coating may be added to the surface of the Hx Bag that lowers its coefficient of friction, e.g., materials that may be used include silicone, or similar (these can be brushed, sprayed, dipped, etc.)

In some embodiments, a layer (release layer or antifriction layer) of material may be placed over the outside surface of the Hx Bag which lowers its coefficient of friction. Possible materials include paralyene, HDPE (Triton), ePTFE, PTFE, FEP or similar. A low friction sheet made of these materials may be used. In certain embodiments, a fluoropolymer may be placed on the cold plates and use a urethane HX bag with HDPE release layer on the bag. The HX bag may include an HDPE release layer on each side of the bag with each layer and the urethane bag affixed to the cassette frame with pegs or clamps. Alternatively, a single longer piece of HDPE release layer may be folded around the HX bag and then the bag and release layers are affixed to the cassette frame with pegs or clamps The pulse-damping outflow conduit 30 functions not only as a conduit through which the thermal exchange fluid flows but also a pulse damper for damping pulses in the thermal exchange fluid as it flows through the outflow conduit, to a catheter. Pulses may arise due to the nature of the pump used for the thermal exchange fluid. For example, in the case of a peristaltic pump with two drive rollers, at certain times both drive rollers are in contact with the pump tubing, and at other times only one drive rollers is in contact with the pump tubing, depending on the angular position of the pump rotor within the raceway. The thermal exchange fluid system volume suddenly increases when a roller from the peristaltic pump loses contact with the pump tubing as a normal part of the pump's rotation. This happens because a section of the pump tubing that had been flattened, and had zero cross-sectional area, suddenly becomes round and contains a non-zero cross-sectional area. The increase in system volume is approximately the cross-sectional area of the tubing in its round state multiplied by the length of tubing flattened by the roller. The pulse dampener should have enough flexibility to contract suddenly and decrease its volume by approximately this amount in order to dampen the pulse. For example, the volume gained by the pump tubing when a roller leaves contact with it may be 2 to 3 mL. Therefore it is desirable for a pulse dampener to be able to decrease its volume by this amount with a minimal change in system pressure. The pulse damping conduit may comprise, for example, tubing that has sufficient elastic or flexural properties to dampen, attenuate or reduce the amplitude of pulses in the thermal exchange fluid as it flows therethrough. For example, if the conduit is able to expand by a volume of 20 to 30 mL under 60 psi of pressure, then it will be able to contract by 2 to 3 mL when the pressure drops by approximately 6 psi. The more compliant the conduit is, the smaller the pressure drop that occurs when the tubing contracts, and therefore the better the conduit performs its damping function. While a highly compliant tubing is desirable, at the same time, the conduit should have sufficient mechanical strength to expand and contract by this amount repeatedly without rupture. For example if a peristaltic pump has two driving rollers, turns at 40 RPM, and a procedure lasts for 12 hours, the conduit must withstand 57,600 pulsation cycles.

To balance these conflicting requirements, for example, in certain embodiments, the length of the pulse damping conduit may be about 90" and could range between 20" and 100". The conduit may be made of a low durometer polyurethane (Prothane II 65-70A) and have a large ID at 0.25" and could range between 0.15" and 0.40". The wall thickness of the conduit is about 0.094" and could range between 0.06" and 0.25".

As seen in FIGS. 26 and 27 the cassette housing 62 is connected to the frame 69 by a hinged connection 200. As packaged prior to use, the hinged connection 200 is in a closed configuration so that the housing 62 and accompanying pump tubing 65 are folded over the cassette's flexible vessel or bag 63 in the manner seen in FIG. 27. At the time of use, the hinged connection is moved to an open configuration causing the housing 62 and accompanying pump tubing 65 to extend at a substantially right angle relative to the expandable vessel or bag 63, as seen in FIG. 26. The hinged connection 200 locks in such open position so that the cassette 64 cannot be returned to the folded configuration seen in FIG. 27 without removing, disrupting or altering the hinged connection 200. For example, the hinged connection may be unlocked or disengaged by sliding a hinge protrusion forward or backward within a hinge slot, thereby disengaging the lock.

Figure 29:
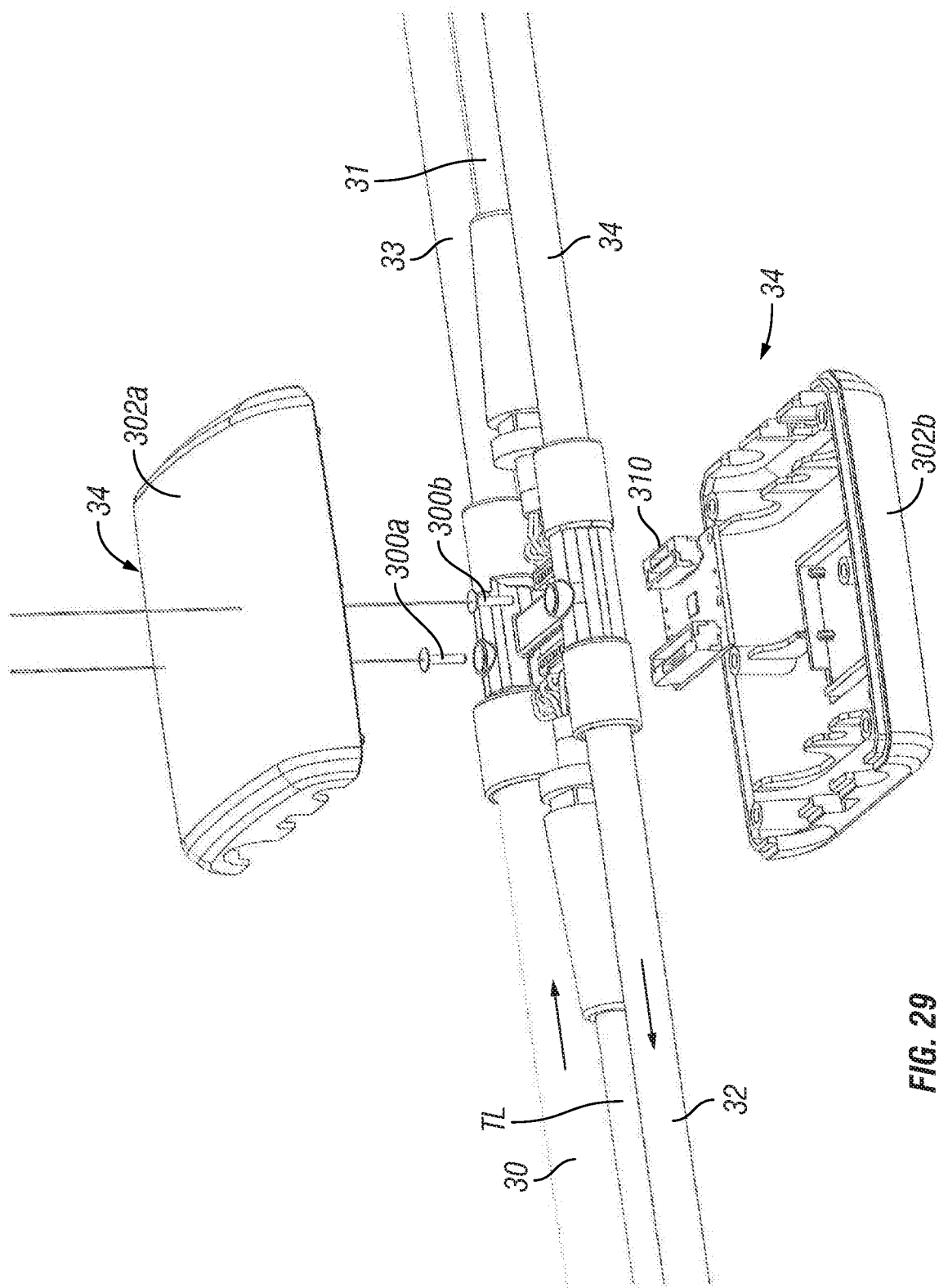
FIG. 29 is an exploded view of the sensor module portion of the tubing/cassette/sensor module assembly.

Details of the sensor module 34 are shown in FIG. 29. The sensor module comprises upper and lower housing portions 302*a*, 302*b* which, in combination, form an enclosed housing. Within the housing there is positioned an electronic storage medium 310 which holds encoded information. Examples of the types of encoded information that may be stored include but are not limited to; unique identifier(s) for the changeable components (e.g., manufacturer identification, part number, lot number, etc.), indications of whether the changeable component(s) have previously been used (e.g., an encoded indication of first use), indications of whether the changeable component(s) is/are expired (e.g., encoded expiration date), operational characteristic(s) of the changeable component(s) (e.g., encoded indications of the size, type, volume, etc. of the changeable component(s). In this non-limiting example, the electronic storage medium comprises electrically erasable programmable read-only memory (EEPROM). One example of how the controller may check to determine whether the components had previously been used is by checking the EEPROM or other data storage medium 310 for a First-Use date. The First-Use date would be "EMPTY" if this is the first time the changeable component (e.g., the cassette assembly) has been connected to a console 14. If the First-Use date is "EMPTY", the controller will write the current date to the EEPROM's memory location where the First-Use date will then be stored.

Also, within the housing of the sensor module 34, there are provided a first temperature sensor (e.g., a thermistor) for sensing the temperature of thermal exchange fluid flowing to the catheter 12 and a second temperature sensor 300*b* (e.g., a second thermistor) for sensing the temperature of thermal exchange fluid returning from the catheter 12. Signals from these first and second temperature sensors 300*a*, 300*b*, as well as body temperature signals from the connected body temperature sensor TS and encoded data from the electronic storage medium 310, are transmitted through temperature lead TL. A pressure lead PL, which carries signals from a pressure sensor that senses the pressure of thermal exchange fluid within the cassette tubing or console 14, combines with the temperature lead TL, as shown, and the combined leads are connected to the control console 14. In this manner, the controller in the console main housing receives signals indicating a) the encoded data from the electronic storage medium 310, b) subject body temperature, c) thermal exchange fluid temperature flowing to catheter, d) thermal exchange fluid temperature flowing from catheter and e) thermal exchange fluid pressure. The controller may be programmed to use the encoded information and/or sensed temperatures and/or sensed pressure for control of the system 10 and/or for computation/display of data. For example, the controller may be programmed to use the difference between the sensed temperature of thermal exchange fluid flowing to the catheter and the sensed temperature of thermal exchange fluid flowing from the catheter, along with the fluid flow rate or pump speed, to calculate the Power at which the body heat exchanger is operating. Power may be calculated by the following equation:

Power (Watts)=($HE$ Fluid Temp OUT–$HE$ Fluid Temp IN)·Flow Rate·$CP$ wherein:

HE Fluid Temp IN is the current measured temperature of heat exchange fluid flowing into the heat exchanger 18;

HE Fluid Temp OUT is the current measured temperature of heat exchange fluid flowing out of the heat exchanger;

Flow Rate is the measured or calculated flow rate of heat exchange fluid through the heat exchanger; and CP is the specific heat capacity of the heat exchange fluid.

Such Power may be displayed on the display or user interface 24. Also, the controller may be programmed to check and accept the encoded information from the electronic storage medium 310 before allowing the system 10 to be used for warming or cooling the body of the subject and/or to adjust operating variable or parameters to suit operative characteristics (e.g., size, operating volume, type) of the catheter 14, cassette 64, temperature probe, tubing or other components. This pre-check of the encoded information may occur in various sequences or processes. One example of a process by which this pre-check may occur is by the following steps:

1. User connects tubing/cassette/sensor module assembly 60 to control console 14.
2. Console controller detects this connection. Such detection of the connection may occur by the controller scanning the temperature sensor channels, which will open channels when no tubing/cassette/sensor module assembly 60 is connected but will become non-open when a tubing/cassette/sensor module assembly 60 is connected. Alternatively, this could be done by the controller polling the polling the pressure sensor in the cassette 64 or the EEPROM in the sensing module 34 for a response.
3. Controller establishes a secure communication session with the EEPROM and reads its content. The EEPROM's content may be encrypted such that it is readable only by a processor having a secret key. In some embodiments, the EEPROM itself may be encoded with a secret key such that the controller may establish a secure session in connection with the sensing module 34.
4. In some embodiments, the EEPROM content may comprise the following information, some or all of which must be checked and verified/accepted by the controller before priming and operation of the system 10 may occur:
   a. Manufacturer ID (factory written)
   b. Cassette part # (factory written)
   c. Shelf-life Expiration date (factory written)
   d. Lot # (factory written)
   e. Expiration duration since first use (factory written)
   f. First-Use date (written when the cassette is first plugged into the console)

Figure 30:
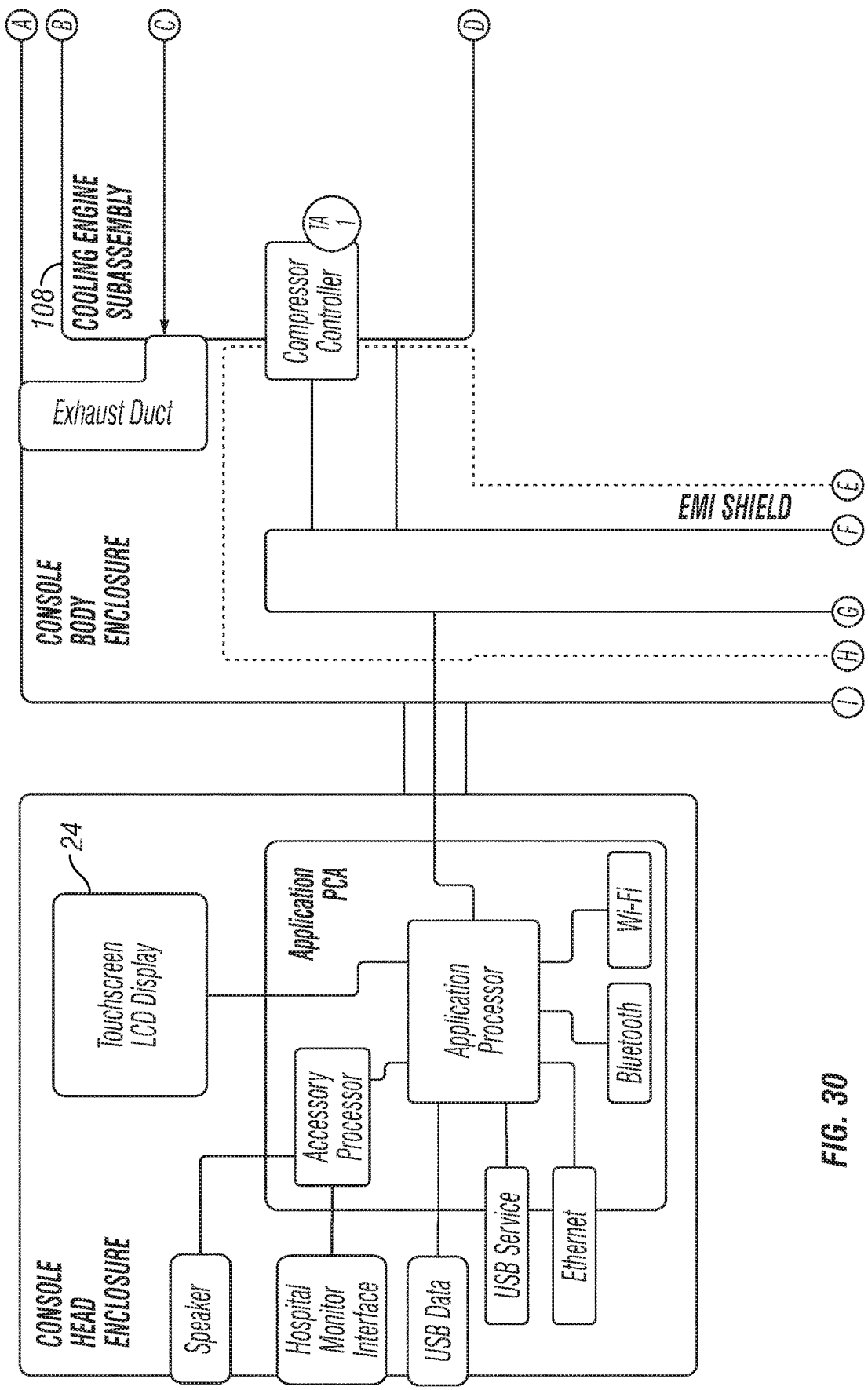
FIG. 30 is a schematic diagram of an endovascular heat exchange system. (convert to black/white formalize)
Figure 30:
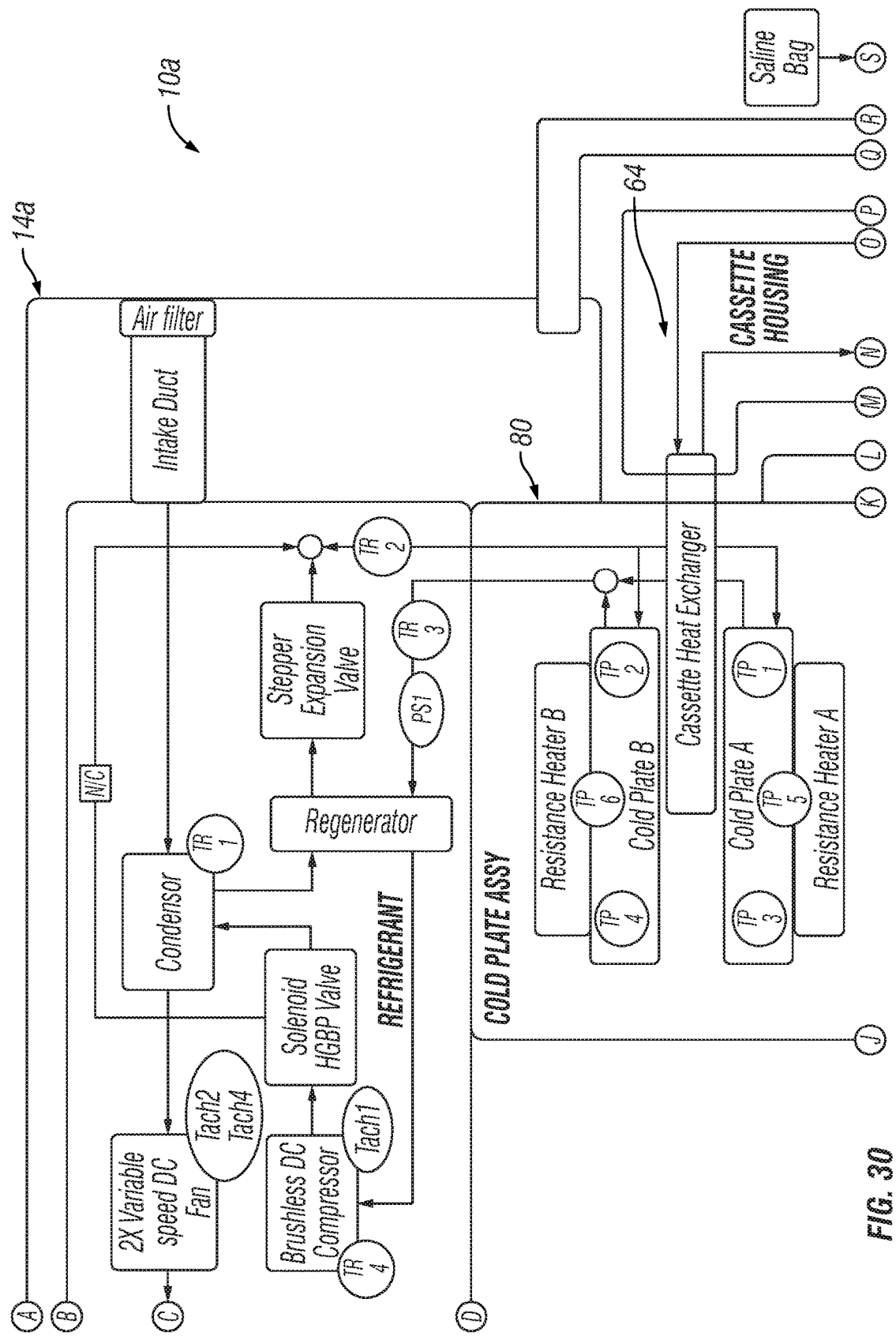
Figure 30:
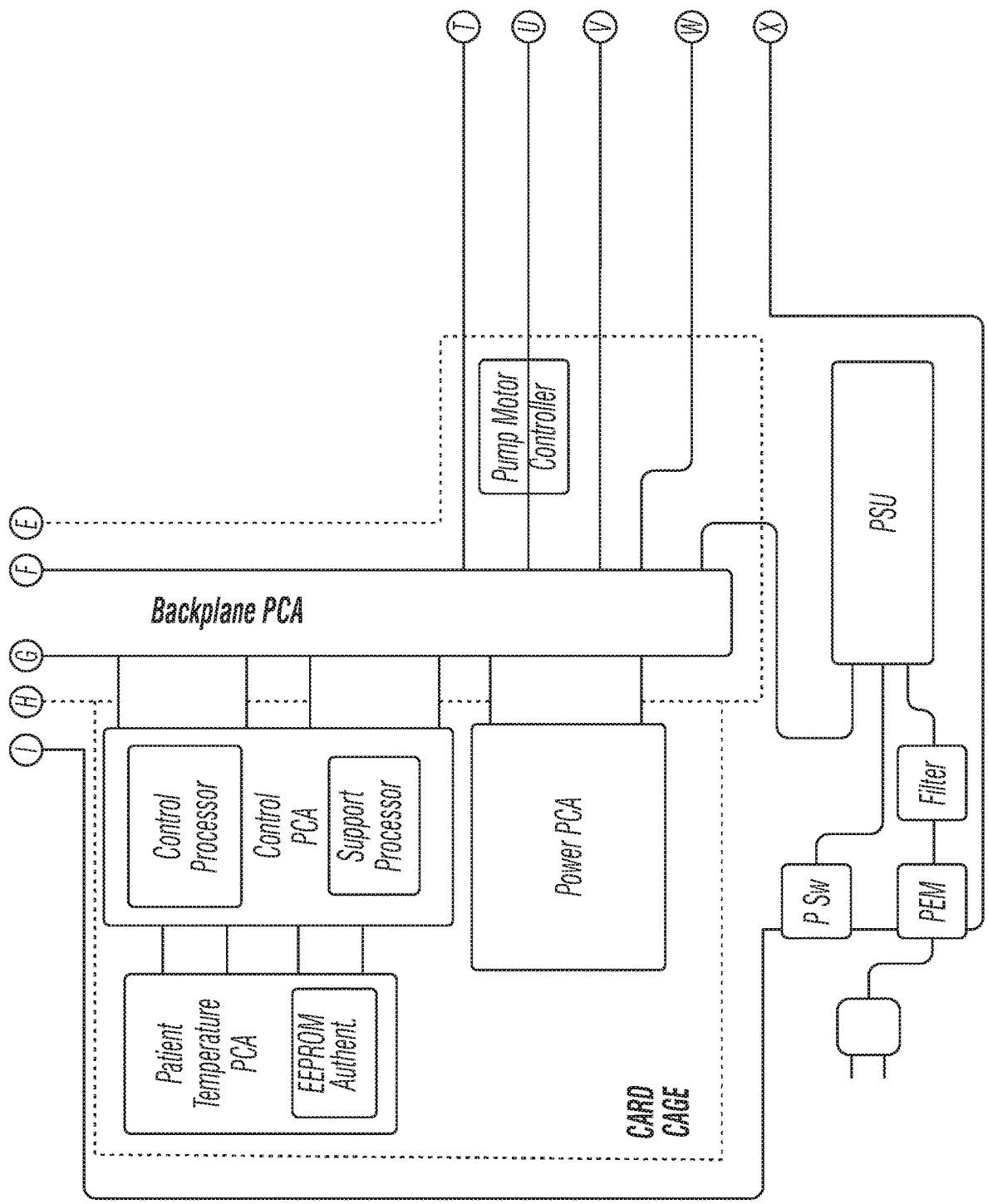
Figure 30:
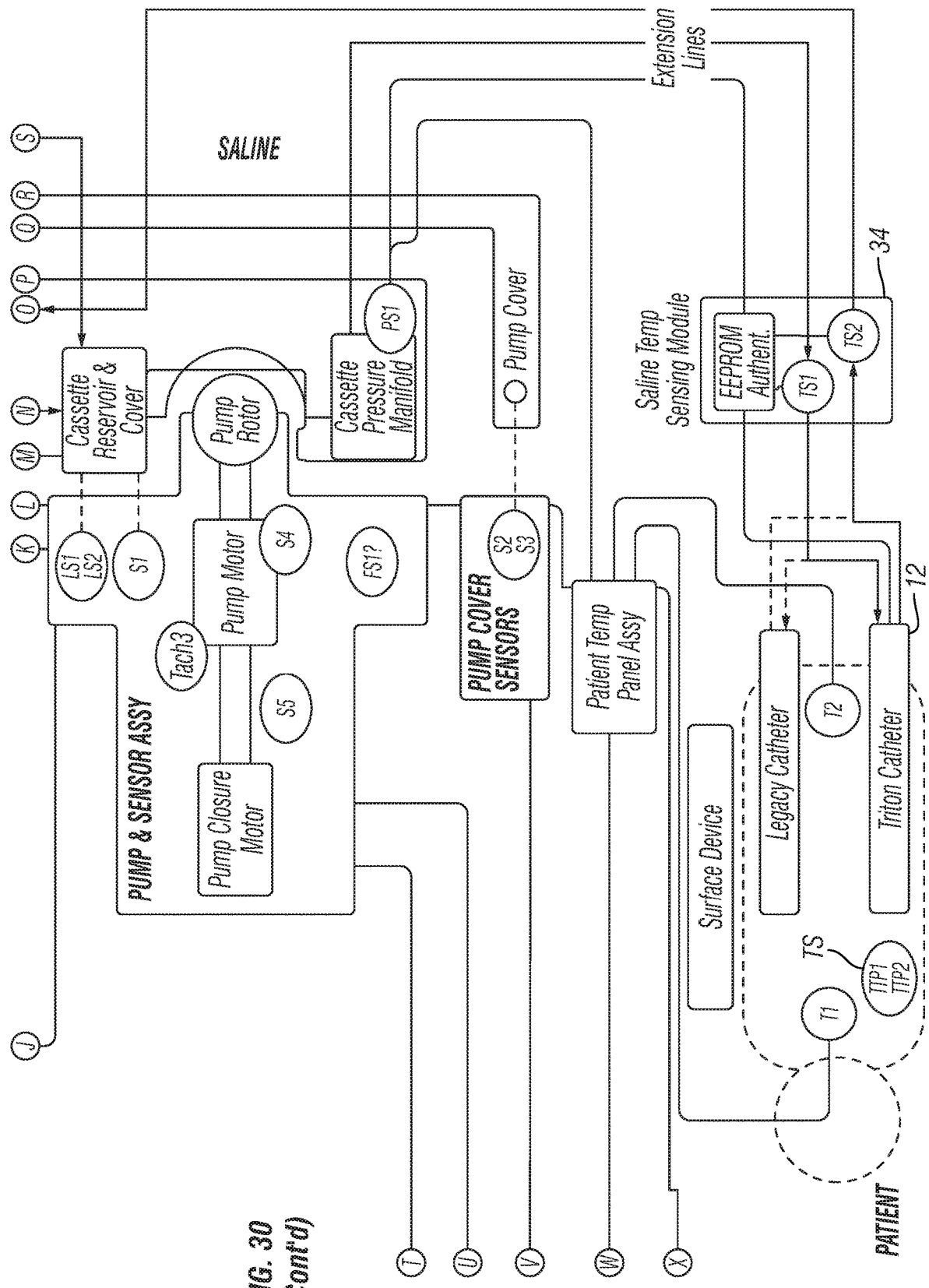

FIG. 30 is a schematic diagram of the endovascular heat exchange system 10. This schematic diagram shows major components of the system 10, including the console 14, heat exchange catheter 12, thermal exchange engine 108, console head/user interface 24, thermal exchange plates 80 and cassette 64. Additionally, this schematic diagram includes other components and functional indicators labeled according to the following legend:

| | |
|---|---|
| FS | FLOW, SALINE |
| FW | FLOW, WATER |
| LS | LEVEL, SALINE |
| LW | LEVEL, WATER |
| PSR | PRESSURE SWITCH, REFRIGERANT |
| PS | PRESSURE, SALINE |
| S | SWITCH |
| TACH | TECHOMETER |
| TA | TEMPERATURE, AIR |
| TR | TEMPERATURE, REFRIGERANT |
| TP | TEMPERATURE, PLATE |
| TS | TEMPERATURE, SALINE |
| TW | TEMPERATURE, WATER |

To set up the system 10 a new tubing/cassette/sensor module assembly 60 or cassette assembly is obtained and removed from its packaging and the cassette 64 is unfolded to the opened and locked configuration seen in FIG. 26. The access cover 42 of the control console 14 is opened. An "open" button is pressed on the touch screen user interface 24 causing the pump 70 to shift to its loading configuration as seen in FIG. 23. The cassette frame 69 and expandable vessel or bag 63 are inserted downwardly into the cassette receiving space 66 until the housing 62 abuts front plate 172. The pump tubing 165 is inserted within the pump raceway 162. The access cover 42 is then closed and a "close" button is depressed on user interface 24 causing the pump 70 to shift to the operative configuration (FIG. 22). The user then presses a "prime" button on user interface 24 to prime the system with thermal exchange fluid from a bag or other container that has been hung on bracket 48 and connected to the system 10.

After the system has been primed, the catheter 12 is connected and inserted into the subject's body and the system 10 is operated to warm or cool the subject's body as desired.

Figure 31:
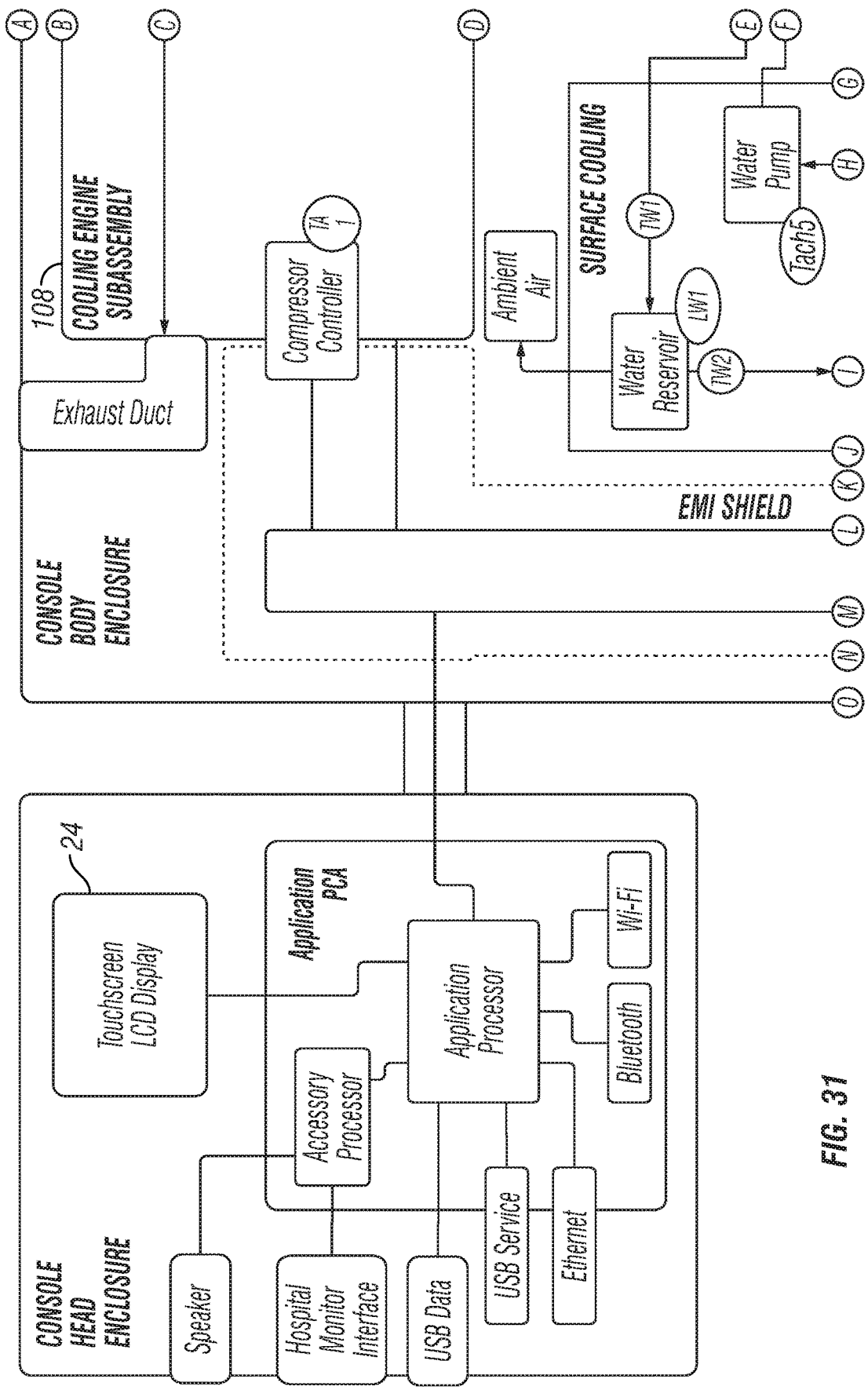
FIG. 31 is a schematic diagram of a heat exchange system capable of providing endovascular and/or body surface heat exchange. (convert to black/white and formalize)
Figure 31:
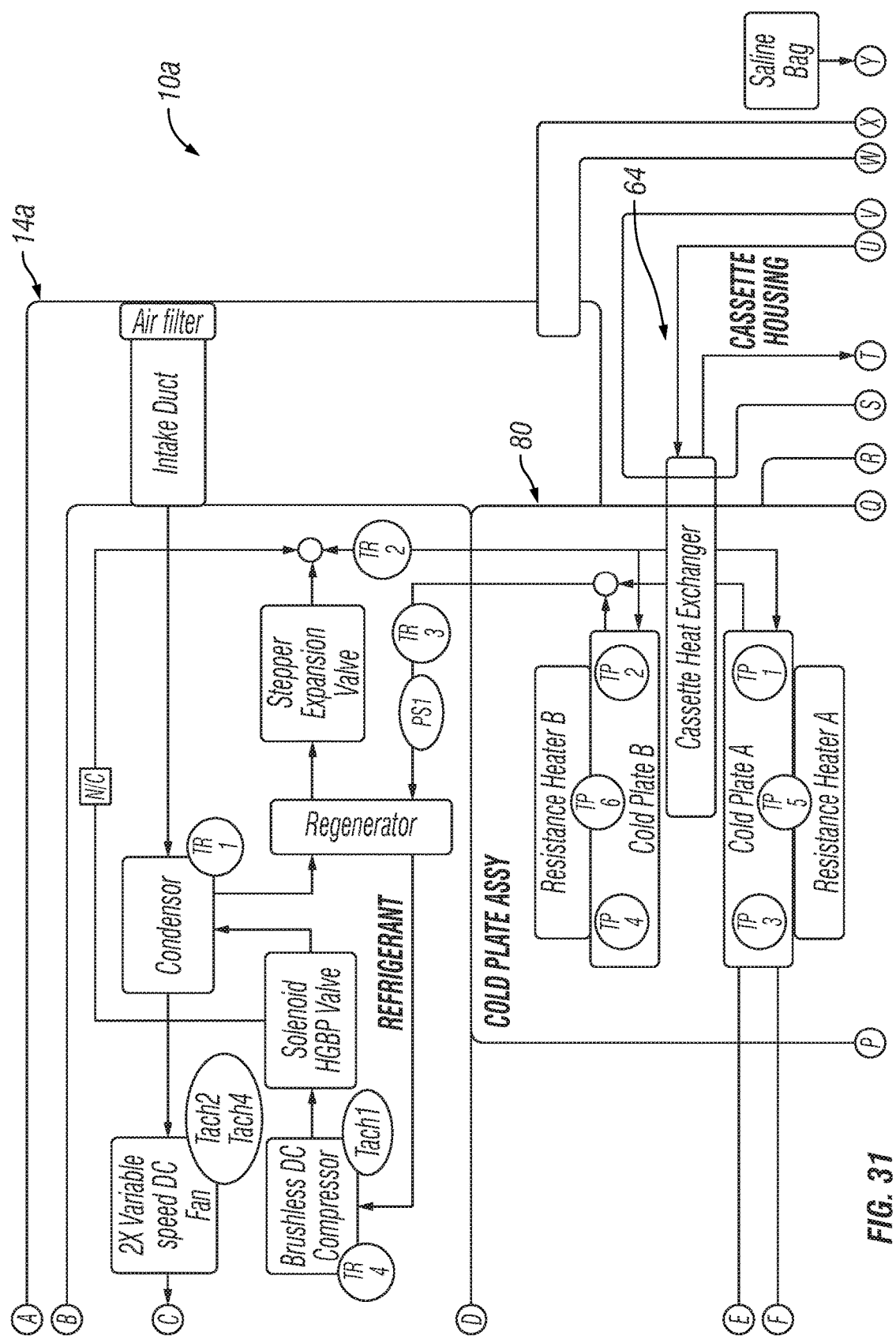
Figure 31:
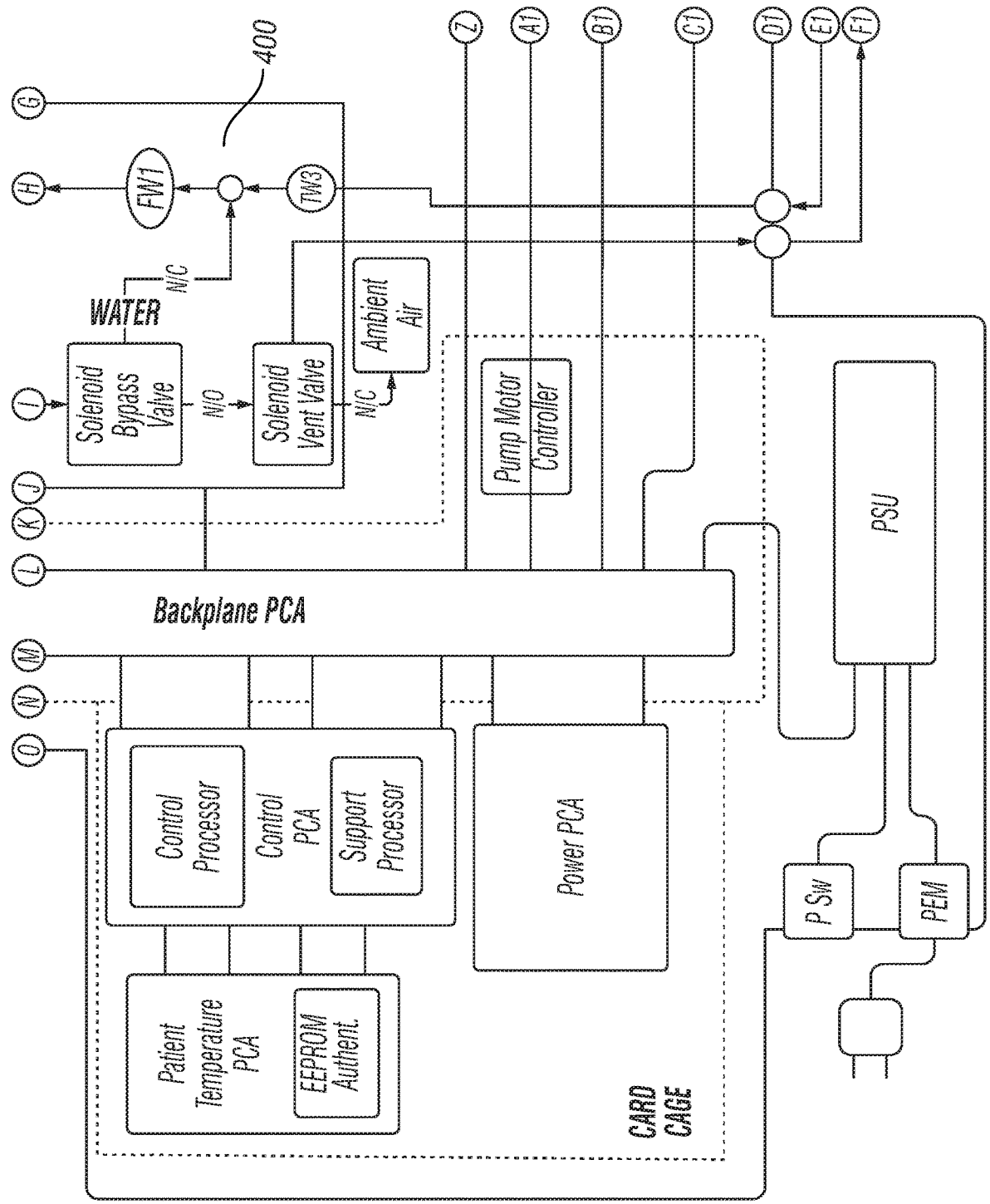
Figure 31:
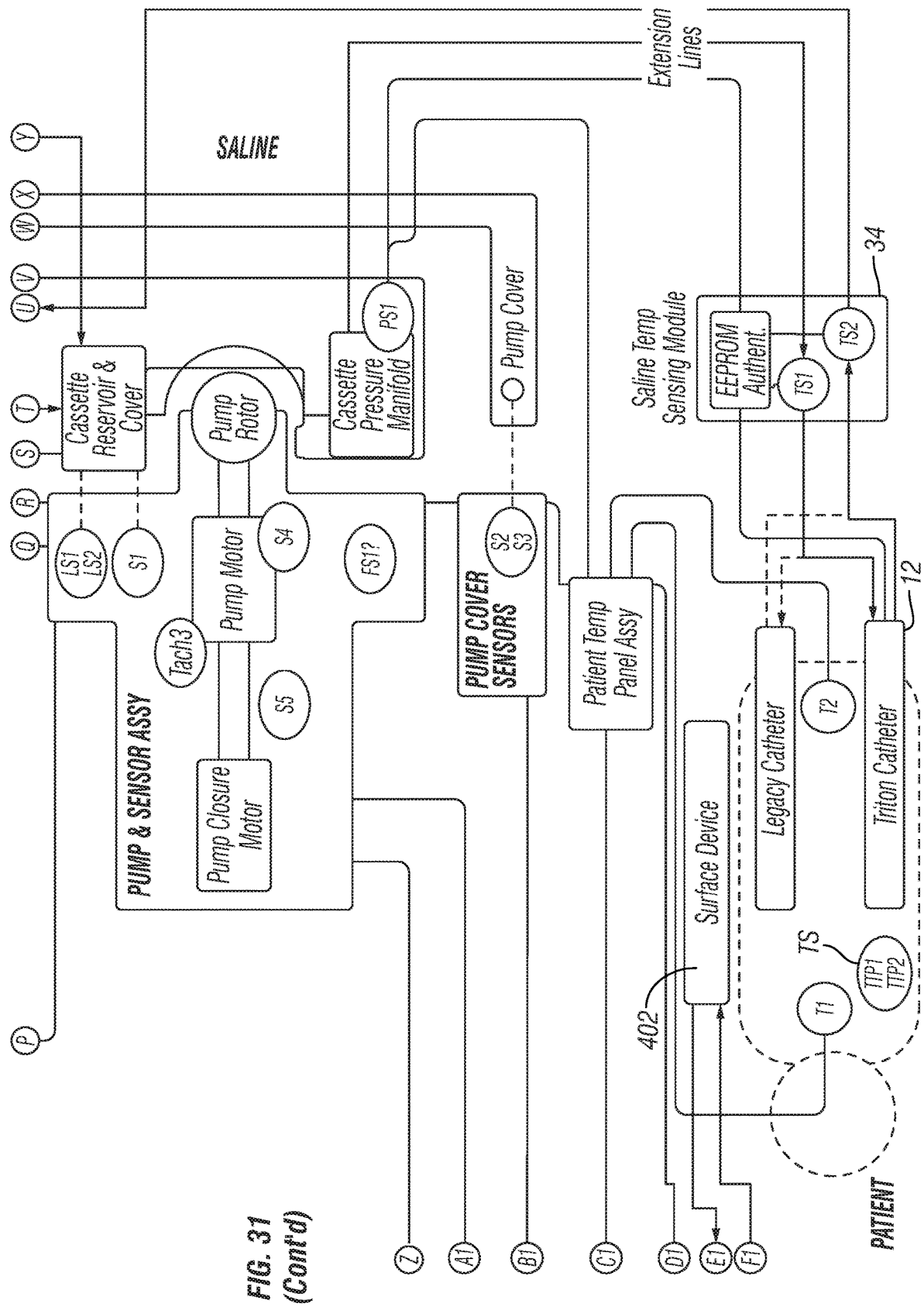

FIG. 31 is a schematic diagram of an example of a heat exchange system 10a capable of providing endovascular and/or body surface heat exchange. The system includes all of the elements described in the system 10 of FIG. 30 and, like FIG. 30, includes labeling according to the legend set forth above.

Additionally, this system 10a includes a body surface heat exchange fluid circuit 400 such that the system can provide body surface heat exchange by circulating warmed or cooled heat exchange fluid through at least one body surface heat exchanger 402 (e.g., a heat exchange pad, blanket, garment, etc.) Such operation of the body surface heat exchange fluid circuit 400 and body surface heat exchanger 402 may be performed in addition to or instead of endovascular heat exchange. The body surface heat exchange fluid circuit includes a fluid reservoir, a pump, a bypass valve, a vent valve, thermal exchange plates and a body surface heat exchange device, e.g., a pad. A fluid, e.g., water, is added to the fluid reservoir. When the bypass valve is closed to the vent valve and open to the bypass line, fluid circulates from the pump, through the body surface fluid chambers in the thermal exchange plates, the reservoir, the bypass valve, and back into the pump. This allows the volume of fluid within the system to come to thermal equilibrium with the thermal exchange plates, which may be useful in preparing the device to deliver temperature management treatment to the patient. In normal operation, the bypass valve is open to the vent valve and the vent valve is closed, and fluid circulates from the pump, through the body surface fluid chambers in the thermal exchange plates, through the reservoir, bypass valve, and vent valve, to the body surface heat exchange device and then back through the pump. To drain the body surface heat exchange device, the vent valve is opened which allows air into the circuit and prevents fluid from flowing from the bypass valve. This forces fluid out of the body surface heat exchange device to the pump. The pump is a positive displacement pump capable of pumping air or liquid through the body surface fluid chambers in the thermal exchange plates, to the reservoir. The reservoir is open to ambient air (to allow excess air to escape the system if introduced by the draining process or normal operation, or to accommodate changes in fluid volume due to thermal expansion) and includes a fill port or drain. The circuit also includes body surface heat exchange fluid temperature sensors to provide feedback to the controller, and fluid temperature sensors and fluid flow sensors for use in power calculations. Although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system configured to circulate a thermal exchange fluid through an endovascular heat exchanger, wherein the system comprises:
    a pump which produces a pulsatile flow of thermal exchange fluid; and
    a cassette configured to receive the thermal exchange fluid;
    at least one delivery conduit configured to connect to the endovascular heat exchanger, the at least one delivery conduit comprising an elongate pulse damping tube having a lumen through which said pulsatile flow of thermal exchange fluid flows,
    a cassette housing coupled to the cassette, the cassette housing receiving a portion of the elongate pulse damping tube at an outflow connector, the cassette housing comprising an inflow connector connected to a first tube in the cassette housing configured to direct the thermal exchange fluid to a first side of the cassette from the inflow connector and a second tube configured to direct the thermal exchange fluid from a second, opposite side of the cassette to a pump tubing, wherein the cassette allows the thermal exchange fluid to flow across the cassette from the first side to the second, opposite side;
    the pump tubing having an inlet coupled to the cassette housing and having an outlet coupled to the cassette housing, wherein at least a portion of the pump tubing extends externally from the cassette housing and is positionable in a raceway of the pump, the pump tubing being compressible by the pump;
    wherein the elongate pulse damping tube is configured to dampen, attenuate or reduce an amplitude of pulses in the thermal exchange fluid as the thermal exchange fluid flows through the lumen of the elongate pulse damping tube, and
    wherein the portion of the elongate pulse damping tube extends from the pump tubing, the pump tubing extending from the outflow connector to contact the pump, the portion of the elongate pulse damping tube directing the thermal exchange fluid from the pump tubing to the endovascular heat exchanger.

2. A system according to claim 1 wherein the elongate pulse damping tube is configured such that a volumetric capacity of the lumen will expand by 20 to 30 mL in response to a 60 psi increase in a pressure of the thermal exchange fluid flowing through the lumen, and, thereafter, will contract by 2 to 3 mL in response to an approximately 6 psi decrease in said pressure.

3. A system according to claim 1 further comprising:
    a cooler for cooling the thermal exchange fluid;
    a heater for warming the thermal exchange fluid;
    the cassette being positionable in relation to the heater and cooler such that said pump will cause thermal exchange fluid to circulate through the cassette and be warmed by the heated or cooled;
    the at least one delivery conduit extending from the cassette and being connectable to the endovascular heat exchanger; and
    at least one return conduit extending from the cassette and being connectable to the endovascular heat exchanger;
    whereby, when the at least one delivery conduit and said at least one return conduit are so connected to the endovascular heat exchanger, warmed or cooled thermal exchange fluid will circulate from the cassette, through the at least one delivery conduit, through the endovascular heat exchanger, through the at least one return conduit and back into the cassette.

4. A system according to claim 3 wherein the pump comprises a peristaltic pump in combination with the pump tubing which is compressed by said peristaltic pump in a manner that causes the pulsatile flow of thermal exchange fluid.

5. A system according to claim 4 wherein the pump tubing is attached to and extends from the cassette.

6. A system according to claim 3 wherein the heater and cooler comprise thermal exchange plates having a space therebetween within which the cassette is insertable.

7. A system according to claim 3 wherein the cassette comprises a bag attached to a frame.

8. A system according to claim 7 wherein a plurality of thermal exchange fluid flow channels are defined within the bag.

9. A system according to claim 7 wherein the cassette is positionable in relation to the heater and cooler by insertion of the cassette into a cassette-receiving space, and wherein the cassette is subsequently removable from the cassette-receiving space, and wherein the bag is lubricated to facilitate its insertion of said cassette into and removal from the cassette-receiving space.

10. A system according to claim 9 wherein holes, grooves or other surface features formed in the bag to facilitate its insertion into and removal from the cassette-receiving space.

11. A system according to claim 3 wherein the elongate pulse damping tube extends substantially an entire distance from the cassette to the endovascular heat exchanger when connected to the endovascular heat exchanger.

12. A system according to claim 11 wherein the elongate pulse damping tube is at least 80 inches in length.

13. A system according to claim 3 wherein:
the cassette housing is coupled to a vessel that contains thermal exchange fluid; and
a check valve is positioned in the cassette housing to allow thermal exchange fluid to flow from the vessel into the cassette housing but to prevent thermal exchange fluid from backflowing from the cassette housing into the vessel.

14. A system according to claim 13 wherein:
the pump operates in a forward mode for at least some of a time during set up or operation of the system;
in at least some instances, the pump also operates in a reverse mode for a period of time during set up or operation of the system; and
wherein the check valve is configured to deter backflow of thermal exchange fluid from the cassette into the vessel when the pump is operating in reverse mode.

15. A system according to claim 14 wherein the system further comprises a bubble detector and the pump operates in reverse mode in response to detection of a bubble by the bubble detector.

16. A system according to claim 1 wherein the elongate pulse damping tube is between 20 inches and 100 inches in length, has an inner diameter between 0.15 inches and 0.40 inches and a wall thickness between 0.06 inches and 0.25 inches.

17. A system according to claim 16 wherein a volume of the thermal exchange fluid in the lumen of the elongate pulse damping tube expands by 20 to 30 mL when a pressure of the thermal exchange fluid flowing through the lumen increases to 60 psi and, thereafter, contracts by 2 to 3 mL when the pressure drops by approximately 6 psi.

18. A system configured to circulate a thermal exchange fluid through an endovascular heat exchanger, said system comprising:
a reservoir that is fillable with the thermal exchange fluid;
a delivery conduit configured to connect to the endovascular heat exchanger, the delivery conduit comprising an elongate pulse damping tube having a lumen through which the thermal exchange fluid flows;
a housing coupled to the reservoir, the housing receiving a portion of the elongate pulse damping tube at an outflow connector, the housing comprising an inflow connector connected to a first tube in the housing configured to direct the thermal exchange fluid to a first side of the reservoir from the inflow connector and a second tube configured to direct the thermal exchange fluid from a second, opposite side of the reservoir to a pump tubing, wherein the reservoir allows the thermal exchange fluid to flow across the reservoir from the first side to the, opposite second side;
the pump tubing having an inlet coupled to the housing and having an outlet coupled to the housing, wherein at least a portion of the pump tubing extends externally from the housing and is positionable in a raceway of a pump, the pump tubing being compressible by the pump;
a return conduit through which the thermal exchange fluid may flow from the endovascular heat exchanger to the reservoir; and
wherein at least a portion of the elongate pulse damping tube is configured to dampen attenuate or reduce an amplitude of pulsations in the thermal exchange fluid as it flows through the lumen of the elongate pulse damping tube;
wherein the portion of the elongate pulse damping tube extends from the pump tubing, the portion of the elongate pulse damping tube directing the thermal exchange fluid from the pump tubing to the endovascular heat exchanger.

19. A system according to claim 18 wherein the elongate pulse damping tube is at least 80 inches in length.

20. A system according to claim 18 wherein the elongate pulse damping tube is between 20 inches and 100 inches in length, has an inner diameter between 0.15 inches and 0.40 inches and a wall thickness between 0.06 inches and 0.25 inches.

21. A system according to claim 20 wherein a volume of the thermal exchange fluid in the lumen of the elongate pulse damping tube expands by 20 to 30 mL as a pressure of the thermal exchange fluid flowing through the lumen increases to 60 psi and, thereafter, contracts by a volume of 2 to 3 mL as the pressure drops by approximately 6 psi.

22. A system according to claim 18 wherein the reservoir comprises a cassette through which the thermal exchange fluid circulates.

23. A system according to claim 22 further comprising an apparatus for warming or cooling the thermal exchange fluid as it circulates through the cassette.

24. A system according to claim 18 further comprising a pump which circulates the thermal exchange fluid from the reservoir, through the delivery conduit, through the endovascular heat exchanger, through the return conduit and back into the reservoir.

25. A system according to claim 18 wherein the elongate pulse damping tube is configured such that a volumetric capacity of the lumen will expand by 20 to 30 mL in response to a 60 psi increase in a pressure of the thermal exchange fluid flowing through the lumen and, thereafter, will contract by 2 to 3 mL in response to an approximately 6 psi decrease in the pressure.

* * * * *